(12) United States Patent
Wilson et al.

(10) Patent No.: US 9,980,812 B2
(45) Date of Patent: *May 29, 2018

(54) MITRAL VALVE SPACER AND SYSTEM AND METHOD FOR IMPLANTING THE SAME

(71) Applicant: Cardiosolutions, Inc., West Bridgewater, MA (US)

(72) Inventors: Jonathan E. Wilson, Mattapoisett, MA (US); John Murphy, Plymouth, MA (US); Jack Robertson, Abington, MA (US); Christopher Seguin, Norton, MA (US)

(73) Assignee: Cardiosolutions, Inc., West Bridgewater, MA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/305,089

(22) Filed: Jun. 16, 2014

(65) Prior Publication Data

US 2014/0371843 A1 Dec. 18, 2014

Related U.S. Application Data

(60) Provisional application No. 61/835,093, filed on Jun. 14, 2013.

(51) Int. Cl.
*A61F 2/24* (2006.01)

(52) U.S. Cl.
CPC ............... *A61F 2/24* (2013.01); *A61F 2/246* (2013.01); *A61F 2/2466* (2013.01);
(Continued)

(58) Field of Classification Search
CPC .............. A61F 2/246; A61F 2250/0003; A61F 2/2466; A61F 2/2427; A61F 2/2445;
(Continued)

(56) References Cited

U.S. PATENT DOCUMENTS 2,625,967 A 1/1953 Stull
2,549,731 A 4/1954 Wattley
(Continued)

FOREIGN PATENT DOCUMENTS

CN 1961983 A 5/2007
CN 101484093 A 7/2009
(Continued)

OTHER PUBLICATIONS

PCT Notification of Transmittal of the International Search Report and the Written Opinion of the International Searching Authority, or the Declaration, PCT/US2014/042465, dated Sep. 8, 2014 (12 pages.).

(Continued)

*Primary Examiner* — Katherine M Shi
(74) *Attorney, Agent, or Firm* — Thomas J. Engellenner; Reza Mollaaghababa Pepper Hamilton LLP

(57) ABSTRACT

A heart valve implant is disclosed herein. The heart valve implant comprises an inflatable valve body, a shaft, an anchor assembly and an inflation (injection) port. Also disclosed herein, are methods of trans-apically and transseptally delivering a heart valve implant within a heart such that the valve body can be inflated in situ to partially or completely restrict blood flow through a heart valve in a closed position. The inflation (injection) port permits inflation of the valve body with an adjustable amount of an inflation fluid to attain a desired degree of inflation of the valve body when disposed within the heart valve.

11 Claims, 43 Drawing Sheets

(52) U.S. Cl.
CPC .............. *A61F 2250/0003* (2013.01); *A61F 2250/0004* (2013.01); *A61F 2250/0098* (2013.01)

(58) Field of Classification Search
CPC ...... A61F 2220/0008; A61F 2250/0004; A61F 2250/0098; A61F 2/24; A61F 2/2481; A61F 2/2487; A61B 2017/00243
USPC ...... 606/1.11, 1.36, 2.1, 2.11, 2.36; 623/900
See application file for complete search history.

(56) References Cited

U.S. PATENT DOCUMENTS

| | | |
|---|---|---|
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers et al. |
| 3,589,392 A | 6/1971 | Meyer |
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,246,893 A | 1/1981 | Berson |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,836,204 A | 6/1989 | Landymore et al. |
| 4,865,030 A | 9/1989 | Polyak |
| 4,960,424 A | 10/1990 | Grooters |
| 5,002,067 A | 3/1991 | Berthelsen et al. |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,554,185 A | 9/1996 | Block et al. |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,713,954 A * | 2/1998 | Rosenberg ............ A61F 2/2481 600/17 |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,964,806 A * | 10/1999 | Cook ............... A61B 17/062 600/30 |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,183,512 B1 | 2/2001 | Howanec et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,406,420 B1 | 6/2002 | McCarthy et al. |
| 6,415,693 B1 | 7/2002 | Simon et al. |
| 6,416,549 B1 | 7/2002 | Chinn et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,592,606 B2 | 7/2003 | Huter et al. |
| 6,629,534 B1 | 10/2003 | St Goar et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artof et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,964,684 B2 | 11/2005 | Ortiz et al. |
| 6,971,998 B2 | 12/2005 | Rosenman et al. |
| 6,974,476 B2 | 12/2005 | McGuckin, Jr. et al. |
| 6,976,950 B2 | 12/2005 | Connors et al. |
| 6,978,176 B2 | 12/2005 | Lattouf |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,335,213 B1 | 2/2008 | Hyde et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,704,268 B2 | 4/2010 | Chanduszko |
| 7,753,949 B2 | 7/2010 | Lamphere et al. |
| 7,785,366 B2 | 8/2010 | Maurer et al. |
| 7,927,370 B2 | 4/2011 | Webler et al. |
| 7,942,928 B2 | 5/2011 | Webler et al. |
| 7,963,973 B2 | 6/2011 | Nguyen et al. |
| 8,092,525 B2 | 1/2012 | Eliasen et al. |
| 8,118,822 B2 | 2/2012 | Schaller et al. |
| 8,216,302 B2 | 7/2012 | Wilson et al. |
| 8,486,136 B2 | 7/2013 | Maurer et al. |
| 8,506,623 B2 | 8/2013 | Wilson et al. |
| 2001/0007956 A1 | 7/2001 | Letac et al. |
| 2001/0010017 A1 | 7/2001 | Cribier et al. |
| 2001/0018611 A1 | 8/2001 | Solem et al. |
| 2002/0029080 A1 | 3/2002 | Mortier et al. |
| 2002/0032480 A1 | 3/2002 | Spence et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0169377 A1 | 11/2002 | Khairkhahan et al. |
| 2002/0169502 A1 | 11/2002 | Mathis |
| 2002/0183838 A1 | 12/2002 | Liddicoat et al. |

(56) References Cited

U.S. PATENT DOCUMENTS

| | | |
|---|---|---|
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0120264 A1 | 6/2003 | Lattouf |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148019 A1* | 7/2004 | Vidlund ............ A61B 17/00234 623/2.36 |
| 2004/0148020 A1 | 7/2004 | Vidlund et al. |
| 2004/0181256 A1 | 9/2004 | Glaser |
| 2004/0210304 A1 | 10/2004 | Seguin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |
| 2004/0260322 A1 | 12/2004 | Rudko et al. |
| 2005/0021056 A1 | 1/2005 | St. Goar et al. |
| 2005/0027337 A1 | 2/2005 | Rudko et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0149182 A1 | 7/2005 | Alferness et al. |
| 2005/0159810 A1 | 7/2005 | Filsoufi |
| 2005/0222488 A1 | 10/2005 | Chang et al. |
| 2005/0229433 A1 | 10/2005 | Cachia |
| 2005/0288786 A1 | 12/2005 | Chanduszko |
| 2006/0020335 A1 | 1/2006 | Kowalsky et al. |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0016286 A1 | 1/2007 | Herrmann et al. |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0167981 A1 | 7/2007 | Opalski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0232992 A1 | 10/2007 | Kutsko et al. |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0097595 A1 | 4/2008 | Gabbay |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0208329 A1* | 8/2008 | Bishop ............... A61B 17/10 623/2.11 |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0082874 A1 | 3/2009 | Cachia |
| 2009/0093670 A1 | 4/2009 | Annest et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0016655 A1 | 1/2010 | Annest et al. |
| 2010/0022948 A1 | 1/2010 | Wilson et al. |
| 2010/0042208 A1 | 2/2010 | Herrmann |
| 2010/0324668 A1 | 12/2010 | Maurer et al. |
| 2012/0143320 A1 | 6/2012 | Eliasen et al. |
| 2013/0211513 A1* | 8/2013 | Rourke ............... A61F 2/2466 623/2.37 |
| 2015/0127097 A1 | 5/2015 | Neumann et al. |
| 2015/0335424 A1 | 11/2015 | McLean |

FOREIGN PATENT DOCUMENTS

| | | |
|---|---|---|
| CN | 105473106 A | 4/2016 |
| EP | 1323438 | 2/2003 |
| EP | 0125393 | 8/2007 |
| GB | 1264472 | 2/1972 |
| GB | 1268484 | 3/1972 |
| GB | 1388064 | 3/1975 |
| WO | 8900030 A1 | 1/1989 |
| WO | WO 2003049619 | 6/2003 |
| WO | 2003096932 A1 | 11/2003 |
| WO | WO 2006032051 | 3/2006 |
| WO | WO 2006064490 | 6/2006 |
| WO | WO 2006091597 | 8/2006 |
| WO | WO 2006111391 | 10/2006 |
| WO | WO 2006127509 | 11/2006 |
| WO | WO 2007064810 | 6/2007 |
| WO | WO 2007078772 | 7/2007 |
| WO | WO 2007100409 | 9/2007 |
| WO | WO 2007140470 | 12/2007 |
| WO | WO 2008079828 | 7/2008 |
| WO | 2008141322 A1 | 11/2008 |
| WO | WO 2009053952 | 4/2009 |
| WO | 2011146759 A2 | 11/2011 |
| WO | 2013021374 A2 | 2/2013 |

OTHER PUBLICATIONS

Acar et al., AREVA: Multicenter Randomized Comparison of Low-Dose Versus Standard-Dose Anticoagulation in Patients With Mechanical Prosthetic Heart Valves, Circulation, Nov. 1, 1996, 2017-12, vol. 94, No. 9.

Casselman et al., Mitral Valve Surgery Can Now Routinely Be Performed Endoscopically, Downloaded from eire.ahajournals.org, Aug. 26, 2008, 11-48-11-54.

Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.

Clinical Trials.gov, Comparing the Effectiveness of a Mitral Valve Repair Procedure in Combination With Coronary 3 Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.

Clinical Trials.gov, Safety and Efficacy Study of the PTMA Device to Reduce Mitral Valve Regurgitation in Patients With Heart Failure (PTOLEMY2Canada), hllp:I/clinicaltrials.gov/ct2/show/study/NCT00815386?term=Viacor&rank=3, 1-3, Aug. 25, 2008, pp. 1-4.

(56) References Cited

OTHER PUBLICATIONS

Clinical Trials.gov, Study of Safety and Efficacy of the Percutaneous Reduction of Mitral Valve Regurgitation in Heart Failure Patients (PTOLEMY-2), hllp:I/clinicaltrials.gov/ct2/show/NCT00787293?term=Viacor&rank=5, 1-2, Aug. 25, 2008, pp. 1-3.
ClinicaiTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091 ?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT0057161O?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOT-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID—Valvular and Ventricular Improvement Via iCoapsys Delivery—Feasibility Study, http:// clinicaltrials.gov/ct2/show/NCT00512005?term=mitral+valve&rank=12, Aug. 25, 2008, 1-4.
Cohen, Trans-Septal Technique for Tandemheart Insertion, Lenox Hill Heart and Vascular Institute of New York, Barcelona May 22-May 25, 2007, 18 pages.
Corbisiero et al., Does Size Really Matter? A Comparison of the Riata Lead Family Based on Size and Its Relation to Performance, Pace, Jun. 2008, vol. 31, 722-726.
Crabtree et al., Recurrent Mitral Regurgitation and Risk Factors for Early and Late Mortality After Mitral Valve Repair for Functional Ischemic Mitral Regurgitation, The Society of Thoracic Surgeons , 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.
Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
De Bonis et al., Similar long-term results of mitral valve repair for anterior compared with posterior leaftet prolapse, The Journal of Thoracic and Cardiovascular Surgery, Feb. 2006, 364-370, vol. 131, No. 2.
Deloche et al., Valve repair with Carpentier techniques the second decade, The Journal of Thoracic and Cardiovascular Surgery, Jun. 1990, 990-1002, vol. 99, No. 6.
Del Valle-Fernandez et al., Transcatheter heart valves for the treatment of aortic stenosis: state-of-the-art, Minerva Cardioangiologica, Oct. 2008, vol. 56, No. 5, 543-556.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.

Detaint et al., Surgical Correction of Mitral Regurgitation in the Elderly—Outcomes and Recent Improvements, Downloaded from circ.ahajournals.org, Aug. 26, 2008, 265-272.
Douthiti, Cardiac Dimensions® Inc. Receives CE Mark for CARILLQWM Mitral Contour SystemTM, Cardiac Dimensions—News, htpp:I/www.cardiacdimensions.com/usa/press-release-2-4-09.html, downloaded Feb. 24, 2009, 1-2.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eisenhauer et al., Closure of Prosthetic Paravalvular Mitral Regurgitation With the Gianturco-Grifka Vascular Occlusion Device, Catheterization and Cardiovascular Interventions, 2001, 5 pages,vol. 54.
El Tchaninoff, Clinical results of percutaneous aortic valve implantation, Euro PCR07, Cribier-Edwards, 30 pages.
Epstein et al., Gross and Microscopic Pathological Changes Associated With Nonthoracotomy Implantable Defibrillator Leads, Downloaded from circ.ahajournals.org, Jul. 23, 2008, 1517-24.
Epstein et al., Embolic Complications Associated With Radiofrequency Catheter Ablation, The American Journal of Cardiology, Mar. 15, 1996, 655-658, vol. 77.
European Examination Report dated Aug. 11, 2011 issued in European Patent No. 08 755 418.4, 3 pages.
European Examination Report dated Aug. 4, 2011 issued in European Patent No. 06 816 336.9, 3 pages.
European Search Report dated Jul. 12, 1984 cited in EP0125393.
European Intent to Grant dated Feb. 22, 2013 issued in Europe Patent Application No. 08 755 418.4, 7 pages.
European Search Report dated Mar. 6, 2013 issued in European Patent Application No. 10804952.9, 8 pages.
European Office Action dated Nov. 7, 2013 issued in European Patent Application No. 10 804 952.9 (5 pages).
Evalve reports 1st MitraClip treatments in the Netherlands, Medical Device Daily, Feb. 19, 2009, vol. 13, No. 32, 2 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.
Feldman et al., Patient selection for percutaneous mitral valve repair: insight from early clinical trial applications, Nature Clinical Practice Cardiovascular Medicine, Feb. 2008, 84-90, vol. 5, No. 2.
Feldman et al., Percutaneous Mitral Valve Repair Using the Edge-to-Edge Technique—Six-Month Results of the EVEREST Phase I Clinical Trial, Journal of the American College of Cardiology, Dec. 6, 2005, 2134-40, vol. 46, No. 11.
Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.
Fitts et al. , Fluoroscopy-Guided Femoral Artery Puncture Reduces the Risk of PCI-Related Vascular Complications, Journal of Interventional Cardiology, vol. 21, No. 3, 2008, 273-278.
French catheter scale chart http://en.wikipedia.org/wiki/French_catheter_scale_chart, Dec. 20, 2006, 1 page.

(56) References Cited

OTHER PUBLICATIONS

Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132,2009,419-428.
General Physical Properties of PVA Sponge (values are not guaranteed), Ceiba Technologies, http://www.ceibatech.com/PVASpongeDate.htm, Dec. 20, 2006 3 pages.
Geyfman et al.. Cardiac Tamponade as Complication of Active-Fixation Atrial Lead Perforations: Proposed Mechanism and Management Algorithm. PACE, Apr. 2007, vol. 30, 498-501.
Gillinov et al., Durability of Mitral Valve Repair for Degenerative Disease, The Journal of Thoracic and Cardiovascular Surgery, Nov. 1998, 734-743, vol. 116, No. 5.
Glenn, et al., "The Surgical Treatment of Mitral Insufficiency with Particular Reference to the Application of a Vertically Suspended Graft" Jul. 1956 (pp. 59-77).
Glenn, et al., "The Implantation of a Vascularized Graft in the Chambers of the Heart" 1954 (pp. 5-11 ).
Glenn, et al., "The Surgical Treatment of Mitral Insufficiency: the Fate of a Vascularized Transchamber Intracardiac Graft" Apr. 1955 (pp. 510-518).
Glover, et al., "The Fate of Intracardiac Pericardia! Grafts as Applied to the Closure of Septal Defects and to the Relief of Mitral Insufficiency" 1952 (pp. 178-185).
Gorman et al., Surgical Therapy for Mitral Regurgitation: The Key to Preventing Heart Failure?, Prevention of Hean Failure After Myocardial Infarction, 2008, 211-215.
Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.
Grossi et al., Late Results of Mitral Valve Reconstruction in the Elderly, The Society of Thoracic Surgeons, 2000, 1224-6,70.
Grossi et al., Minimally Invasive Mitral Valve Surgery: A 6-Year Experience With 714 Patients, The Society of Thoracic Surgeons, 2002, 660-4, 74.
Harken, et al., "The Surgical Treatment of Mitral Insufficiency," The Journal of Thoracic Surgery,1954 (pp. 604-627).
Harken, et al., "The Surgical Correction of Mitral Insufficiency" 1953 (pp. 4-7).
Harper, Evalve Announces Enrollment Completion of the Everest Randomized Study, http://www.evalveinc.com/ europe/press/17.html, downloaded Feb. 24, 2009, 1-3.
Harper, Two-Year Follow-Up Data Demonstrates Preservation of Adequate Mitral Valve Area in Patients Treated with the MitraCiip®-system, http://www.evalveinc.com/europe/press/21.html, downloaded Feb. 24, 2009, 1-3.
Henderson, et al., "The Surgical Treatment of Mitral Insufficiency" Jun. 1953 (pp. 858-868).
Hendren et al., Mitral Valve Repair for Ischemic Mitral Insufficiency, The Society of Thoracic Surgeons, 1991, 1246-52, 52.
Heupler et al., Infection Prevention Guidelines for Cardiac Catheterization Laboratories, Catheterization and Cardiovascular Diagnosis, 1992, 260-263, 25.
Hourihan et al., Transcatheter Umbrella Closure of Valvular and Paravalvular Leaks, American College of Cardiology, Nov. 15, 1992,7 pages, vol. 20, No. 6.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.
Hytowitz, First U.S. Patients Enrolled in the Realism Continued Access Study, evalve, http://www.evalveinc.com/ europe/press/22/html, downloaded Feb. 24, 2009, 2 pages.
Ibrahim et al., The St. Jude Medical prosthesis—A thirteen-year experience, The Journal of Thoracic and Cardiovascular Surgery, Aug. 1994, 221-230, vol. 108, No. 2.
Intent to Grant dated Jan. 2, 2013 issue in European Patent Application No. 06816336.9, 7 pages.
International Search Report and Written Opinion dated Sep. 22, 2008 issued in PCT Application No. PCT/US08/63560 11 pages.
International Search Report and Written Opinion dated Sep. 29, 2008 issued in PCT Application No. PCT/US08/63568 12 pages.
International Preliminary Report on Patentability dated Jan. 31, 2012 issued in PCT Patent Application No. PCT/ US2010/043360, 7 pages.
International Search Report and Written Opinion dated Feb. 25, 2009 issued in PCT Application No. PCT/ US08/083570, 13 pages.
International Search Report and Written Opinion dated Apr. 2, 2009 issued in PCT Application No. PCT/US08/083574, 8 pages.
International Search Report and Written Opinion dated Jul. 6, 2010 issued in PCT Patent Application No. PCT/US2010/032764, 9 pages.
International Search Report and Written Opinion dated Sep. 22, 2008 issued in PCT Application No. PCT/ US08/63568. 11 pages.
International Search Report and Written Opinion dated Sep. 29, 2008 issued in PCT Application No. PCT/ US08/63568. 12 pages.
International Search Report and Written Opinion, May 11, 2007 (6 pages) filed in corresponding PCT application PCT/US06/39011 (8 pages).
International Search Report and Written Opinion dated Jan. 16, 2009 issued in PCT Application No. PCT/US08/83497 10 pages.
International Search Report and Written Opinion dated Sep. 21, 2010 issued in PCT Patent Application No. PCT/US201 0/043360, 9 pages.
International Search Report and Written Opinion dated Aug. 11, 2009 issued in PCT Application No. PCT/ US2009/046995, 11 pages.
International Preliminary Report on Patentability dated May 27, 2010 issued in PCT/US2008/083574, 4 pages.
International Preliminary Report on Patentability and Written Opinion, issued in PCT/US2008/063560, dated Nov. 26, 2009, 8 pages.
International Preliminary Report and Written Opnion issued in PCT/US2008/083570, dated May 27, 2010, 4 pages.
Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.
Jilaihawi et al., Percutaneous Aortic Valve Replacement in Patients with Challenging Aortoiliofemoral Access, Catheterization and Cardiovascular Interventions, 2008, vol. 72, 885-890.
Johns, et al., "Mitral Insufficiency: the Experimental Use of a Mobile Polyvinyl Sponge Prosthesis," Annals of Surgery, Sep. 1954 (pp. 335-341).
Jovin et al.. Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journof the American Society of Echocardiography, Aug. 2008, vol. 21, No. 8, 912-921.
Kasegawa et al., Mitral Valve Repair for Anterior Leaflet Prolapse With Expanded Polytetraftuoroethylene Sutures, The Society of Thoracic Surgeons, 2006, 1625-31, 81.

(56) References Cited

OTHER PUBLICATIONS

Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.

Kempfert et al., Minimally invasive off-pump valve-in-a-valve implantation: the atrial transcatheter approach for re-operative mitral valve replacement, European Heart Journal, 2008, vol. 29, 2382-2387.

Kerensky, Complications of Cardiac Catherization and Strategies to Reduce Risks, Diagnostic and Therapeutic Cardiac Catheterization, 1998, Chapter 8, 91-105.

Kodali et al., Transcatheter Valve Repair and Replacement, Downloaded from arjournals.annualreviews.org by National Institute of Health Library on Feb. 25, 2009, 14 pages.

Koertke et al., INR Self-Management Permits Lower Anticoagulation Levels After Mechanical Heart Valve Replacement, downloaded from circ.ahajournals.org, Aug. 26, 2008, 11-75-11-78.

Kratz et al., St. Jude Prosthesis for Aortic and Mitral Valve Replacement: A Ten-Year Experience, The Society of Thoracic Surgeons, 1993, 462-8, 56.

Kron et al., Surgical Relocation of the Posterior Papillary Muscle in Chronic Ischemic Mitral Regurgitation, The Society of Thoracic Surgeons, 2002,600-1,74.

Kuck et al., Best of Structural Heart Disease Abstracts, TCT-124, The American Journal of Cardiology, Oct. 20-25, 2007, 58L.

Kuwahara et al., Mechanism of Recurreni/Persistent Ischemic/Functional Mitral Regurgitation in the Chronic Phase After Surgical Annuloplasty—Importance of Augmented Posterior Leaftet Tethering, Circulation, Jul. 4, 2006, 1-529-1-534.

Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.

Laskey et al., Multivariable Model for Prediction of Risk of Significant Complication During Diagnostic Cardiac Catheterization, Catheterization and Cardiovascular Diagnosis, 1993, 185-190, 30.

Lee et al., Mitral Valve Reconstruction: Experience Related to Early and Late Mortality and Reoperation, J Heart Valve Dis, Nov. 2005,715-721, vol. 14, No. 6.

Leung et al., Percutaneous Mitral Valve Repair—An overview of the current devices and techniques, Coronary/ Cardiac Interventions—Endovascular Today, Oct. 2006, 26-33.

Levine et al., Mechanistic Insights into Functional Mitral Regurgitation, Valvular Heart Disease, 2009, 125-129.

Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

Lim et al., Percutaneous Transthoracic Ventricular Puncture for Diagnostic and Interventional Catheterization, Catheterization and Cardiovascular Interventions, 2008, 915-918, 71.

Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.

Little et al., Three-Dimensional Ultrasound Imaging Model of Mitral Valve Regurgitation: Design and Evaluation, Ultrasound in Medicine and Biology, 2008, vol. 34, No. 4, 647-654.

Llaneras et al., Large Animal Model of Ischemic Mitral Regurgitation, The Society of Thoracic Surgeons—Ischemic Mitral Insufficiency, 1994, vol. 57, 432-439.

Lozonschi et al., Transapical Mitral Valved Stent Implantation, The Society of Thoracic Surgeons, 2008, 745-8, 86.

Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.

Magne et al., Ischemic Mitral Regurgitation: A Complex Multifaceted Disease, Cardiology, 2009, vol. 112, 244-259.

Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.

Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.

Matthews, Anatomy of the Heart, Definitions Cardiology Explained and Presented by Robert Matthews, MD, http:!/ www.rjmatthewsmd.com/Definitions/anatomy_oflhe_heart.htm, printed Jul. 28, 2008, 265 pages.

McClure et al.. Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.

McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.

Mehra et al., Surgery for Severe Mitral Regurgitation and Left Ventricular Failure: What Do We Really Know?, Journal of Cardiac Failure, Mar. 2008, 145-150. vol. 14, No. 2.

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.

Messas et al., Efficacy of Chordal Cutting to Relieve Chronic Persistent Ischemic Mitral Regurgitation, Circulation, Sep. 9, 2003, 11-111-11-115.

Meurin et al., Thromboembolic events early after mitral valve repair: Incidence and predictive factors, International Journal of Cardiology, 2008, 45-52, 126.

Mirable et al., What are the characteristics of patients with severe, symptomatic, mitral regurgitation who are denied surgery?, The European Society of Cardiology, 2007, 1358-65,28.

Mitchell et al., Complications, Cardiac catheterization and coronary intervention, Chapter 9, 2008, 238-270.

Mishra et al., Coapsys Mitral Annuloplasty for Chronic Functional Ischemic Mitral Regurgitation: 1-Year Results, The Society of Thoracic Surgeons, 2006, 42-46, 81.

Modi et al., Minimally invasive mitral valve surgery: a systematic review and meta-analysis, European Journal of Cardia-Thoracic Surgery, 2008, vol. 34, 943-952.

Moore, et al., "Unsuitability of Transventricular Autogenous Slings for Diminishing Valvular Insufficiency" Feb. 1953 (pp. 173-182).

Morgan et al.. Left Heart Catheterization by Direct Ventricular Puncture: Withstanding the Test of Time, Catheterization and Cardiovascular Diagnosis, 1989, 87-90, 16.

Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.

Mullins, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.

Mullins. Vascular access. Cardiac Catheterization in Congenital Heart Disease; Pediatric and Adult, 2006, Chapter 4, pp. 115-117, 5 pages, Blackwell Futura, USA.

Mullins, Aortic valve dilation, Cardiac Catheterization in Congenital Heart Disease; Pediatric and Adult, 2006, Chapter 19, pp. 487-489, 5 pages, Blackwell Futura, USA.

Mullins, Foreign body removal, Cardiac Catheterization in Congenital Heart Disease; Pediatric and Adult, 2006, Chapter 12, pp. 350-377, 30 pages, Blackwell Futura, USA.

Murday et al., A Prospective Controlled Trial of St. Jude Versus Starr Edwards Aortic and Mitral Valve Prostheses, The Society of Thoracic Surgeons, 2003, 66-74, 76.

(56) References Cited

OTHER PUBLICATIONS

Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.

Nifong et al., Robotic mitral valve surgery: A United States multi-center trial, The Journal of Thoracic and Cardiovascular Surgery, Jun. 2005, 1395-1404, vol. 129, No. 6.

Ning et al., Live three-dimensional transesophageal echocardiography in mitral valve surgery, Chinese Medical Journal, 2008, vol. 121, No. 20,2037-2041.

Noto et al., Cardiac Catheterization 1990: A Report of the Registry of the Society for Cardiac Angiography and Interventions (SCA&I), Catheterization and Cardiovascular Diagnosis, 1991, 75-83, 24.

Notzold et al., Microemboli in aortic valve replacement, Future Drugs Ltd, Expert Rev. Cardiovasc. Ther., Vol4, No. 6, 2006, 853-859.

Ohlow et al., Incidence and outcome of femoral vascular complications among 18,165 patients undergoing cardiac catheterisation, International Journal of Cardiology, 2008, 1-6.

Onundarson et al., Warfarin anticoagulation intensity in specialist-based and in computer-assisted dosing practice, International Journal of Laboratory Hematology, 2008, vol. 30, 382-389.

Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.

Pai et al., Effect of Atrial Fibrillation on the Dynamics of Mitral Annular Area, J. Heart Valve Dis., Jan. 2003, vol. 12, No. 1, 31-37.

Palacios et al., Safety and Feasibility of Acute Percutaneous Septal Sinus Shortening: First-in-Human Experience, Catheterization and Cardiovascular Interventions, 2007, vol. 69, 513-518.

Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.

Pedersen et al., iCoapsys Mitral Valve Repair System: Percutaneous Implantation in an Animal Model, Catheterization and Cardiovascular Interventions, 2008, 125-131,72.

Piazza et al., Transcatheter Mitral Valve Repair for Functional Mitral Regurgitation: Coronary Sinus Approach, Journal of Interventional Cardiology, 2007, 495-508, vol. 20, No. 6.

Preliminary Report on Patentability dated Nov. 10, 2011 issued in PCT Patent Application No. PCT/ US2010/032764, 4 pages.

Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.

PVA Datasheet, www.sponge-pva.com/data.htm. Dec. 20. 2006, 2 pages.

PVA Sponge W (wet) & D (dry), Ceiba Technologies, http://www.ceibatech.com/PVASpongeW&D.htm, Dec. 20, 2007 5 pages.

Rashkind et al. Nonsurgical closure of patent ductus arteriosus: clinical application of the Rash kind PDA Occluder System, Therapy and Prevention—Congenital Heart Disease, Mar. 1987, 10 pages, vol. 75, No. 3.

Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.

Rinaldi et al., Best of Structural Heart Disease Abstracts, TCT-123, The American Journal of Cardiology, Oct. 20-25, 2007, 57L.

Rodes-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.

Ruiz, New Percutaneous Approaches for Mitral Regurgitation, Lenox Hill Heart and Vascular Institute of New York, May 13-16, 2008, 26 pages.

Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.

Ryhanen et al, "In vivo biocompatibility evaluation of nickel-titanium shape memory metal alloy: Muscle and perineural tissue responses and encapsule membrane thickness," Jan. 19, 1998, Journal of Biomedical Materials Research, 41, 481.

Sakakibara, "A Surgical Approach to the Correction of Mitral Insufficiency" Aug. 1955 (pp. 196-203).

Satpathy et al., Delayed Defibrillator Lead Perforation: An Increasing Phenomenon, Pace, Jan. 2008, vol. 31, 10-12.

Schofer, Percutaneous MVR: Clinical Evaluation—The Carillon Experience, EuroPCR 2007, Barcelona, Spain, Ma~ 22-25, 2007, 35 pages.

Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.

Seeburger et al., Minimal invasive mitral valve repair for mitral regurgitation: results of 1339 consecutive patients, European Journal of Cardio-thoracic Surgery, 2008, 1-6.

Siminiak et al., Best of Structural Heart Disease Abstracts, TCT-125, The American Journal of Cardiology, Oct. 20-25, 2007, 58L.

Southard et al., Current Catheter-Based Treatments of Functional Mitral Regurgitation, Cardiac Interventions Today, Jun. 2007,41-44.

Spencer, Viacor, Inc. Announces First Patient Treated in PTOLEMY-2 Study, http://www.viacorinc.com/viacor_news. html, Nov. 14, 2008, downloaded Feb. 24, 2009, 2 pages.

Sterlinski et al., Subacute cardiac perforations associated with active fixation leads, Clinical Research Leads and Lead Extraction, Europace, 2009, vol. 11, 206-212.

Svensson et al., United States Feasibility Study ofTranscatheter Insertion of a Stented Aortic Valve by the Left Ventricular Apex, The Society of Thoracic Surgeons, 2008, 46-55, 86.

SPI-Chem™ Vinylec® (Formvar®) Resins, http://www.2spi.com/catalog/submal/formvar-resins.shtml, Dec. 20, 2006, 5 pages.

Toledano et al., Mitral regurgitation: Determinants for referral for cardiac surgery by Canadian cardiologists, Can J. Cardiol, Mar. 1, 2007, 209-214, vol. 23, No. 3.

Tops et al., Percutaneous Valve Procedures: An Update, Curr Probl Cardiol, Aug. 2008, 417-426.

Trippel, et al., "Reinforced Ivalon Sponge as an Aortic Prosthesis" Feb. 1960 (9 pages).

Turakhia et al., Rates and severity of perforation from implantable cardioverter-defibrillator leads: A 4-year study, J Interv Card Electrophysiol, 2009, vol. 24, 47-52.

Vahanian, The Cardiologist's Perspective on the Future of Percutaneous Mitral Valve Repair, Euro PCR07, 53 pages.

Vahanian, Coronary Sinus and Direct Annuloplasty Percutaneous Mitral Valve Repair, Innovations in Cardiovascular Interventions, Dec. 7-9, 2008, Tel-Aviv, Israel, 22 pages.

Vahanian, Edwards MONARC system—Evolution Interim Results, 31 pages.

Vahanian, Overview on Percutaneous Mitral Valve Technology, Euro PCR07, Transcatheter Valve Symposium, Barcelona, May 22-25, 2007, 23 pages.

Van Gelder et al., Diagnosis and Management of Indavertently Placed Pacing and ICD Leads in the Left Ventricle: A Multicenter Experience and Review of the Literature, Pace, May 2000, vol. 23, 877-883.

Vinylec® Resins, http://www.2spi.com/catalog/submal/vinylec-physical.html, Dec. 20, 2006, 1 page.

Vranckx et al., The Tandem Heart®, percutaneous transseptalleft ventricular assist device: a safeguard in high-risk percutaneous coronary interventions. The six-year Rotterdam experience, Clinical research EuroInterv., 2008, vol. 4, 331-337.

Walther et al., Transapical minimally invasive aortic valve implantation; the initial 50 patients, European Journal o Cardio-thoracic Surgery, 2008, 983-988, 33.

Webb et al., Percutaneous Mitral Annuloplasty With the MONARC System: Preliminary Results From the Evolution Trial, TCT-103, The American Journal of Cardiology, Oct. 22-27, 2006, 49M.

(56) References Cited

OTHER PUBLICATIONS

Webb et al., Percutaneous Transvenous Mitral Annuloplasty—Initial Human Experience with Device Implantation in the Coronary Sinus, downloaded from circ.ahajournals.org, Aug. 26, 2008, 851-855.

Webster et al., Impact of transvenous ventricular pacing leads on tricuspid regurgitation in pediatric and congenital heart disease patients, J Interv Card Electrophysiol, 2008, 65-68, 21.

Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.

Xiangming et al., In Vivo Characterization of Attachment Safety Between Cardiac Pacing Lead and Canine Heart Muscle*, Acta Mechanica Salida Sinica, Sep. 2007, vol. 20, No. 3, 189-197.

Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.

Ye et al., Six-month outcome of transapical transcatheter aortic valve implantation in the initial seven patients, European Journal of Cardio-thoracic Surgery, 2007, 16-21, 31.

Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.

Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.

Zhou et al., Thromboembolic Complications of Cardiac Radiofrequency Catheter Ablation: A Review of the Reported Incidence. Pathogenesis and Current Research Directions. Journal of Cardiovascular Electrophysiology, Apr. 1999, 611-620, vol. 10, No. 4.

Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.

A first for MiCardia's Dynoplasty, Medical Device Daily, Feb. 19, 2009, vol. 13, No. 32, 1 page.

Babaliaros et al., Emerging Applications for Transseptal Left Heart Catheterization—Old Techniques for New Procedures, Journal of the American College of Cardiology, Jun. 3, 2008, 2116-22, vol. 51, No. 22.

Bailey, et al., "The Surgical Correction of Mitral Insufficiency by the Use of Pericardia! Grafts" Dec. 1954 (pp. 551-627).

Bailey, et al., "Surgical Repair of Mitral Insufficiency" Feb. 1951 (pp. 125-137).

Bailey, et al., "Closed Intracardiac Tactile Surgery" Jul. 1952 (pp. 1-24).

Balzer et al., Real-time transesophageal three-dimensional echocardiography for guidance of percutaneous cardiac interventions: first experience, Clinical Research in Cardiology, May 29, 2008, 565-574, vol. 97, No. 9.

Benichoux, et al., "A Method of Surgical Correction of Mitral Insufficiency" 1955 (pp. 148-158).

Blalock, "A Consideration of Some of the Problems in Cardiovascular Surgery" Jun. 1951 (pp. 543-571 ).

B-Lundqvist et al., Transseptal Left Heart Catheterization: A Review of 278 Studies, Clin. Cardiel., Jan. 1986, 21-26, vol. 9.

Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.

Borrie, "Mitral Insufficiency: Experimental Circular Suture Around the Atrioventricular Ring" 1955 (pp. 687-697).

Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, 1-8-1-11.

Bryan et al., Prospective randomized comparison of Carbo Medics and St. Jude Medical bileaflet mechanical heart valve prostheses: Ten-year follow-up, The Journal of Thoracic and Cardiovascular Surgery, Mar. 2007, 614-622.e2, vol. 133, No. 3.

Burkoff, MD., Ph.D, et al., "A randomized multicenter clinical study to evaluate the safety and efficacy of the TandemHeart percutaneous ventricular assist device versus conventional therapy with intraaortic balloon pumping for treatment of cardiogenic shock," The Cardiovascular Research Foundation, accepted May 2, 2006, 8 pages.

Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.

Canadian Office Action dated Sep. 12, issued in Canadian Patent Application No. 2,627,517, 2 pages.

Carlson et al., Lead Perforation: Incidence in Registries, Pace Industry Viewpoint, Jan. 2008, 13-15, vol. 31.

Carpentier et al., Reconstructive surgery of mitral valve incompetence Ten-year appraisal, The Journal of Thoracic and Cardiovascular Surgery, Mar. 1980, 338-348, vol. 79, No. 3.

Carter, et al. "Surgical Treatment of Mitral Insufficiency" 1953 (pp. 574-583).

Office Action received in Chinese Application No. 201480045369.2, dated Sep. 1, 2016; 12 pages.

Office Action received in Chinese Application No. 201480028456.7, dated Oct. 18, 2016; 12 pages.

Office Action received in Chinese Application No. 201480028344.1, dated Nov. 15, 2016; 10 pages.

Extended European Search Report dated Oct. 7, 2016 issued in European Patent Application No. 14769641.3; 8 pages.

Extended Search Report dated Oct. 10, 2016 issued in European Application No. 14770314.4; 8 pages.

Second Office Action received in CN Application No. 201480045369.2 dated Jun. 21, 2017; 13 pages.

Notification of Transmittal of the International Search Report in International Application No. PCT/US17/31955, dated Aug. 4, 2017.

Examination Report in Australian Patent No. 2014239832, dated Nov. 27, 2017.

* cited by examiner

FIG. 14A
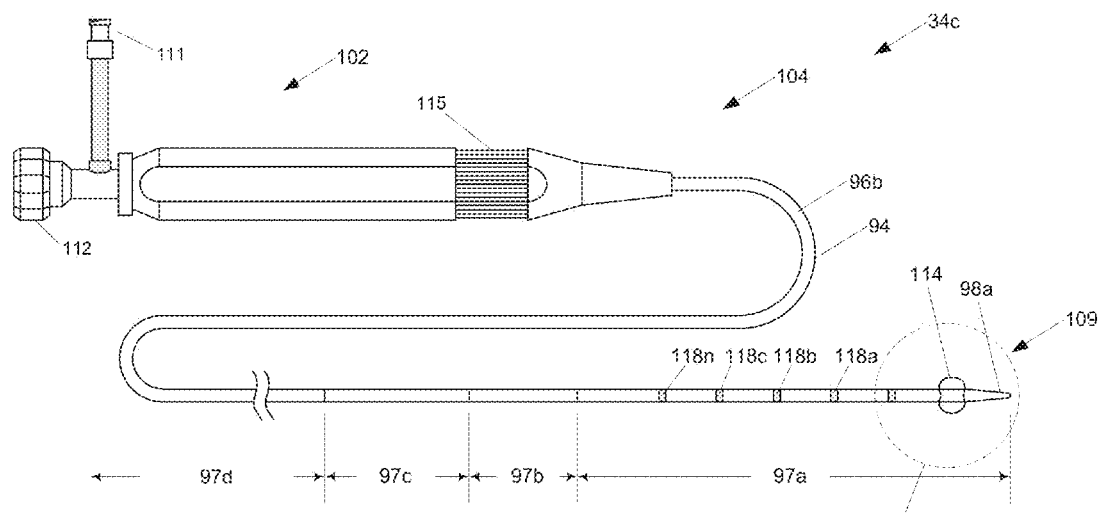
FIG. 14B
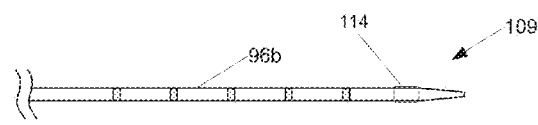
Close-up section of tip
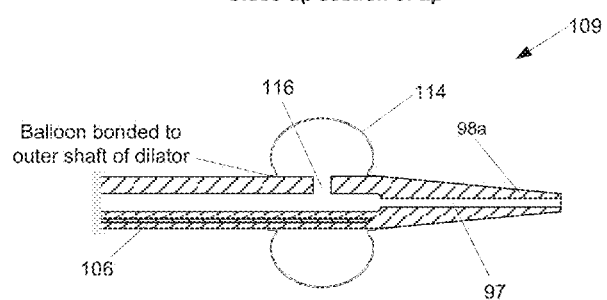
FIG. 14C

SECTION B-B

MITRAL VALVE SPACER AND SYSTEM AND METHOD FOR IMPLANTING THE SAME

CROSS-REFERENCE AND RELATED APPLICATIONS

The present application claims benefit of U.S. Provisional Patent No. 61/835,093, filed Jun. 14, 2013, the entire content of the application is hereby incorporated by reference.

FIELD OF THE APPLICATION

The present disclosure relates to the repair and/or correction of dysfunctional heart valves, and more particularly pertains to heart valve implants and systems and methods for delivery and implementation of the same.

BACKGROUND

The human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement may be carried out as an open heart procedure. The repair or replacement surgery may last in the range of about three to five hours, and may be carried out with the patient under general anesthesia. The nature of the surgical procedure requires the patient to be placed on a heart-lung machine. Because of the severity, complexity, and/or danger associated with open heart surgical procedures, corrective surgery for mitral regurgitation may not be recommended in certain patients.

SUMMARY OF THE INVENTION

Described herein is a heart valve implant and methods of delivering the same to an individual's heart. The heart valve implant is configured to be delivered to the heart transapically (i.e., through the apex of the heart) or transfemorally. The heart valve implant is configured to be implanted at least partially within the heart.

Accordingly, in one aspect, the invention is directed to a heart valve implant. The heart valve implant comprises an inflatable valve body, a shaft, an anchor assembly, and an inflation (e.g., injection) port. The inflatable valve body defines a cavity comprising a proximal end and a distal end. The shaft extends from the proximal end of the inflatable valve body and comprises a lumen in fluid communication with said cavity. The anchor assembly is attached to the shaft, proximal to the inflatable valve body. The inflation (e.g., injection) port can include one or more lumens in fluid communication with the shaft lumen.

In some aspects, the heart valve implant comprises one or more radiopaque markers. In another aspect, the heart valve implant comprises one or more radiopaque markers that are located at or near the proximal end of the inflatable valve body.

In some aspects, the inflation (e.g., injection) port comprises a pierceable septum configured to fluidly seal the inflation port. In some embodiments, the pierceable septum can be self-sealing. In a related aspect, the inflation port is substantially hollow. The pierceable septum can be formed of a variety of different materials. By way of example, in some embodiments, the pierceable septum comprises silicone. In one embodiment, the pierceable septum is liquid-tight. In some embodiments, the inflation port comprises one or more suture holes.

In some aspects, the anchor assembly comprises a passageway and one or more arms. For example, the anchor assembly can include a central opening and two opposed peripheral arms that extend outwardly from the central opening. In one aspect, the passageway is configured to receive and advance the shaft. In one aspect, each of the one or more arms defines an opening and the anchor assembly is configured to be secured to an exterior surface of an individual's heart. In one aspect, one or more sutures are placed around each of the one or more arms of the anchor assembly. The sutures can be employed to secure (e.g., fixate) the anchor assembly to an exterior surface of an individual's heart.

In some aspects, the inflatable valve body is partially inflated with an expansion medium (inflation fluid). In another aspect, the inflatable valve body is completely inflated with an expansion medium (inflation fluid). A variety of expansion media can be employed. In some embodiments, the expansion medium is a gas, a liquid or a gel. By way of example, in some embodiments, the expansion medium can be deionized water, saline, or contrast medium.

In some aspects, the shaft of the heart valve implant is attached to the distal end of the inflatable valve body. In some embodiments, the shaft of the heart valve extends partially through the inflatable valve body. In other embodiments, the shaft of the heart valve implant extends across a length of the inflatable valve body and is attached to both the proximal and distal ends of the inflatable valve body.

In some aspects, the lumen of the shaft, in fluid communication with the inflatable valve body, comprises one or more openings. The one or openings provide the fluid communication between the lumen of the shaft with the inflatable valve body.

In some embodiments, the inflatable valve body can be formed of any of material suitable for the implant described herein. The material can be able to withstand physiological conditions (e.g., the conditions in a heart). The material can also be elastic and pliably deformable.

In some embodiments, the shaft can be formed of any of material suitable for the implant described herein. The shaft can be flexible or pliably deformable so that it can bend to accommodate the delivery systems described herein. The shaft can also have sufficient rigidity as not to collapse onto itself.

In some embodiments, the anchor assembly can be formed of any of material suitable for the implant and methods described herein.

In another aspect, the invention is directed to a method of trans-apically delivering a heart valve implant within a heart. The method comprises trans-apically advancing an introducer comprising a lumen through an incision in an apex of a heart into a left ventricle, advancing said introducer through a mitral valve into a left atrium, advancing the heart valve implant through the introducer lumen into the left atrium, wherein a shaft of the heart valve implant extends from an inflatable valve body to beyond the incision in the apex, and removing the introducer from said heart, thereby delivering the valve body and at least a portion of the shaft within the heart.

In one aspect, the method of trans-apically delivering a heart valve implant comprises placing the inflatable valve body at least a portion of one or more cusps or leaflets of the heart valve may interact with, engage, and/or seal against at least a portion of the heart valve implant when the heart valve is in a closed condition. The interaction, engagement and/or sealing between at least a portion of at least one cusp or leaflet and at least a portion of the heart valve implant may reduce and/or eliminate regurgitation in a heart valve, for example, providing insufficient sealing, including only a single cusp, e.g., following removal of a diseased and/or damaged cusp, and/or having a ruptured chordae.

In some aspects of the method of trans-apically delivering a heart valve implant, the implant comprises an anchor assembly. In one embodiment, the anchor assembly comprises a passageway and one or more arms. The passageway is configured to receive the shaft and to allow advancing the shaft through the passageway. Each of the one or more arms defines an opening. In some aspects, the method further comprises advancing the anchor assembly over the shaft until the anchor assembly is at or near the apex of the heart. In one aspect, the method further comprises securing the anchor assembly to an external surface of the heart. In another aspect, the method comprises securing the anchor assembly to an external surface of the heart at or near said apex of the heart. In another aspect, securing the anchor assembly comprises suturing one or more sutures around each of the one or more arms of the anchor assembly.

In another aspect, the method further comprises securing the inflation (e.g., injection) port subdermally at or near a chest wall. In some embodiments, the subdermally-located inflation port can be employed to deliver an expansion medium (inflation fluid), (e.g., deionized water, saline, contrast medium) to the inflatable valve body. For example, the expansion medium can be placed in a syringe, and the needle can be employed to pierce through the septum. The medium can then be transferred via the hollow body of the inflation port and the shaft to the inflatable valve body.

In another aspect, the method comprises trans-apically delivering a heart valve implant within a heart, wherein the inflatable valve body comprises one or more radiopaque markers for locating the inflatable valve body within the mitral valve.

In another aspect, the method further comprises completely or partially inflating the inflatable valve body with an inflation fluid. In another aspect, wherein the step of inflating the inflatable valve body further comprises piercing a pierceable septum of the inflation port and introducing an expansion medium (inflation fluid) through the pierceable septum into the inflation port thereby inflating the inflatable valve body with the inflation fluid. In one aspect, the inflation fluid is a liquid. In another aspect, the method further comprises adjusting the amount of inflation fluid within the implant until a desired level of inflation is attained. In another aspect, the inflatable valve body interacts with all or a portion of at least one cusp or leaflet of the mitral valve. In another aspect, the inflatable valve body partially or completely restricts a flow of blood through the mitral valve in a closed position.

In another aspect, the method further comprises de-airing the implant.

In another aspect, the invention is directed to method of trans-apically delivering a heart valve implant within a heart. The implant comprises an inflatable valve body, a shaft, an anchor assembly, and an inflation port. The method comprises trans-apically advancing an introducer comprising a lumen through an incision in an apex of a heart into a left ventricle, advancing the heart valve implant through the introducer lumen into the left ventricle, wherein the inflatable valve body extends from the introducer, partially inflating the inflatable valve body, advancing said introducer and partially inflated inflatable valve body through a mitral valve into a left atrium, advancing the heart valve implant through the introducer lumen into the left atrium, removing the introducer from said heart, thereby delivering the inflatable valve body and at least a portion of the shaft within the heart.

BRIEF DESCRIPTION OF THE DRAWINGS

Features and advantages of the claimed subject matter will be apparent from the following description of embodiments consistent therewith, which the description should be considered in conjunction with the accompanying drawings.

FIG. 14A illustrates a perspective view of a yet another embodiment of a dilator consistent with the present disclosure.

FIG. 14B illustrates a perspective view of one embodiment of the dilator shown in a deflected or retracted position consistent with the present disclosure.

FIG. 14C illustrates a perspective view of one embodiment of the dilator shown in an inflated or expanded position consistent with the present disclosure.

DETAILED DESCRIPTION

Figure 1:
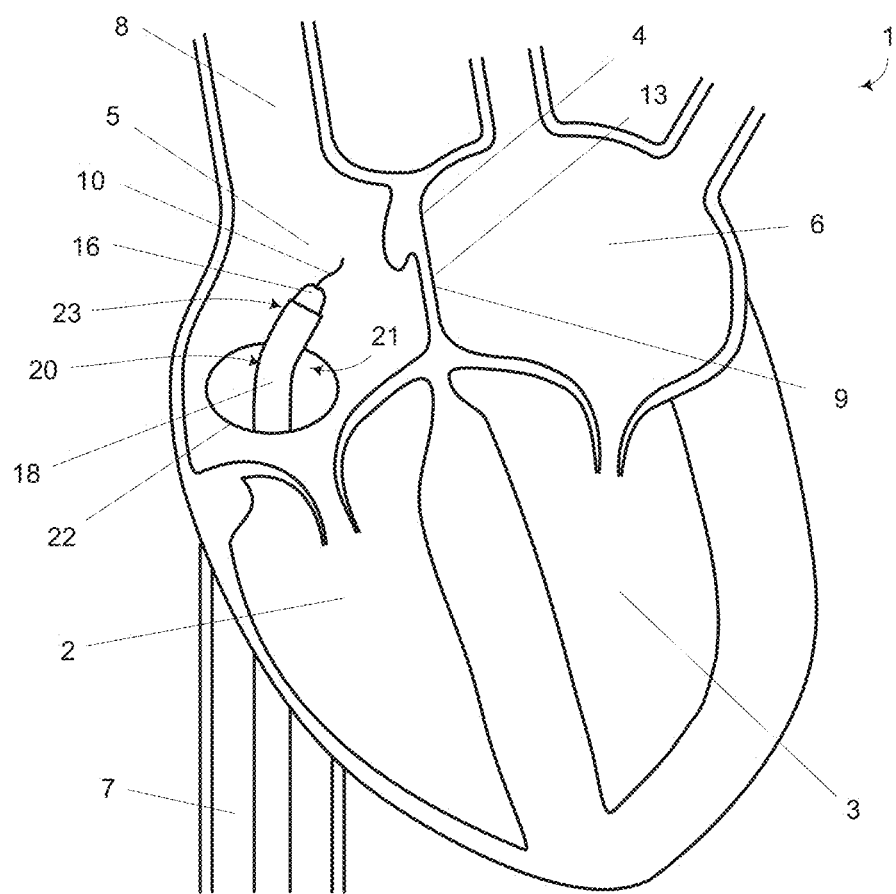
FIG. 1 illustrates a perspective view of an embodiment of a transseptal catheter in the right atrium consistent with the present disclosure.

The present disclosure relates to a system and method of implanting a heart implant. For example, the system and method according to one embodiment of the present disclosure may be used to implant a heart valve implant which may suitably be used in connection with the treatment, diagnostics and/or correction of a dysfunctional or inoperative heart valve (e.g., function mitral valve regurgitation and degenerative mitral valve regurgitation). One suitable implementation for a heart valve implant consistent with the present disclosure is the treatment of mitral valve regurgitation (mitral insufficiency or mitral incompetence). For the ease of explanation, the heart valve implant herein is described in terms of a mitral valve implant, such as may be used in treating mitral valve regurgitation as described in U.S. patent application Ser. No. 11/258,828 filed Oct. 26, 2005 and U.S. patent application Ser. No. 12/209,686 filed Sep. 12, 2008, both of which are fully incorporated herein by reference. However, a heart valve implant consistent with the present disclosure may be employed for treating, diagnosing and/or correcting other dysfunctional or inoperative heart valves, such as the heart valve implant(s) discussed herein in connection with FIG. 26

It should be understood that the technology of the present disclosure (including the implant described in connection with FIG. 26) is not limited to mitral valve implants and systems and methods of implanting mitral valve implants. Indeed, the systems and methods according to the present disclosure may be used to implant heart implants configured to be used in connection with the treatment, diagnostics and/or correction of other heart conditions. For example, and without limitation, the system and method consistent with the present disclosure may be used to implant a regurgitation implant configured to induce a controlled regurgitation in a heart valve (such as, but not limited to, a mitral heart valve), for example, in a manner that is generally consistent with advanced disease of the heart. The regurgitation implant may include a regurgitation implant as described in U.S. patent Ser. No. 11/940,724 filed Nov. 15, 2007 and U.S.

patent application Ser. No. 12/209,686 filed Sep. 12, 2008, both of which are fully incorporated herein by reference.

According to one embodiment, a heart implant consistent with the present disclosure may comprise a heart valve implant configured to interact with at least a portion of an existing heart valve to prevent and/or reduce regurgitation. For example, at least a portion of one or more cusps or leaflets of the heart valve may interact with, engage, and/or seal against at least a portion of the heart valve implant when the heart valve is in a closed condition. As used herein, "cusp" and "leaflet" refer to the same anatomic structure of a heart valve. The interaction, engagement and/or sealing between at least a portion of at least one cusp or leaflet and at least a portion of the heart valve implant may reduce and/or eliminate regurgitation in a heart valve, for example, providing insufficient sealing, including only a single cusp, e.g., following removal of a diseased and/or damaged cusp, and/or having a ruptured chordae. A heart valve implant consistent with the present disclosure may be used in connection with various additional and/or alternative defects and/or deficiencies.

For the ease of explanation, one embodiment of the system and method consistent with the present disclosure is described in terms of a system and method for implanting a mitral valve implant, such as may be used in treating mitral valve regurgitation. By way of an overview, the system and method may generally comprise placing a first guide wire into the left ventricle, replacing the first guide wire with a second (e.g., delivery) guide wire, piercing an apex the heart with the second guide wire, advancing the second guide wire such that a distal portion thereof extends to an exterior of said heart, and advancing a mitral valve implant over said guide wire through said puncture in said apex and into the left ventricle.

For example, a delivery (e.g., second) guide wire may be initially placed into the left atrium of the heart, for example, by way of transseptal puncture of the heart from the right atrium through the fossa ovalis into the left atrium. A dilator may then be advanced along the delivery guide wire to the left atrium and may be passed through the mitral valve into the left ventricle. The dilator may include a balloon which may be inflated to facilitate passing the dilator through the mitral valve without damaging the mitral valve or becoming entangled in the mitral valve chordae. A steerable catheter may then be advanced along the dilator into the left ventricle and to the apex of the heart. The delivery guide wire may then be exchanged with a third (e.g., puncturing) guide wire, which may be used to puncture through the apex of the heart. The implant may then be advanced over the third guide wire through the puncture in said heart using a trans-apical delivery procedure. Once the implant is delivered into the heart, it may be positioned and inflated in a desired manner. In some embodiments, at least one of the position and inflation of the implant may be adjustable, even after the implant is initially sited and inflated within the heart.

Referring now to FIG. 1, a cross-sectional schematic view of a portion of a four chamber heart 1 is illustrated. The outflow tracts of the right and left ventricles 2, 3 are not shown in order to better illustrate the septum 4 between the right and left atria 5, 6. As shown, the inferior vena cava (IVC) 7 and superior vena cava (SVC) 8 communicate with the right atrium 5 which is separated from the left atrium 6 by the intra-atrial septum 4. While not a limitation of the present disclosure, it is may be advantageous to make the transseptal puncture 13 through the fossa ovalis 9 since the fossa ovalis 9 is thinnest portion of the intra-atrial septum 4.

According to one embodiment consistent with the present disclosure, a first guide wire 10 may be advanced up the IVC 7 and into the right atrium 5. The first guide wire 10 may include any guide wire configured to be advanced up the IVC 7 and into the right atrium 5. Consistent with one embodiment, the first guide wire 10 may be the same as a delivery (e.g., second) guide wire discussed herein; however, the first guide wire 10 may also be separate and distinct from the delivery guide wire. Without limitation, access to the right atrium 5 may be accomplished by way of the Seldinger wire technique. For example, the right femoral vein (not shown) may be accessed with a hollow needle (not shown) and a first guide wire 10 may be inserted. The needle may be removed and a dilator 16 may be inserted over the first guide wire 10. The sheath 18 of a catheter 20 (such as, but not limited to, a Mullins catheter or the like) having a pre-bent region 21 proximate the distal tip 23 of the catheter 20 may be inserted over the dilator 16. The sheath 18, dilator 16, catheter 20 and first guide wire 10 may then be advanced up the IVC 7 through the opening 22 into the right atrium 5 as generally illustrated in FIG. 1.

Figure 2:
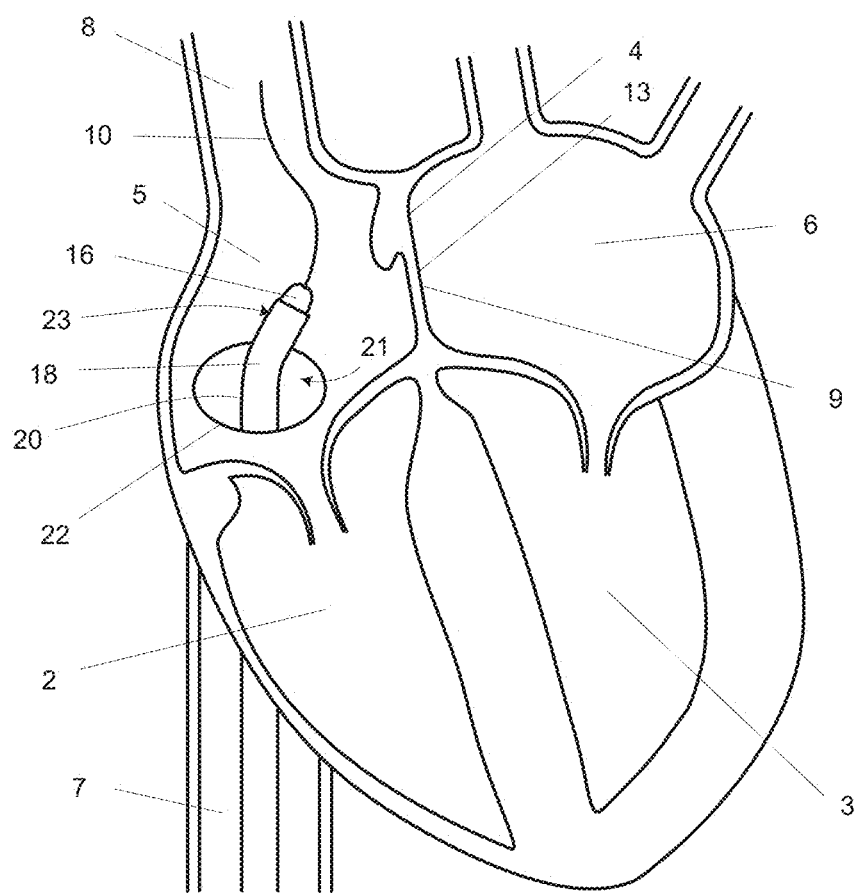
FIG. 2 illustrates a perspective view of an embodiment of a guide wire advanced into the superior vena cava consistent with the present disclosure.
Figure 3:
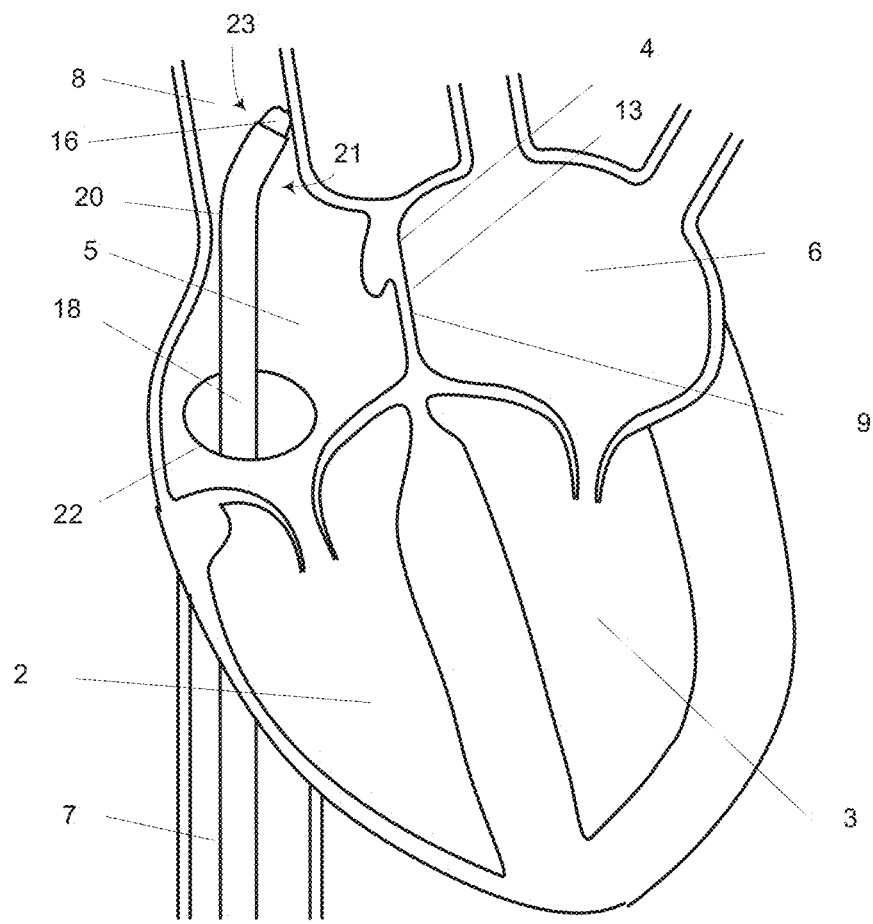
FIG. 3 illustrates a perspective view of an embodiment of a catheter advanced into the superior vena cava consistent with the present disclosure.

With the sheath 18, dilator 16, catheter 20 and first guide wire 10 in the right atrium 5, access to the left atrium 6 may be achieved by transseptal puncture 13 from the right atrium 5 through the intra-atrial septum 4. For example, at least a portion of the first guide wire 10 may be advanced out of the distal tip 23 of the dilator 16, sheath 18 and/or catheter 20 as generally shown in FIG. 2. According to an embodiment, the first guide wire 10 may be at least partially advanced into the SVC 8 as generally illustrated in FIG. 2 and the distal tip 23 of the catheter 20 may then be at least partially advanced along the first guide wire 10 into the SVC 8 as generally illustrated in FIG. 3. Because the SVC 8 is a thin-walled vein, it may be advantageous to place the first guide wire 10 in the SVC 8 and then advance the catheter 20 along the first guide wire 10 since the spring-tipped atraumatic first guide wire 10 reduces the potential for damaging the SVC 8 compared to the catheter 20 and dilator 16.

Figure 4:
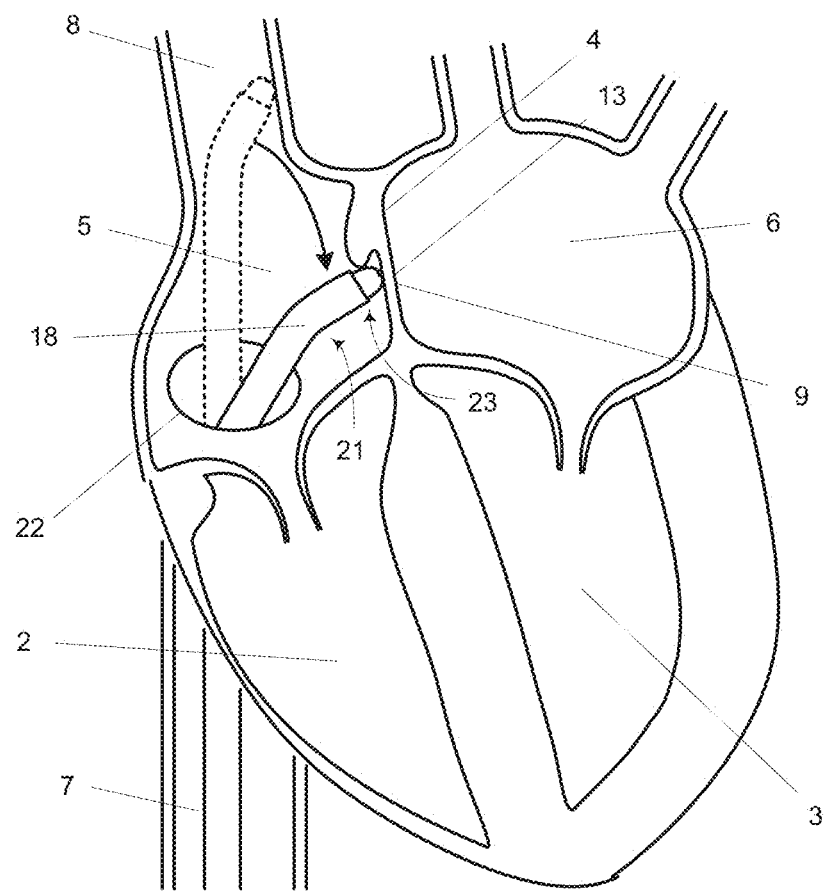
FIG. 4 illustrates a perspective view of an embodiment of a catheter tip against the fossa ovalis consistent with the present disclosure.
Figure 5:
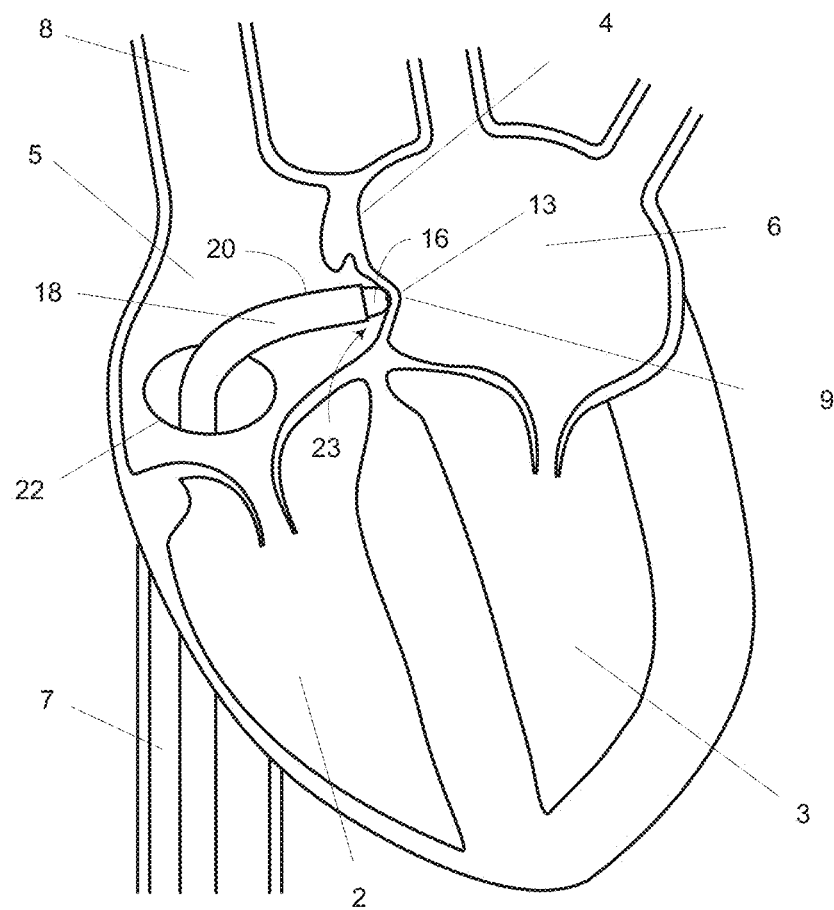
FIG. 5 illustrates a perspective view of an embodiment of a catheter tenting the fossa ovalis consistent with the present disclosure.

With the distal tip 23 at least partially received in the SVC 8, the first guide wire 10 may be retracted into the dilator 16 and the catheter 20 may be retracted (i.e., pulled downward) such that the pre-bent portion 21 of the sheath 18 facilitates guiding the distal tip 23 to the fossa ovalis 9 as generally illustrated in FIG. 4. For example, using one or more visualization techniques (such as, but not limited to, intracardiac echo (ICE), fluoroscopy, and the like), the sheath 18 may be retracted proximally, dragging the distal tip 23 along the intra-atrial septum 4 until the distal tip 23 is positioned proximate to the fossa ovalis 9. Optionally, the position of the sheath 18 relative to the fossa ovalis 9 may be confirmed by gently pushing the sheath 18 distally against the intra-atrial septum 4 to "tent" the fossa ovalis 9 as generally illustrated in FIG. 5. The "tenting" of the fossa ovalis 9 may be seen on ICE, fluoroscopy or the like.

Figure 6:
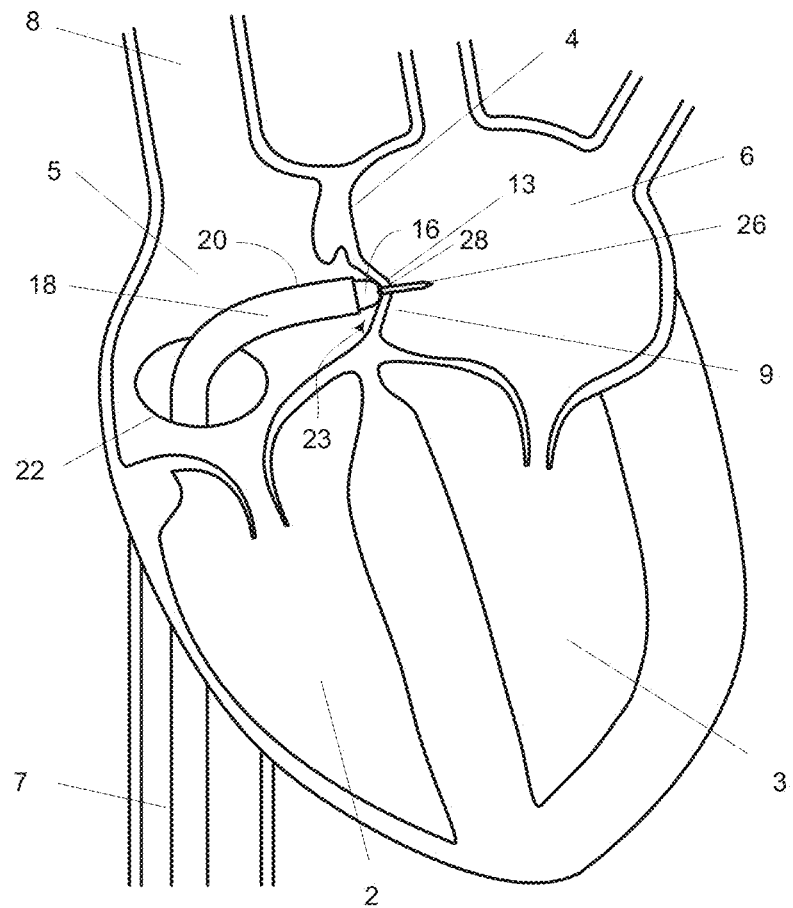
FIG. 6 illustrates a perspective view of an embodiment of a needle puncturing the fossa ovalis consistent with the present disclosure.
Figure 7:
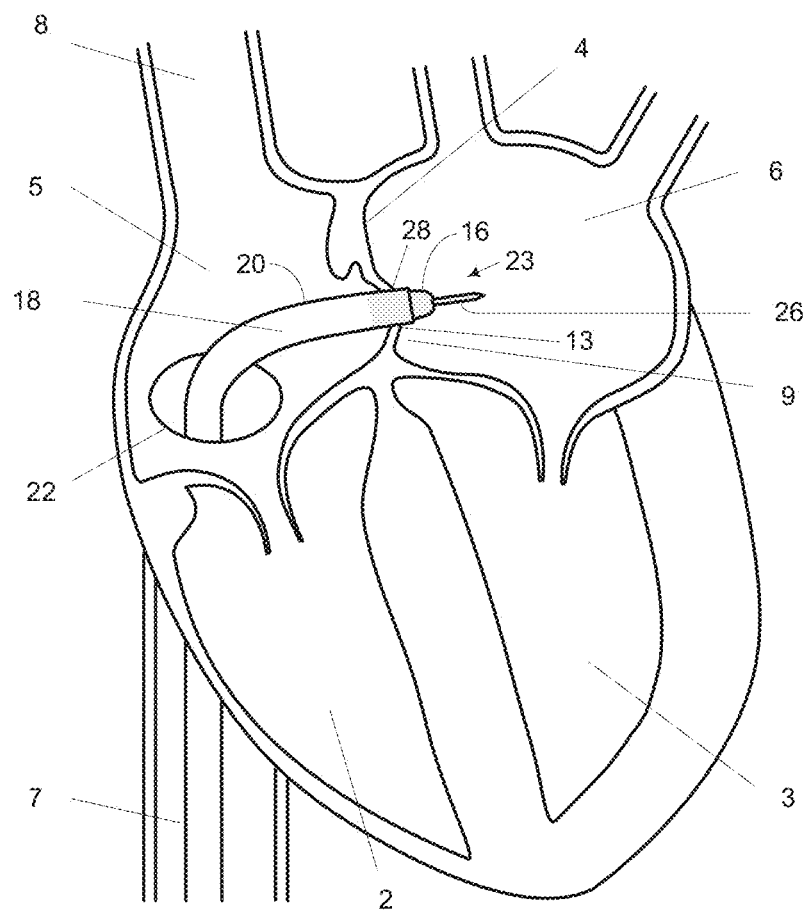
FIG. 7 illustrates a perspective view of an embodiment of a transseptal catheter punctured through the fossa ovalis consistent with the present disclosure.
Figure 8:
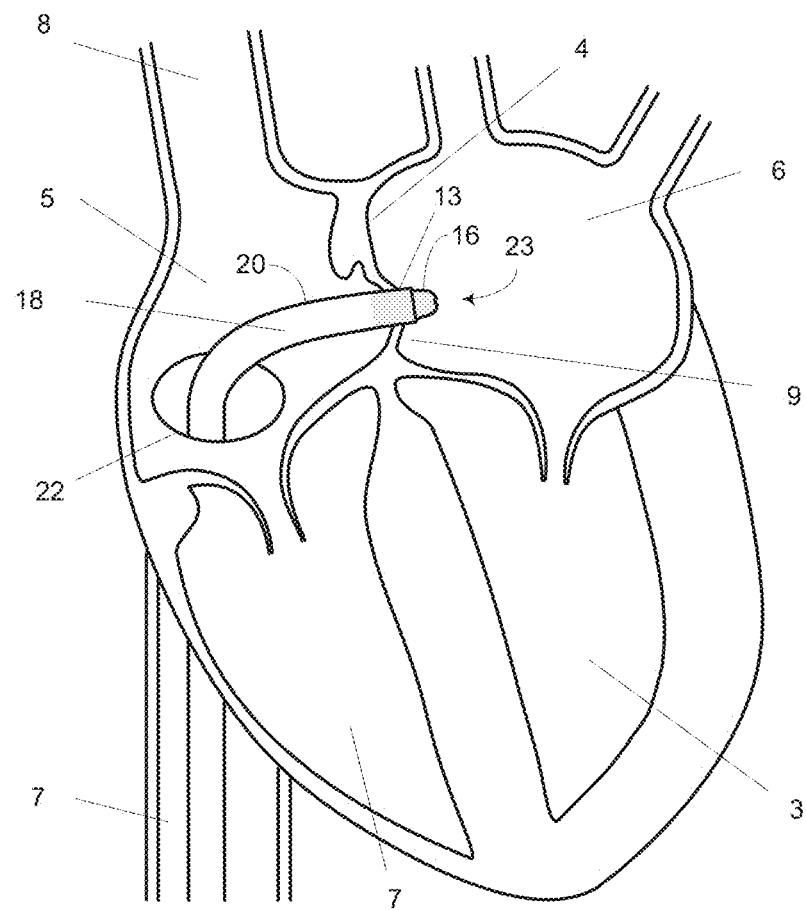
FIG. 8 illustrates a perspective view of an embodiment of a transseptal catheter punctured through the fossa ovalis with its distal tip in the left atrium with the needle removed consistent with the present disclosure.

With the distal tip 23 proximate and/or contacting the fossa ovalis 9, the first guide wire 10 may be removed from the catheter 20 and a transseptal needle 26 may be advanced through the catheter 20 towards the distal end 23 of the catheter 20 as generally shown in FIG. 6. The position of the catheter 20 may optionally be confirmed (for example, but not limited to, by "tenting") and the transseptal needle 26 may be advanced out of the distal tip 23 to form a puncture 28 through the fossa ovalis 9 and into the left atrium 6. The sheath 18, dilator 16 and catheter 20 may than be advanced through the puncture 28 of the fossa ovalis 9 and into the left atrium 6 as generally shown in FIG. 7. Once the sheath 16, dilator 28 and catheter 20 are through the fossa ovalis 9, the needle 26 may be removed from the catheter 20 as generally shown in FIG. 8.

Figure 9:
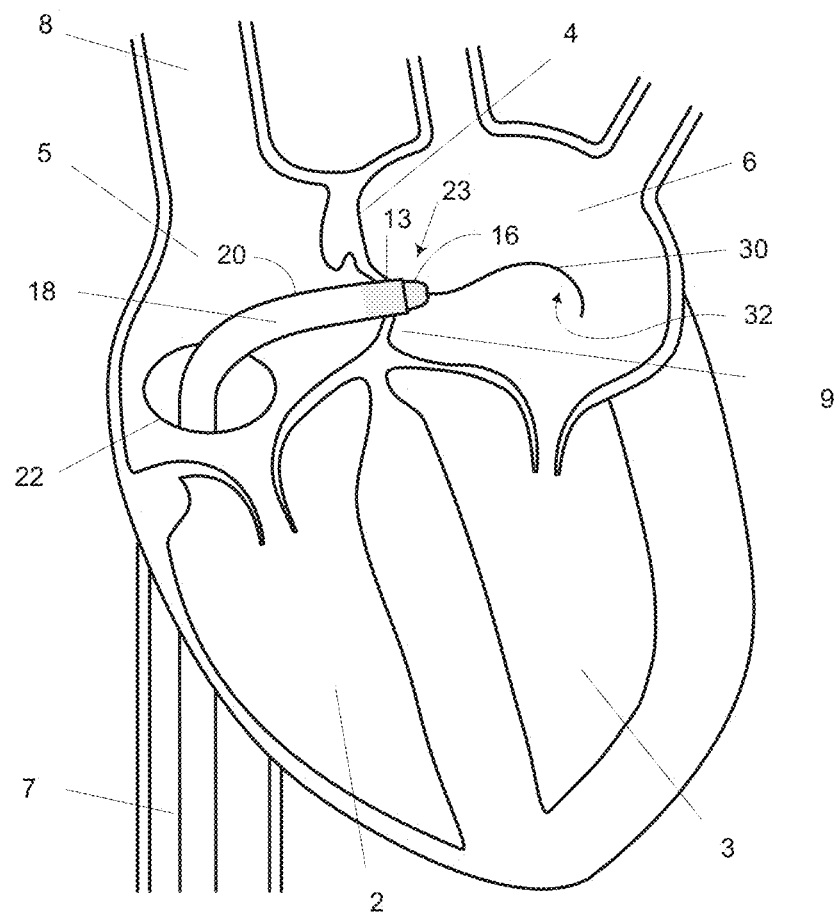
FIG. 9 illustrates a perspective view of an embodiment of a delivery guide wire advanced into the left atrium through the transseptal catheter consistent with the present disclosure.
Figure 10:
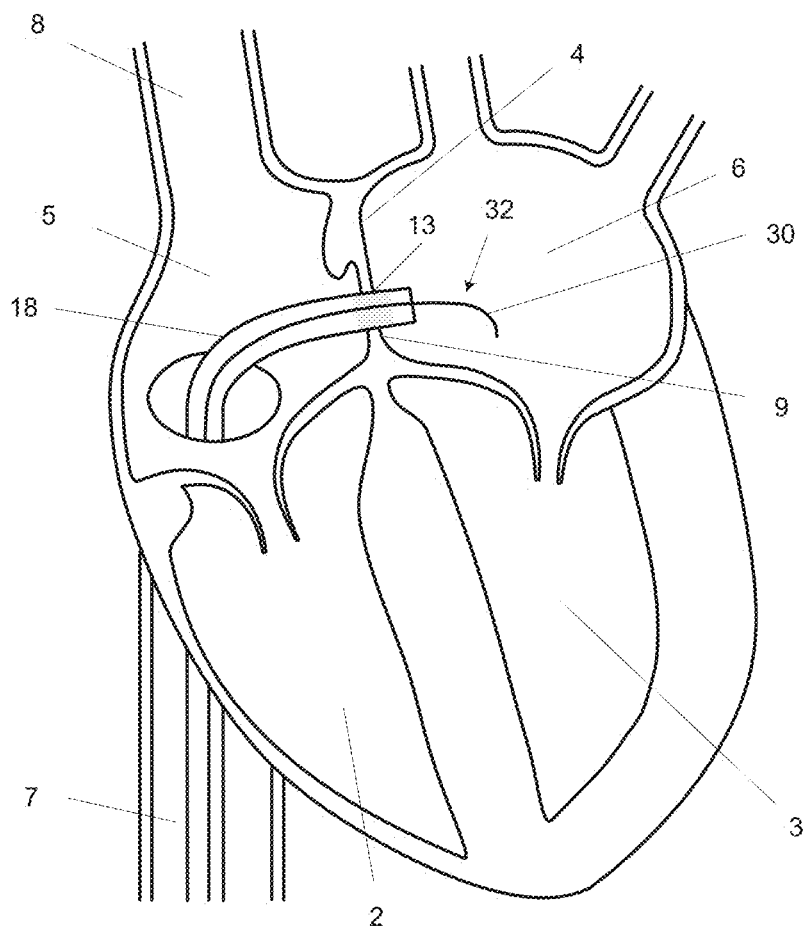
FIG. 10 illustrates a perspective view of an embodiment of a sheath and dilator removed with a delivery guide wire in the left atrium consistent with the present disclosure.

With the catheter 20 in the left atrium 6, a delivery (e.g., second) guide wire 30 may be advanced through the catheter 20 until at least a portion of the distal tip 32 of the delivery guide wire 30 extends from the distal tip 23 of the catheter 20 and into the left atrium 6 as generally illustrated in FIG. 9. Once the distal tip 32 of the delivery guide wire 30 is disposed in the left atrium 6, the dilator 16 and the sheath 18 may be removed, leaving just the delivery guide wire 30 in the left atrium 6 as generally illustrated in FIG. 10.

The delivery guide wire 30 may be used as a guide for advancing other devices into the heart 1, and ultimately, into the left ventricle 3. Accordingly to at least one embodiment, the delivery guide wire 30 may be sufficiently stiff to resist undesirable bending and/or kinking and to resist undesirable movement of the distal tip 32. For example, the delivery guide wire 30 may comprise a stiff, 0.018" diameter guide wire having a stiffness of approximately 19,900,000 psi. The stiffness of the delivery guide wire 30 was determined as follows.

When a force is applied to a long thin column, there is no movement of the column until a minimum critical buckling force is achieved, $P_{cr}$, then further buckling occurs, though the force does not increase. For a long column of uniform cross-section and length l, which buckles under a critical force, $P_{cr}$, the following formula applies:

$$P_{cr} = n\pi^3 \frac{EI}{L^2}$$

Where:
n=a constant that is equal to 4 if both ends of the column are clamped and cannot move or rotate.
E Modulus of elasticity of the material (psi)
I=Moment of inertia (in$^4$)
For a circular cross-section the moment of inertia is:

$$I = \frac{\pi d^4}{64}$$

Substituting for 1 in the first equation for $P_{cr}$ leads to:

$$P_{cr} = n\pi^3 \frac{Ed^4}{64L^2}$$

And solving for the modulus leads to:

$$E = \frac{64L^2 P_{cr}}{n\pi^3 d^4}$$

Based on the above, an 8 cm section of the delivery guide wire 30 was tested and a buckling force of 0.41 lbs. was determined. Therefore, $$E = \frac{64(3.15)^2(0.41)}{4\pi^3(0.018)^4} = 19,900,000 \; psi$$

This stiffness (modulus of elasticity) of the delivery guide wire 30 may therefore be approximately 19,900,000 psi. Of course, the delivery guide wire 30 may have a stiffness greater than or less than 19,900,000 psi.

According to at least one other embodiment, the delivery guide wire 30 may include a typical 0.018" guide wire (for example a 0.018" angled standard exchange guide wire made by Merit Medical Systems of South Jordan, Utah, Model H20STDA18260EX which was determined to have a stiffness of approximately 1,360,000 psi based on the same methodology). In either embodiment, the delivery guide wire 30 may have a diameter greater than or less than 0.018".

Figure 11:
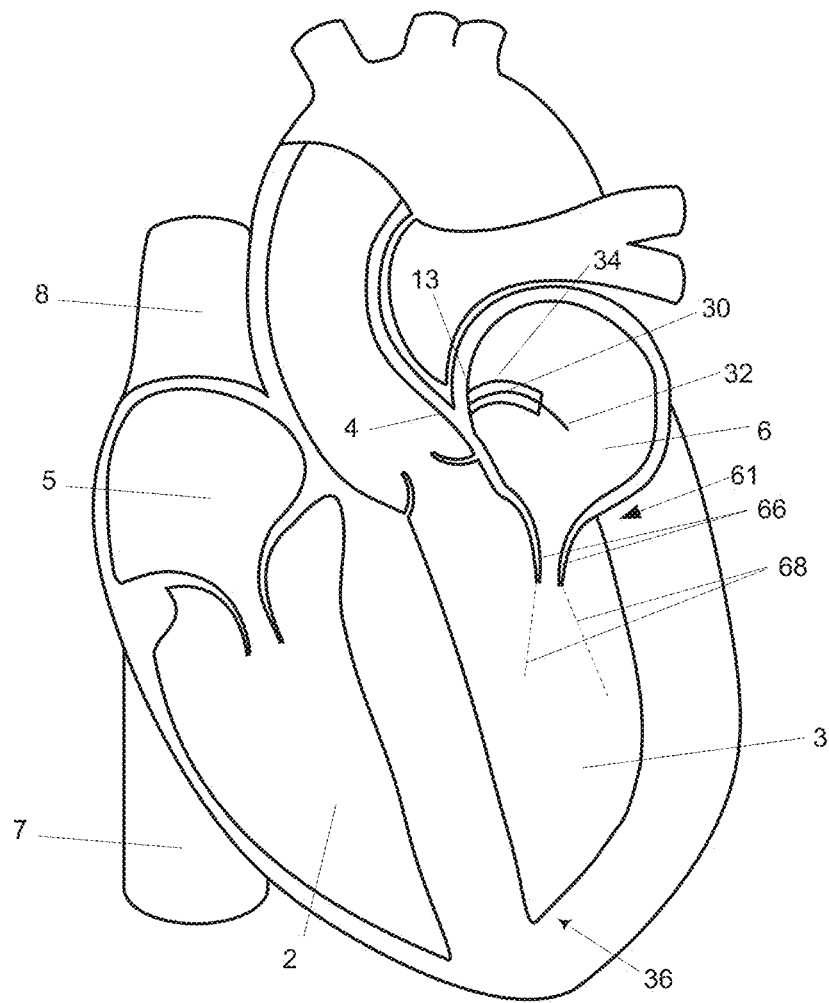
FIG. 11 illustrates a perspective view of an embodiment of a dilator advanced to the left atrium consistent with the present disclosure.

Turning now to FIG. 11, a dilator 34 may be advanced over the delivery guide wire 30 into the left atrium 6. The dilator 34 may be configured to pass through the mitral valve 61 into the left ventricle 3 without damaging the mitral valve 61 or becoming entangled in the mitral valve 61 (for example, the cusps 66, the chordae and/or papillary muscles 68 of the mitral valve 61). According to at least one embodiment, the dilator 34 of the present disclosure may be used to eliminate the delivery guide wire as disclosed in U.S. patent application Ser. No. 12/209,686 filed Sep. 12, 2008. However, it may be appreciated that the system and method disclosed in the present disclosure (and in particular the dilator 34) is not inconsistent with the system and method in U.S. patent application Ser. No. 12/209,686, and as such, the system and method disclosed in the present disclosure (including the dilator 34) may be used in conjunction with the system and method in U.S. patent application Ser. No. 12/209,686.

Figure 12:
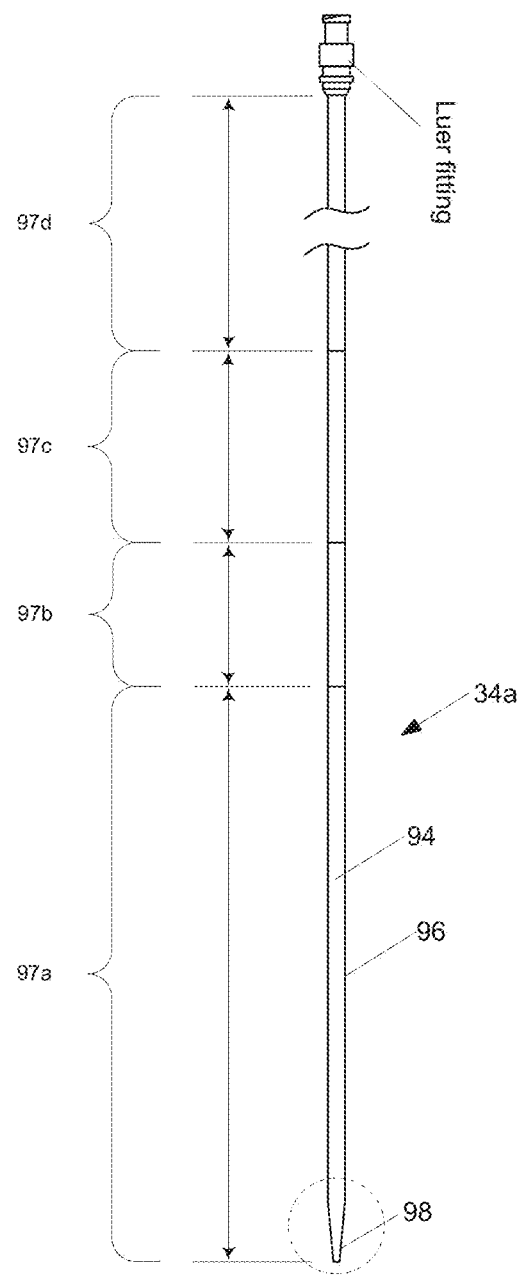
FIG. 12 illustrates a perspective view of one embodiment of a dilator consistent with the present disclosure.

One embodiment of a dilator 34a consistent with the present disclosure is generally illustrated in FIG. 12. The dilator 34a may include define at least one lumen 94 configured to receive at least a portion of the delivery guide wire 30. For example, the lumen 94 may have an internal diameter of approximately 0.038". The dilator 34a may also comprise a shaft 96 including a tapered tip region 98. The shaft 96 may comprise a plurality of segments or portions having different stiffness or hardness to produce the desired overall curvature. The shaft 96 may be formed from one or more suitable polymers such as, but not limited to, a polyether block amide. The shaft 96 may have a constant inner and/or outer diameter and may be made from different materials to provide the various stiffness or hardness. Alternatively, or in addition, the shaft 96 may have different inner and/or outer diameters and may be made from one or more materials. For example, the various stiffness or hardness of the shaft 96 may be provided by varying the thickness of the shaft 96 at the different segments or portions. The different hardness of the segments may provide differing degrees of bending stiffness to the dilator 34a which may facilitate advancing the dilator 34a into and/or out of the left ventricle 3.

As shown, the dilator 34a may comprise four different segments 97a, 97b, 97c and 97d. The first segment 97a may be disposed proximate the distal end region 98. The first segment 97a may optionally include the tapered distal tip 98 and may have a length of approximately 6 inches. The tapered distal tip 98 may be provided to facilitate advancing the tip 98 into the percutaneous puncture site in the groin as the dilator 34a is introduced over the delivery guide wire 30.

According to at least one embodiment, the first segment 97a may be formed of PEBAX™ 3533 having a durometer of 35 D. The second segment 97b may be adjacent to the first segment 97a and may have a length of approximately 1.5 inches. According to at least one embodiment, the second segment 97b may be formed of PEBAX™ 2533 having a durometer of 25 D. The third segment 97c may be adjacent to the second segment 97b and may have a length of approximately 2 inches. According to at least one embodiment, the third segment 97c may be formed of PEBAX™ 3533 having a durometer of 35 D. The forth segment 97d may be adjacent to the third segment 97c and may have a length of approximately 42.5 inches. According to at least one embodiment, the forth segment 97d may be formed of PEBAX™ 7233 having a durometer of 72 D.

It should be understood that the various lengths and hardness described above for the segments 97a-97d may be adjusted or changed depending upon the circumstances of its intended use. For example, patients with larger and/or smaller hearts may require one or more of the segments to be harder or softer. An important aspect of the segments 97a-97d is that the softest segment is the second segment 97b. Also, the second segment 97b is disposed approximately 6 inches from the tapered distal tip 98. As will be explained herein, the location of the second segment 97b may generally correspond to the of the transseptal puncture site 13 where the curvature of the dilator 34a may be greatest.

Figure 13A:
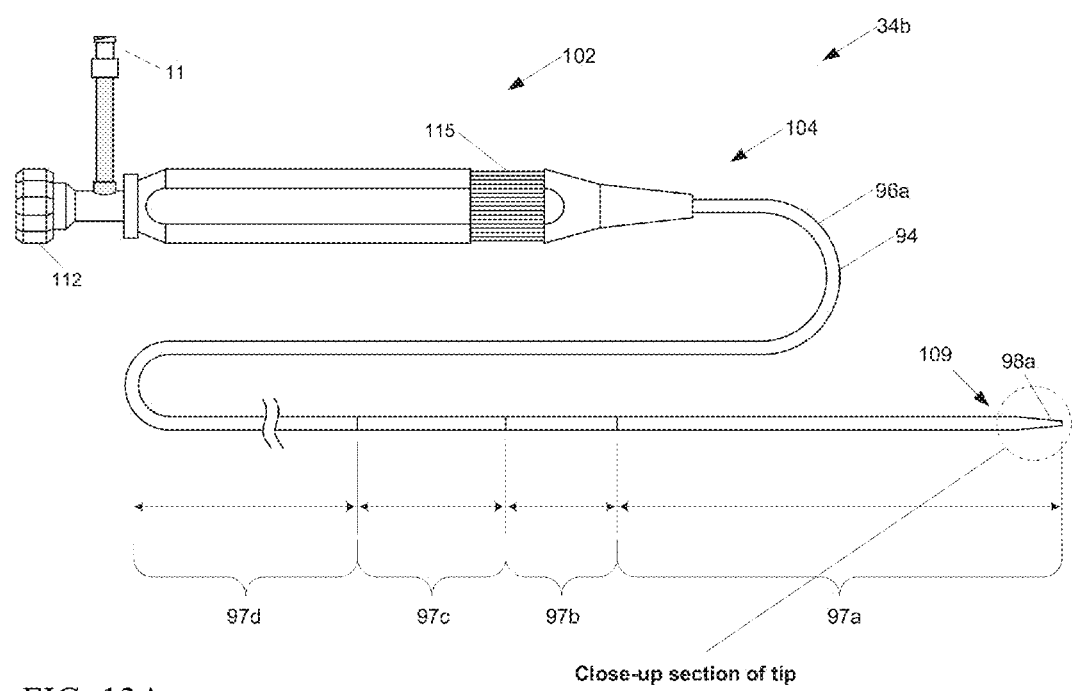
FIG. 13A illustrates a perspective view of an embodiment of a dilator consistent with the present disclosure.
Figure 13B:
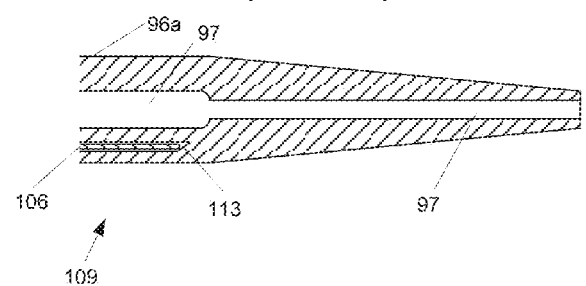
FIG. 13B illustrates a close-up of one embodiment of the tip of the dilator shown in FIG. 13A consistent with the present disclosure.

Turning now to FIGS. 13A and 13B, another embodiment of a dilator 34b consistent with the present disclosure is generally illustrated. The dilator 34b may include a deflectable tip 98a configured to allow the user to bend the distal region 109 of the dilator 34b. The deflectable tip 98a may facilitate advancement of the dilator 34b through the mitral valve 61 by allowing the user to generally aim the tip 98 towards the mitral valve 61. According to at least one embodiment, the dilator 34b may include a handle assembly 102 coupled to a proximal end 104 of the shaft 96a. The shaft 96a may include a plurality of segments, for example, the segments 97a-97d described above. One or more deflecting wires 106 may be coupled to the distal end region 109 of the shaft 96a, for example, as generally illustrated in FIG. 13B. The deflecting wire 106 may optionally be disposed in a second lumen 113 disposed along the length of the shaft 96a. Additional deflecting wires 106 (not shown) may be provided in one or more additional lumens.

The deflecting wire 106 may be coupled to the handle assembly 102 such that the distal tip 98a may be bent as desired. According to one embodiment, the handle assembly 102 may include at least one knob, slider or the like 115 coupled to the deflecting wire 106 such that actuation of the knob 115 may result in movement of the distal tip 98a. For example, the knob 115 may be coupled to the deflecting wire 106 and may pull the deflecting wire 106 generally towards the handle assembly 102 causing the distal tip 98a to bend to one side.

The handle assembly 102 may also optionally include one or more valves or fittings. For example, the handle assembly 102 may include a fitting 111 (such as, but not limited to, a Luer lock fitting or the like) configured to allow the lumen 97 to be flushed. The handle assembly 102 may also optionally include a valve 112 (such as, but not limited to, a hemostasis valve) configured to seal with the delivery guide wire 30 (not shown).

The lumen 97 may have various diameters along the length of the shaft 96a. For example, the lumen 97 may have a smaller diameter proximate the distal tip 98a compared to the remainder of the shaft 96a. The lumen 97 proximate the tip 98a may be slightly larger than the diameter of the delivery guide wire 30 (for example, but not limited to, slightly larger than 0.018") such that the dilator 34a tracks well over the delivery guide wire 30. The remainder of the lumen 97 may have a larger diameter configured to reduce drag as the dilator 34a is advanced over the delivery guide wire 30. Lumen 97 may also have a diameter sufficient to accommodate a puncturing (e.g., third) guide wire, discussed later below.

Turning now to FIGS. 14A-14C, yet another embodiment of a dilator 34c consistent with the present disclosure is generally illustrated. The dilator 34c may comprise an expandable device 114 (such as, but not limited to a balloon or the like) configured to facilitate advancement of the dilator 34c through the mitral valve 61 without damaging the mitral valve 61 or becoming entangled in the mitral valve 61 (for example, the cusps 66, the chordae and/or papillary muscles 68 of the mitral valve 61). The expanding portion 114 may be disposed proximate the distal end region 109 of the shaft 96b, for example, substantially adjacent to the tapered tip 98a. The expanding portion 114 may be fluidly coupled to an expansion medium (inflation fluid) such as, but not limited to, a gas and/or liquid which may expand and/or enlarge the expanding portion 114 from the deflated or refracted position as generally illustrated in FIG. 14B to the inflated or expanded position as generally illustrated in FIG. 14A. According to at least one embodiment, the expanding medium may include carbon dioxide CO2 gas and/or saline. Optionally, contrast media may be introduced into the expanding portion 114 to allow the expanding portion 114 to be more easily visually located using fluoroscopy or the like. The contrast media may coat the inside surface of the expanding portion 114.

The expanding medium may be introduced through a fitting 111. According to at least one embodiment, the expanding medium may be coupled to the expanding portion 114 by way of the lumen 116 as generally illustrated in FIG. 14C. As may be appreciated, the delivery guide wire 30 and/or a puncturing guide wire may be received in the lumen 97 when the dilator 34c is expanded or deflated. The expanding medium may be coupled to the expanding portion 114 by way of a separate passageway (i.e., a passageway different from the lumen 97 configured to receive the delivery guide wire 30). This passageway may be the same lumen as the deflecting (e.g., steering) wire 106 is housed in, provided there is enough room for the expansion medium to pass around the steering wire.

The expanding portion 114 may include a resiliently expandable/collapsible material such as, but not limited to, silicone, Yulex™ or the like which may be selectively collapsed and/or expanded. The expanding portion 114 may be bonded to the shaft 96b of the dilator 34c and may include one or more passageways, aperture or lumen 116 fluidly coupled to the lumen 97 to allow the expansion medium (inflation fluid) to expand/collapse the expanding portion 114. The diameter of the expanding portion 114 should be small enough in the first or retracted/collapsed position to be advanced over the delivery guide wire 30 to the left atrium 6 and large enough when in the second or expanded/inflated position to be advanced through the cusps 66 and chordae 68 of the mitral valve 61 to reduce the potential of damaging the heart 1 and/or getting entangled within the mitral valve 61. For example, the shaft 97 may have an outer diameter of approximately 0.062" (e.g., a 5 Fr) and a length of approximately 110 cm or greater. The expanding portion 114 may diameter of approximately 0.100" in the first position and a diameter of approximately 15 mm to approximately 20 mm cm in the second position with a length of approximately 8 to approximately 10 mm.

The dilator 34c may optionally include a deflectable tip 98a configured to allow the user to bend the distal region 109 of the dilator 34b as generally described herein. The dilator 34c may also optionally include one or more radiopaque markers 118a-118n, for example, disposed about the distal end region 109. The position markers 118a-118n may be spaced evenly along the shaft 97 (such as, but not limited to, approximately 2 cm intervals from the distal tip 98a) and may be used to verify the position of the dilator 34c and/or for sizing the implant to be delivered.

While various embodiments of the dilator 34 consistent with the present disclosure have been described herein, it should be understood that one or more features of any of the various embodiments may be combined with any other embodiment. The dilator 34 consistent with the present disclosure may have an overall length (i.e., from the distal tip 98 to the handle assembly 102 of approximately 145 cm or less. However, the length and/or the diameter of the dilator 34 may depend upon the introduction site as well as the intended patient's physiology.

Figure 15:
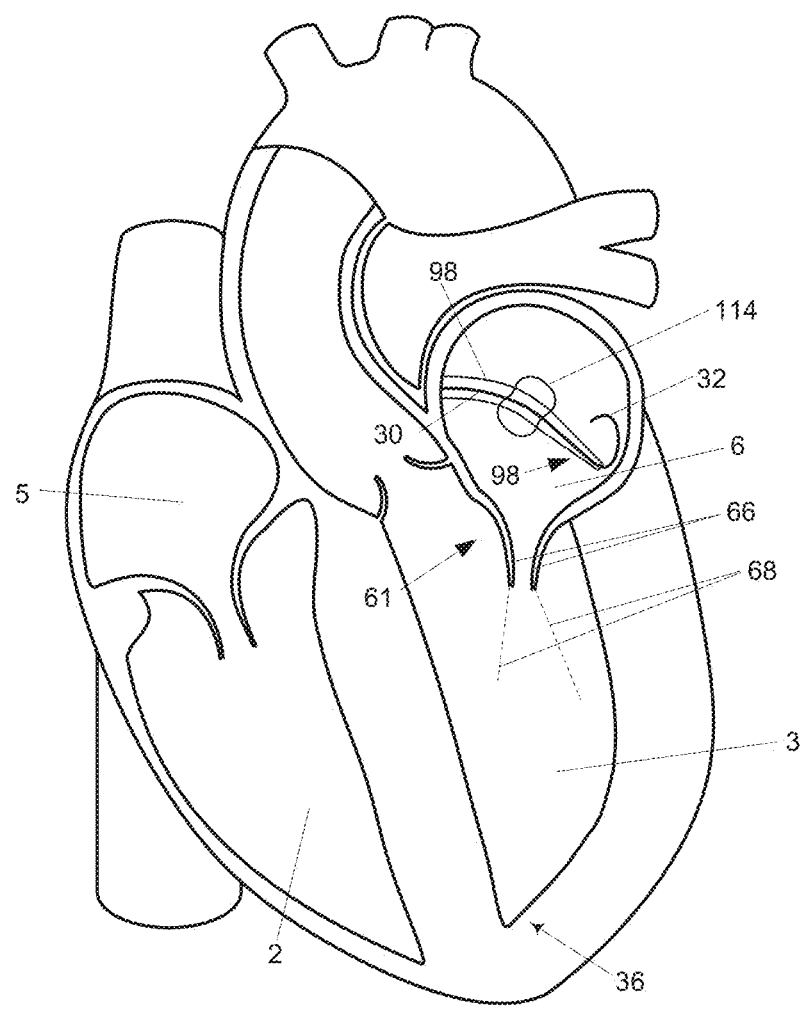
FIG. 15 illustrates a perspective view of a dilator in the inflated or expanded position located in the left atrium consistent with the present disclosure.
Figure 16:
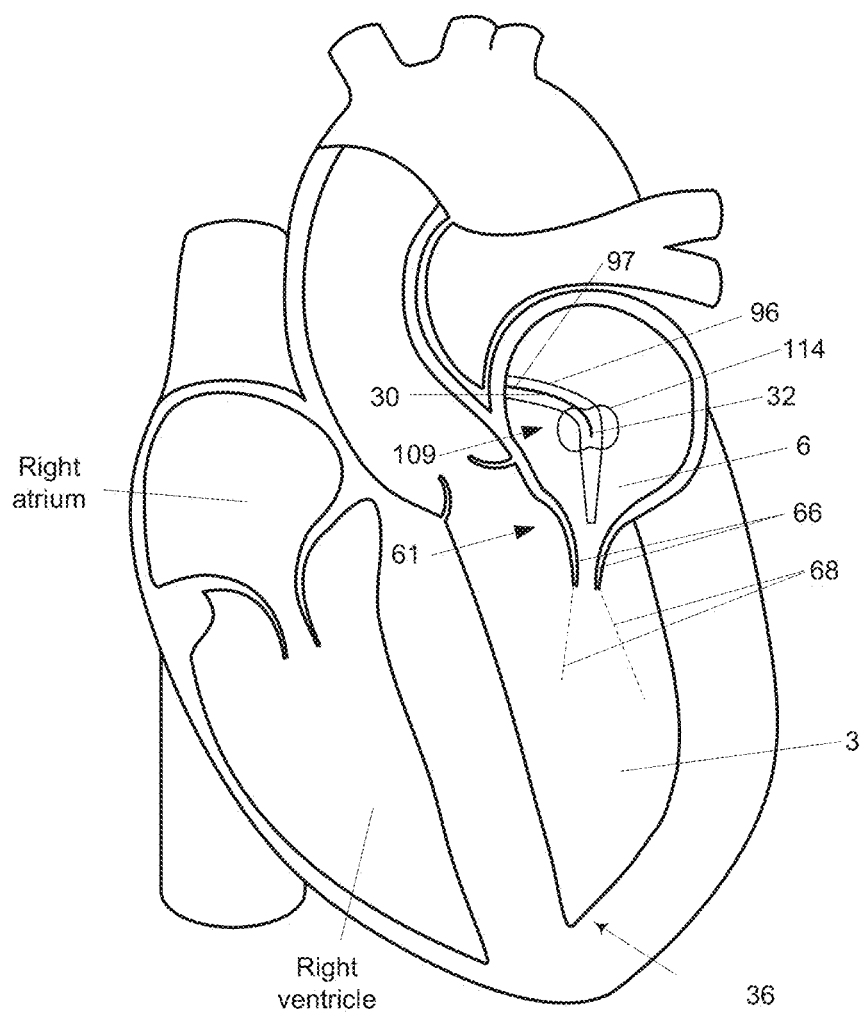
FIG. 16 illustrates a perspective view of a dilator in the inflated or expanded position located in the left atrium prior to passing through the mitral valve consistent with the present disclosure.

Turning now to FIG. 15, the dilator 34 may be advanced over the delivery guide wire 30 proximate to the tip 32 of the delivery guide wire 30. The tip 32 may still extend beyond the tip 98 of the dilator 34 to protect the atrial wall from perforation. According to one embodiment, the expanding portion 114 may be expanded as generally illustrated. The dilator 34 may aimed generally towards the mitral valve 61 as generally illustrated in FIG. 16. For example, the tip 98 may be bent or curved by actuating one or more knobs or the like (not shown) to move one or more deflecting wires as discussed herein. The tip 32 of the delivery guide wire 30 may optionally be refracted into the lumen 97 of the dilator 34 to increase the flexibility of the distal tip region 109. The curvature of the dilator 34 may be confirmed using fluoroscopic and/or echo guidance techniques or the like. For example, the contrast media and/or the radiopaque markers may be used.

Figure 17:
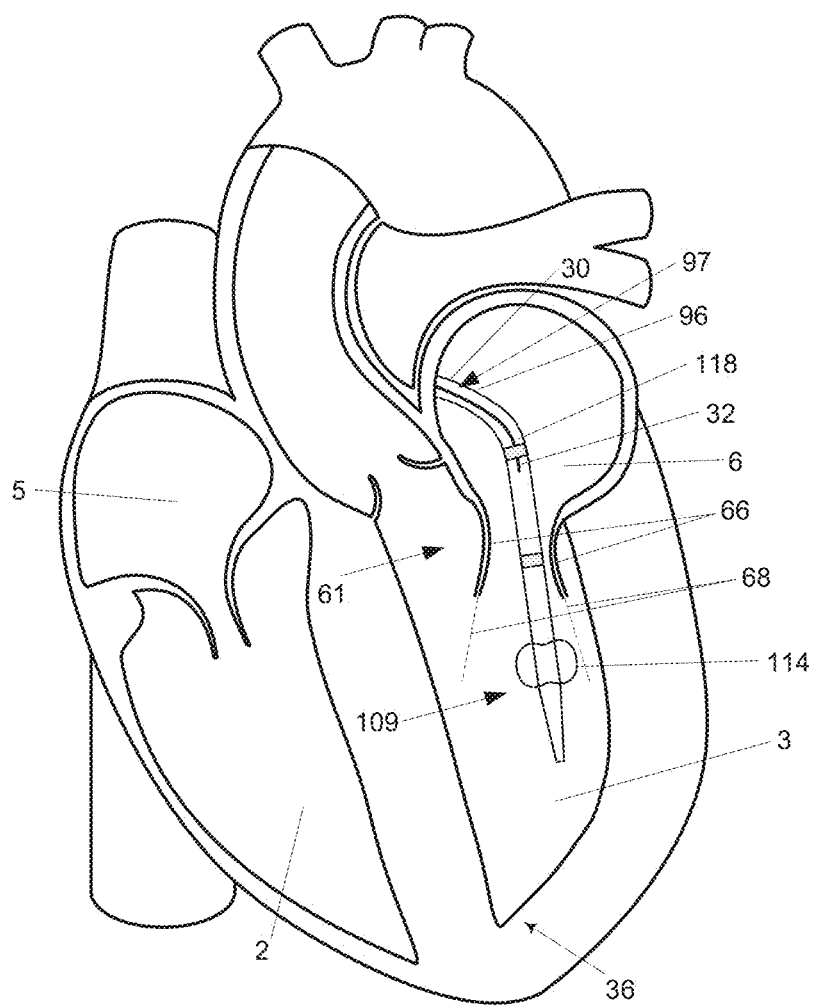
FIG. 17 illustrates a perspective view of a dilator located in the left ventricle consistent with the present disclosure.

Turning now to FIG. 17, with the dilator 34 aimed at the mitral valve 61 and the expanding portion 114 inflated, the distal end region 109 of the dilator 34 may be advanced through the mitral valve 61. It should be understood that the dilator 34 may be advanced through the mitral valve without either the deflectable tip 98 and/or the expandable portion 114; however, the use of one or more of the deflectable tip 98 and/or the expandable portion 114 may reduce the potential of damaging the heart 1 and/or getting entangled within the mitral valve 61. The second segment 97b of the shaft 96 may generally correspond to the location of the bend or curve of the dilator 34 proximate the transseptal puncture site 13. As may be appreciated, the necessary curvature of the dilator 34 between the transseptal puncture site 13 and the left ventricle 3 is relatively sharp.

The tip 32 of the delivery guide wire 30 may be still located inside the lumen 97 of the dilator 34 back in the left atrium 6 generally where it was located in FIG. 16. The dilator 34 may not yet be aimed or directed at the intended implantation site (e.g., the apex 36 of the heart) at this point. Instead, it may only be important that the distal end region 109 of the dilator 34 is through the mitral valve 61 without damaging and/or entangling the cusps 66 and the chordae/papillary muscles 68.

Figure 18:
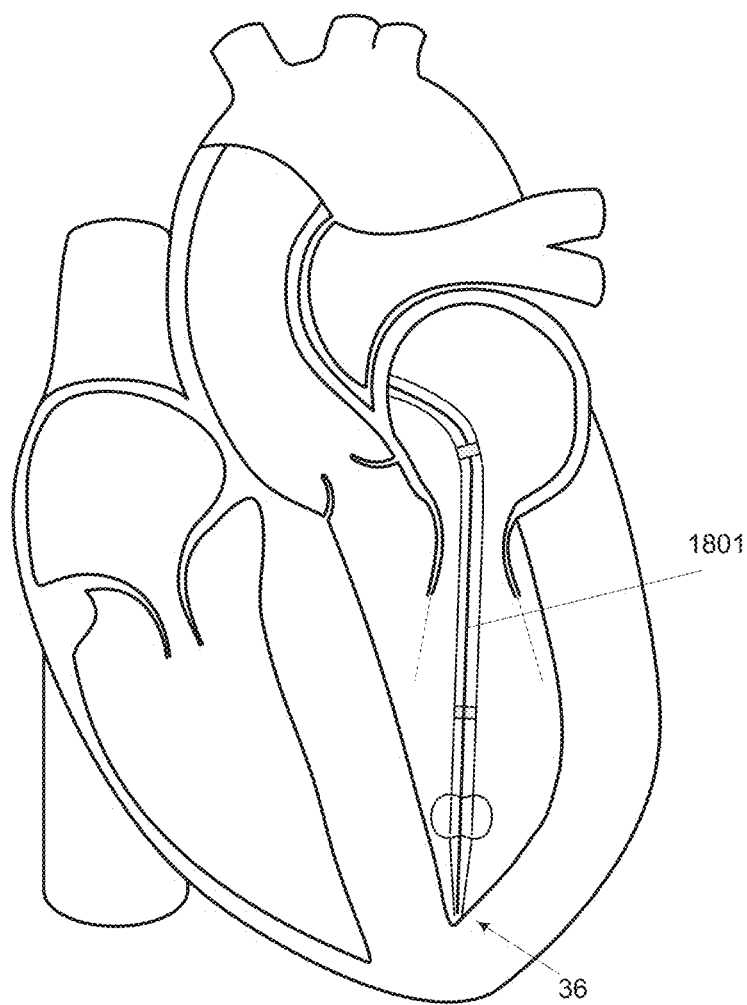
FIG. 18 illustrates a perspective view of an embodiment of a dilator advanced to an apex of the left ventricle.

Turning now to FIG. 18, dilator 34 may be aimed at and extended to an intended implantation site (in this case, apex 36) within the heart such that its distal end 109 is proximate to the intended implantation site, in this case apex 36. Before or after dialator 34 is so positioned, delivery guide wire 30 may be retracted and exchanged for a third (e.g., puncturing) guide wire 1801. As will be discussed in detail below, third guide wire 1801 may generally function to extend through a puncture at an intended implantation site of a heart, and may serve as a guide wire for the delivery of a valve implant using a trans-apical delivery procedure, e.g., through a thoracotomy or incision in the torso of a patient.

In this regard, third guide wire 1801 may in some embodiments be configured to pierce a heart at an intended implantation site, e.g., apex 36 of FIG. 18. Thus for example third guide wire 1801 may be configured to include relatively sharp distal tip (e.g. a trocar tip) that may enable third guide wire 1801 to pierce the heart when it is urged against and pushed through an intended implantation site such as apex 36. Alternatively or additionally, the distal tip of third guide wire 1801 may be threaded or otherwise configured to enable third guide wire to bore through an intended implantation site when it is urged and twisted against said implantation site. In any case, third guide wire 1801 may have a stiffness that is sufficient to enable it to be pushed and/or threaded through an intended implantation site of a heart, e.g., apex 36.

Figure 19:
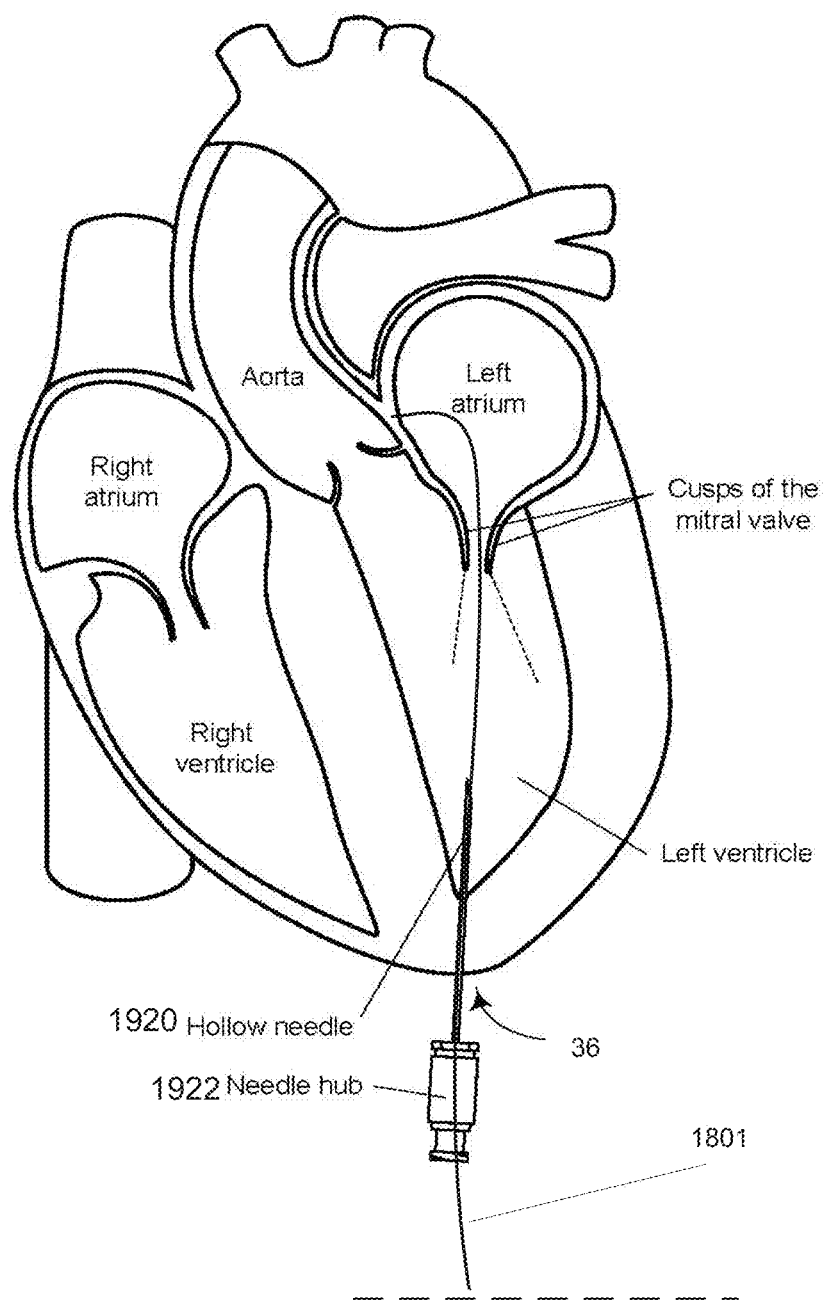
FIG. 19 illustrates a needle inserted through the apex into the left ventricle over a guide wire consistent with the present disclosure.

After third guide wire 1801 has pierced the heart, a distal end thereof may extend outside of said heart and into surrounding tissue such as the pericardium, or even into the pericardial space. At this point or upon further distal urging, third guide wire 1801 may be manipulated (e.g., grasped) and pulled until the distal end thereof may extend a significant distance outside of said heart, and potentially outside of the body of a patient. For example, through a thoracotomy or other incision, a surgeon may insert one or more instruments (e.g., graspers) into the torso of the patient to grab or otherwise manipulate a distal portion of the third guide wire 1801 such that it is pulled or otherwise advanced further outside of the heart. At that point, a hollow needle 1920 and needle hub 1922 and/or other elements may be advanced over the third guide wire 1801, as generally shown in FIG. 19.

Alternatively or additionally, a hollow needle 1920 (which may be coupled to a needle hub 1922) may be positioned proximal to an apex 36 at an exterior of the heart and aligned with a distal tip of third guide wire 1801, e.g., using fluoroscopy or another imaging technique. To facilitate alignment of hollow needle 1920 with the distal tip of third guide wire 1801, hollow needle 1920 and third guide wire 1801 may be include one or more radiopaque or other visualization markers. In embodiments, alignment of hollow needle 1920 and the distal tip of third guide wire 1801 may be considered achieved if a lumen of hollow needle 1920 and the distal tip of third guide wire 1801 are pointed at generally opposing sides of an intended implantation site of the heart. For example, when the implantation site is apex 36, alignment of hollow needle 1920 and the distal tip of third guide wire 1801 may involve aiming the distal tip of third guide wire 1801 at first portion of said apex 36 internal to said left ventricle, and aiming a distal tip (not labeled) of said hollow needle at a second portion of said apex 36 that is external to the heart.

Positioning of hollow needle 1920 as discussed above may be achieved for example by inserting the hollow needle 1920 through a thoracotomy or other incision, and maneuvering hollow needle 1920 to the correct location. For example, hollow needle 1920 may be gently maneuvered so that it pierces the pericardial sack (not shown) 1 of the heart. Using visualization means (e.g., fluoroscopy), hollow needle 1920 may be aimed at the second portion of the intended implantation site external to the heart and advanced proximate to said second portion. In some embodiments, hollow needle 1920 may be exchanged for a biopsy needle (not shown) including a biopsy lumen, wherein the biopsy needle may be advanced over a fourth guide wire (not shown)

which may be inserted to confirm the position of the hollow needle 1920. If used, the biopsy needle may remove tissue, e.g., from the pericardium, so as to facilitate the insertion of other components through the pericardium and/or other tissues surrounding the heart.

Once the distal tip of third guide wire 1801 and the hollow needle 1920 (or biopsy need) are aligned, third guide wire 1801 may be advanced through the intended implantation site (e.g., apex 36) and into the lumen of hollow needle 1920. Alternatively or additionally, hollow needle 1920 may be advanced through the intended implantation site (e.g., apex 36) and into left ventricle 3. Simultaneously or subsequently, third guide wire 1801 may be captured within a lumen of hollow needle 1920, as generally illustrated in FIG. 19.

Figure 20:
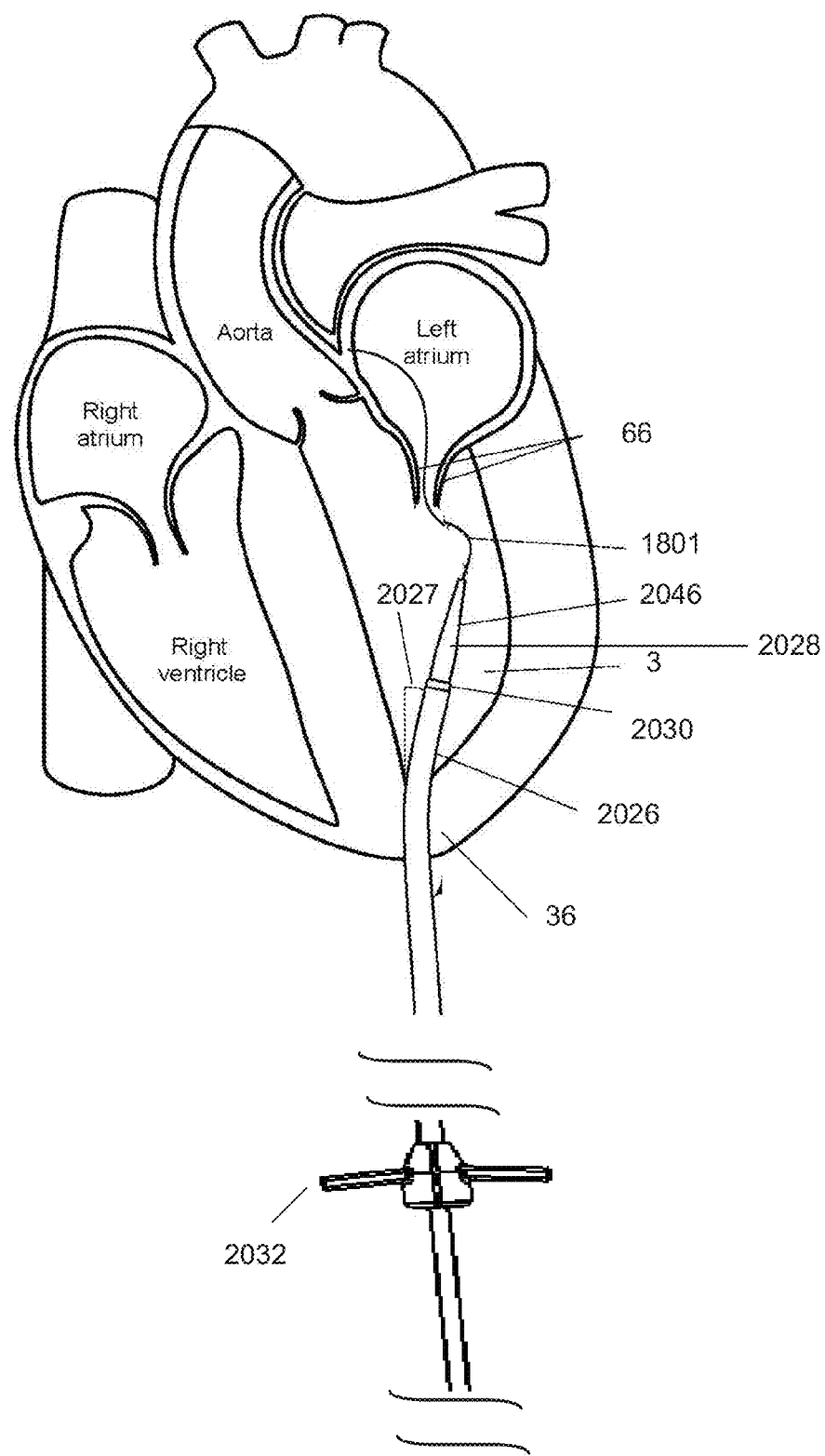
FIG. 20 illustrates an introducer and a dilator being inserted into the left ventricle over a guide wire consistent with the present disclosure.

In any case, third guide wire 1801 may be pushed or otherwise advanced through hollow needle 1820, needle hub 1822, and into the pericardium and/or pericardial space external to the heart. A distal portion of the third guide wire 1801 may then be pulled or otherwise manipulated until it extends a substantial distance outside the heart, and potentially to an exterior of a patient. At that point, hollow needle 1920 may be removed from the heart, leaving third guide wire 1801 remaining in the left ventricle 3 and extending through the intended implantation site (e.g., apex 36) and into a region external to the heart (and potentially to a patient). The third guide wire 1801 may then be used as a pathway for advancing other instruments and devices into the heart. For example, an introducer 2026 and/or dilator 2028 may be advanced along third guide wire 1801 into the left ventricle 3 as generally illustrated in FIG. 20.

The distal end 2030 of the shaft of the introducer 2026 may be beveled to aid in passing the introducer 2026 through the puncture in the apex 36. The introducer 2026 may also feature a predefined bend 2027. The predefined bend 2027 may be formed in the introducer 2026 during the manufacturing of the introducer 2026 and may be configured to facilitate alignment of the distal end 2030 of the introducer 2026 with the mitral valve 61. Without the bend 2027 (e.g., if the introducer was linear), it may be difficult to align the tip 2030 of the introducer 2026 with the mitral valve 61, between the two papillary muscles, and into the outflow tract of the mitral valve 61. While the bend 2027 does not appear to be perfectly aligned with the mitral valve 61 in FIG. 20, this is due (in part) to the three-dimensional path which is not readily shown in two-dimensional drawings. The bend 2027 may be disposed at an angle of approximately 20-40 degrees, for example 30 degrees, from the longitudinal axis of the main portion of the introducer 2026 extending outwardly from the incision in the apex 36.

The introducer 2026 may optionally include a splitter (also referred to as the introducer hub) 2032 configured to longitudinally split the shaft of the introducer 2026 such that the introducer 2026 forms a split catheter which can be easily removed while allowing an object within the lumen of the introducer 2026 (e.g., the third guide wire 1801 and/or a portion of an implant loaded in the introducer) to remain within the lumen of the introducer 2026. The splitter 2032 may include a seal configured to allow another device and/or lumen to be selectively and removably sealed and/or advanced through to the splitter 2032 and into the lumen of the introducer 2026.

For example, the splitter 2032 (introducer hub) may include at least two parts, namely, an outer shell made of a polymer that has been molded in such a way as to provide a preferential and controlled break-away seam, and the inner seal made of silicone rubber also with a molded break-away seam. The outer shell and silicone seal are mechanically connected so that the break-away seams are both positioned along the same axis as the shaft/lumen of the introducer 2026. The splitter 2032 (introducer hub) is mechanically connected to the proximal end of the introducer's tubular shaft. When the "handles" of the outer shell of the splitter 2032 (introducer hub) are actuated in opposite directions, with sufficient force, rotating away from the axis of the introducer 2026 toward the distal end of the introducer 2026, preferential break-away seams of the outer shell and of the inner seal of the splitter 2032 (introducer hub) may separate and propagate a tear in the wall of the tube of the introducer 2026. Continuing to further separate the handles of the splitter 2032 (introducer hub) in turn may continue to advance the tear in the tube of the introducer 2026. A user may thus continue to separate the handles to tear the tube until the tear reaches a distal end of the tube and complete axial separation of the introducer 26 results.

Figure 21:
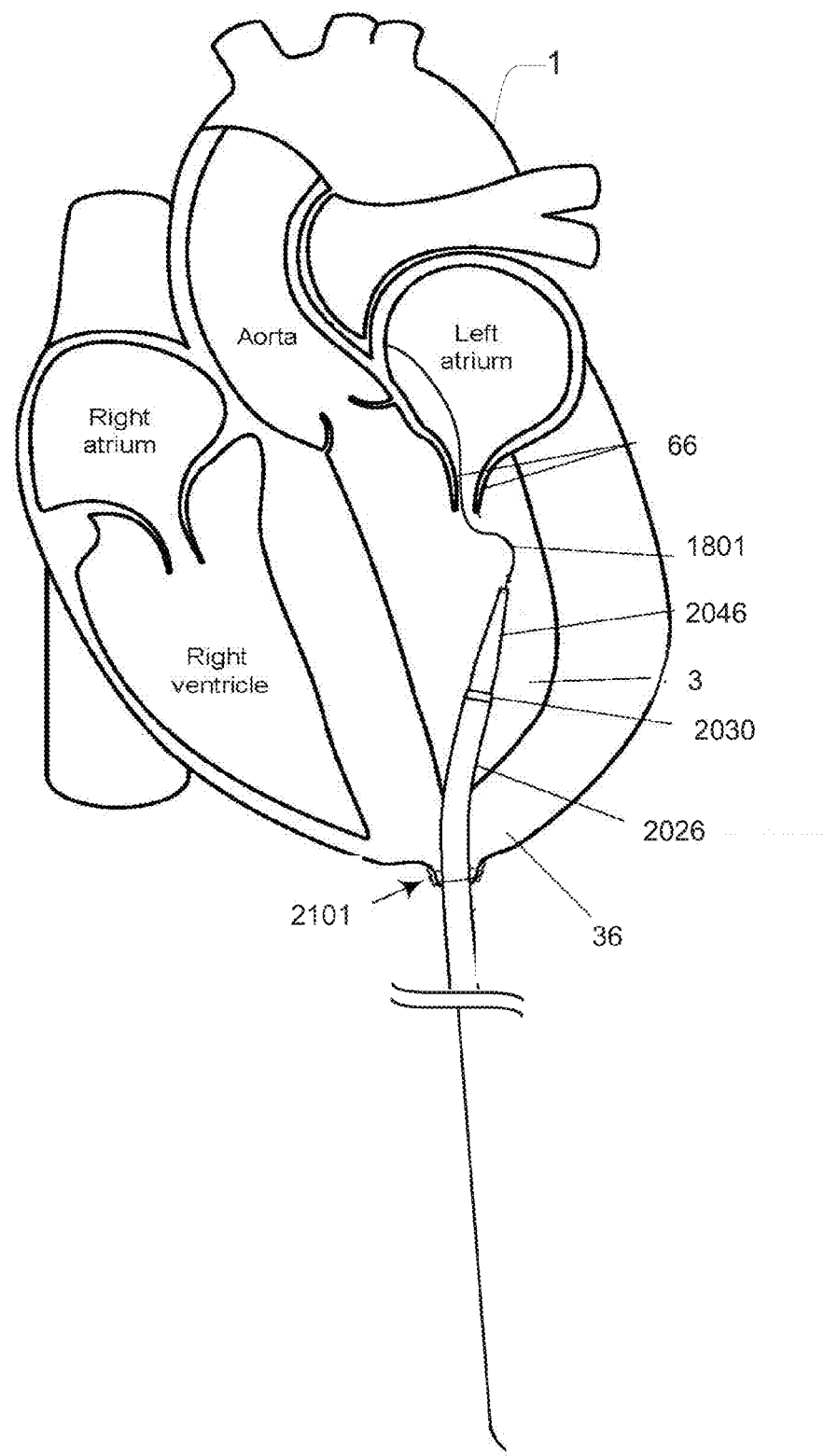
FIG. 21 illustrates purse-string sutures and pledgets secured around the introducer consistent with the present disclosure.

Once the introducer 2026 has been advanced into the left ventricle 3 through the puncture in apex 36, one or more (e.g., 2, 3, 4, 5, 6, 7, 8, 9, 10 or more) purse-string sutures and/or one or more (e.g., 2, 3, 4, 5, 6, 7, 8, 9, 10 or more) pledgets 2101 may be secured around the shaft of the introducer 2026 and the puncture as generally illustrated in FIG. 21. The purse-string sutures and/or pledgets 2101 are configured to apply a radially compressive force against the shaft of the introducer 2026 during the procedures, thereby minimizing the potential for accidentally tearing the heart tissue proximate to the incision and also minimizing blood loss during the procedure. For example, one or more heavy-gauge sutures may be passed around the shaft of the introducer 2026 in a continuous loop, so that when it is all the way around, the suture can be pulled tight like a noose or purse-string to hold the surrounding tissue tightly around the introducer 2026. To prevent the suture from tearing through the tissue, each time the suture passes through tissue, the suture also passes through a small pledget of woven polyester fabric. For example, 1, 2, 3, 4, 5, 6, 7, 8, 9, 10 or more purse-string sutures, each with 1, 2, 3, 4, 5, 6, 7, 8, 9, 10 or more pledgets, may be used to secure the introducer to the ventricle wall. In one embodiment, 2 purse-strings, each purse-string with 2 pledgets is used to secure the introducer 2026 to the left ventricle wall. In another embodiment, 2 purse-strings, each purse-string with 3 pledgets is used to secure the introducer 2026 to the left ventricle wall. In another embodiment, 2 purse-strings, each purse-string with 4 pledgets is used to secure the introducer 2026 to the left ventricle wall. In one embodiment, 4 purse-strings, each purse-string with 2 pledgets is used to secure the introducer 2026 to the left ventricle wall. One of skill in the art will readily appreciate the number of purse-strings and pledgets to use in the methods described herein.

In one embodiment dilator 2028 may include at least one lumen configured to receive at least a portion of the third guide wire 1801. For example, the lumen may have an internal diameter of approximately 0.038". The dilator 2028 may also comprise a shaft including a tapered tip region 2046. The tip 2046 may be provided to facilitate advancing the tip 2046 into the puncture site in the apex 36 as the dilator 2028 is introduced over the third guide wire 1801. The shaft may comprise a plurality of segments or portions having different stiffness or hardness to produce the desired overall curvature. The shaft may be formed from one or more suitable polymers such as, but not limited to, a polyether block amide. The shaft may have a constant inner and/or outer diameter and may be made from different materials to provide the various stiffness or hardness. Alternatively, or in addition, the shaft may have different inner and/or outer diameters and may be made from one or more materials. For example, the various stiffness or hardness of the shaft may be provided by varying the thickness of the shaft at the different segments or portions. The different hardness of the segments may provide differing degrees of bending stiffness to the dilator 2028 which may facilitate advancing the dilator 2028 into and/or out of the left ventricle 3.

Because of the predetermined bend 2027, the distal end 2030 of the introducer 2026 and/or dilator 2028 is generally aligned with the mitral valve 61. With this in mind, once the introducer 2026 is positioned in the left ventricle 3, the introducer 2026 may be advanced over the third guide wire 1801 until tip 2046 of dilator 2028 is present in left atrium 6. To facilitate this movement, dilator 2028 may be configured to include a messenger balloon (see FIG. 14A), which may be inflated to ease passage through the chordae 68. Because introducer 2026 and/or dilator 2028 may be advanced over third guide wire 1801 however, the use of such a messenger balloon is not required.

Figure 22:
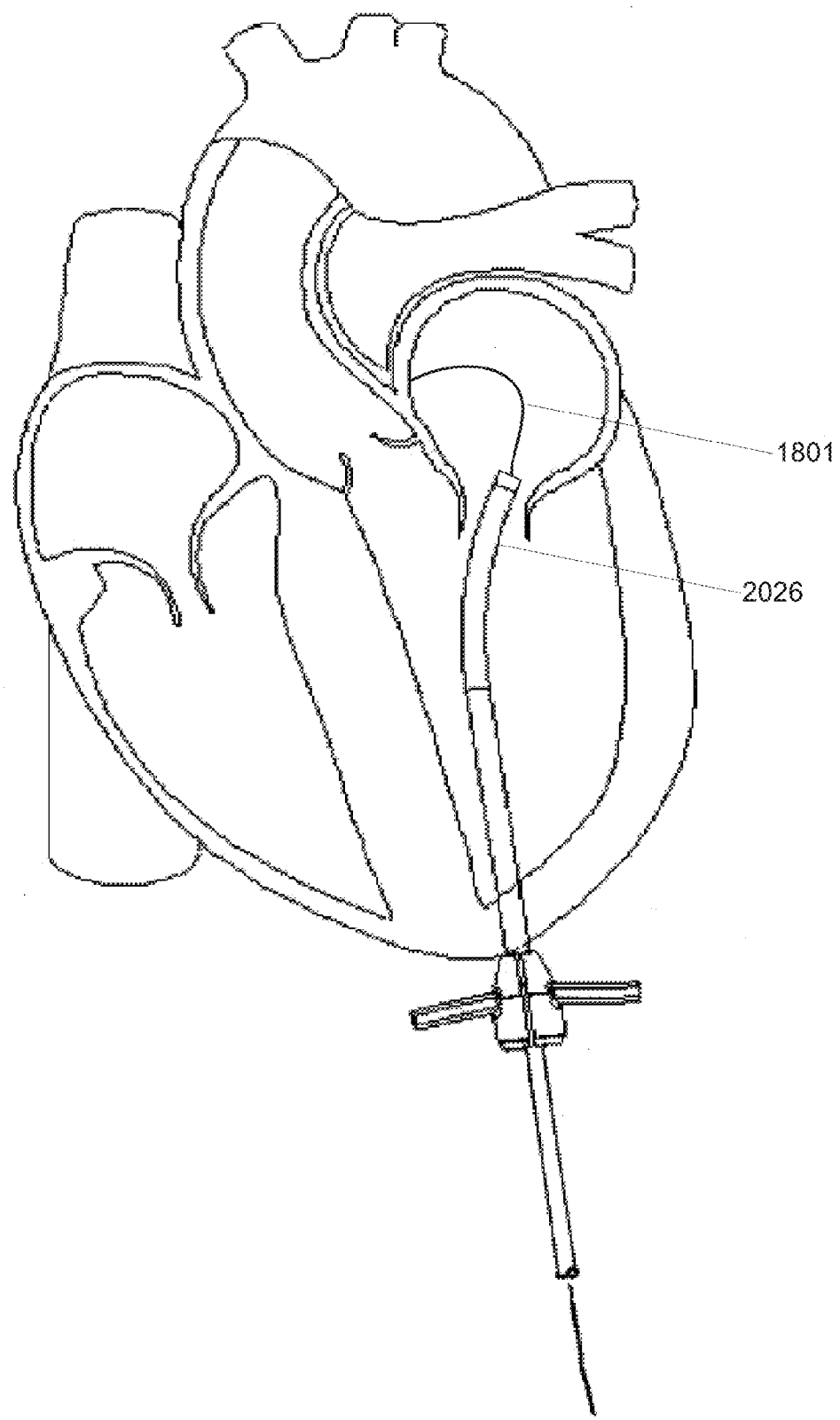
FIG. 22 illustrates the introduced advanced over the guide wire to the left atrium consistent with the present disclosure.

Once the introducer 2026 has been advanced through the mitral valve 61 into the left atrium 6, the dilator 2028 may be withdrawn over through introducer 2026. This leaves the distal end of introducer 2026 and third guide wire 1801 present in left atrium 6, as generally shown in FIG. 22. Third guide wire 1801 may then be withdrawn by drawing it proximally back through transseptal puncture 13 and the vasculature of the patient, or by drawing it distally through introducer 2026 and out of the patient through a thoracotomy or other incision. Upon withdrawal of third guide wire 1801, a distal end of introducer 2026 may be left in left atrium 6, as generally shown in FIG. 23.

Figure 23:
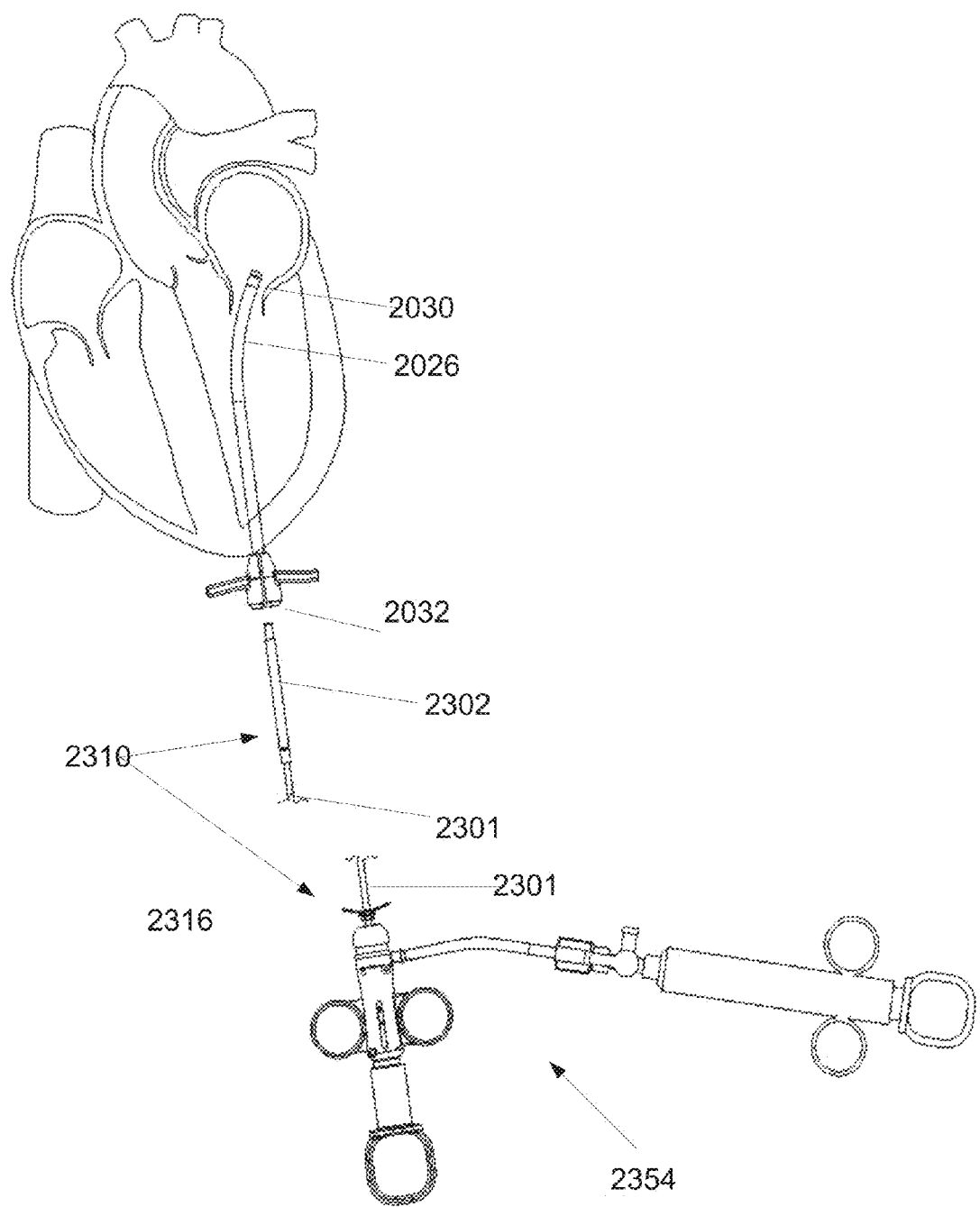
FIG. 23 illustrates an implant being loaded into the introducer.

At this point, an implant 2310 may be loaded into the introducer 2026 (for example, through the splitter 2032) as also shown in FIG. 23. Prior to loading the implant 2310 into the introducer 2026, the implant 2310 may be de-aired. If entrapped air from the implant 2310 is allowed to be introduced into the patient's cardiovascular system, the air may travel to the patient's brain or other parts of the patient's body where it may cause serious bodily harm and/or death (for example, due to blood clotting or the like). As will be described later, implant 2310 may include an elongated shaft 2301 that includes at least one lumen 2303 in fluid communication with an inflatable valve body 2302 comprising a spacer cavity 2304. Implant 2310 may further include an anchor assembly 2316 To de-air the implant 2310, a fluid (such as, but not limited to, a saline solution or the like) may be injected through the lumen 2303 into the spacer cavity 2304 to flush away and/or remove any entrapped air before the implant 2310 is inserted into the introducer 2026.

Shaft 2301 of implant 2310 may have a length that is substantially longer than the length of introducer 2026, and may extend outside the heart, into a thoracic space, and potentially out of the body of a patient (e.g., through a thoracotomy or other incision) even when implant 2310 is sited within the heart. For example, the shaft 2301 may be long enough to allow a surgeon to manipulate the implant 2310 from outside of the patient's body while the implant 2310 is disposed within the left atrium 6/mitral valve 61. The shaft 2301 may include generally flexible tubing such as, but not limited to, a poly(tetrafluoroethylene) (PTFE) tube defining a lumen. Optionally, the exterior surface of the shaft 2301 may include a fabric sheath or the like configured to prevent blood clots from becoming dislodged off the shaft 2301. The shaft 2301 may also optionally include one or more stiffeners (not shown) to provide the necessary amount of rigidity to the shaft 2301 such that it is able to maintain the position of the implant 2310 with respect to the mitral valve 61 when installed. The stiffener may include, for example, braided mesh or the like.

Figure 24:
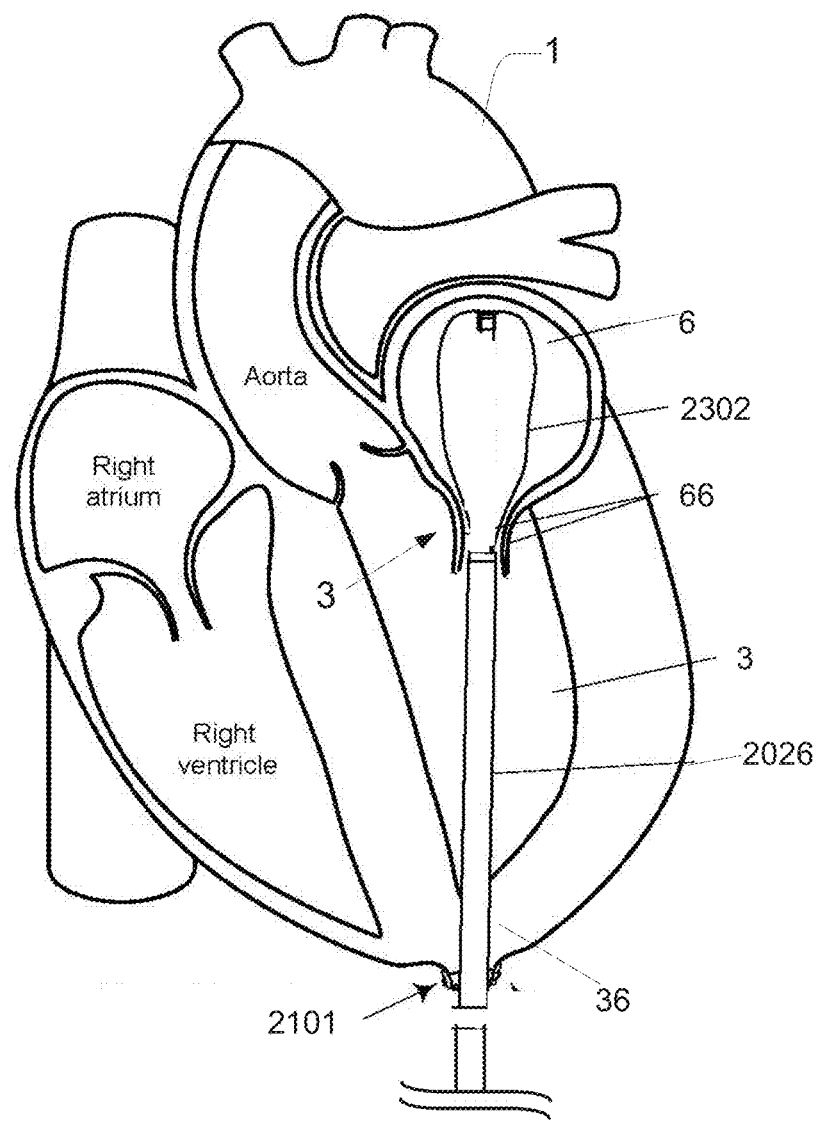
FIG. 24 illustrates the implant in the left atrium.
Figure 25:
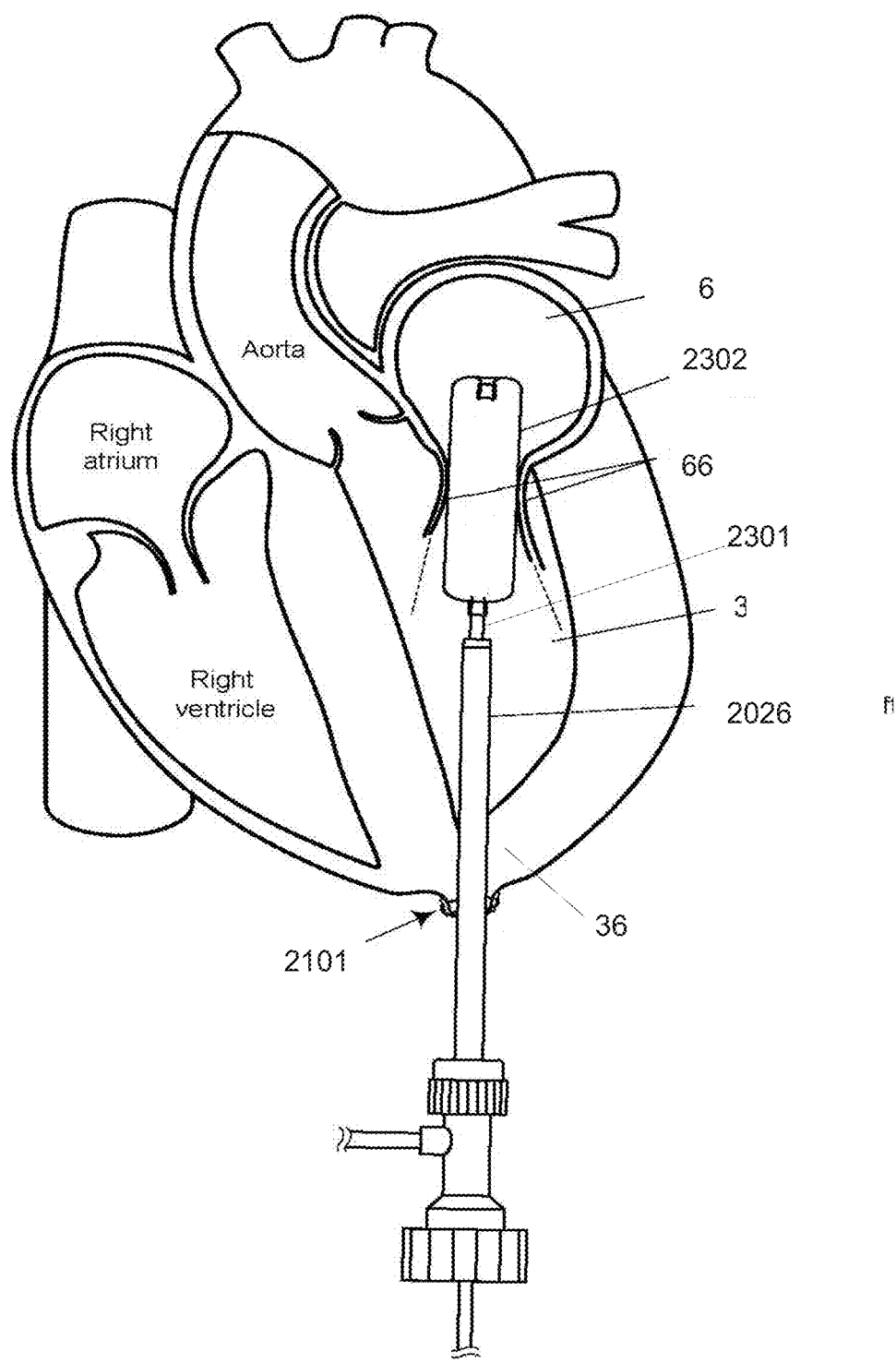
FIG. 25 illustrates the implant in the mitral valve.

According to one embodiment, the shaft 2301 is secured to a handle assembly 2354 and the anchor assembly 2316 may be disposed proximate to the handle assembly 2354, as shown in FIG. 23. The handle assembly 2354 may be used to advance implant 2310 through the introducer 2026 until at least a portion of the implant 2310 (e.g., a deflated inflatable valve body 2302) protrudes beyond the distal end 2030 of the introducer 2026 in the left atrium 6 as generally illustrated in FIG. 24. Once a portion of the valve body 2302 of implant 2310 protrudes beyond the distal end 2030 of the introducer 2026, the introducer 2026 may be retracted slightly to allow the rest of the valve body 2302 to protrude beyond the distal end 2030. The valve body 2302 may also be inflated using the handle assembly 2354 and pulled back from the left atrium 6 and into the annulus of the mitral valve 3 as generally illustrated in FIG. 25. The position of the implant 2310 within the annulus of the mitral valve 61 may be determined using one or more markers on the implant 2310 (e.g., radio-opaque markers) which may be visible under fluoroscopy. The distal end 2030 of the introducer 2026 is now disposed in the left ventricle 3. Contrast medium can be injected into the introducer 2026, to the left ventricle 3 to verify if the mitral regurgitation has been significantly reduced by the action of the valve body 2302 engaging with the cusps 66 of the mitral valve 61.

Figure 26:
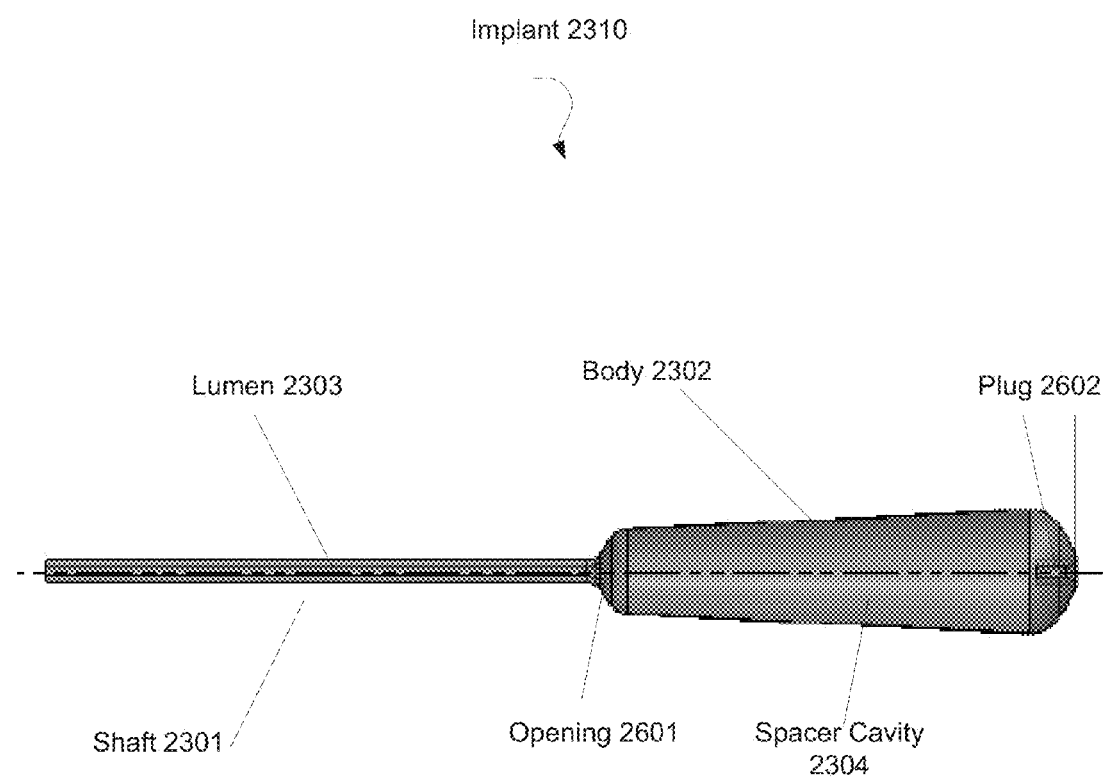
FIG. 26 illustrates one embodiment of an implant consistent with the present disclosure.

One example of the structure of implant 2310 is shown in FIG. 26. As noted previously, implant 2310 includes shaft 2301 and an inflatable valve body 2302. Inflatable valve body 2302 comprises a proximal end and a distal end. A distal end of the inflatable valve body 2302 is furthest from an opening 2601. A proximal end of inflatable valve body 2302 is at or near opening 2601. In some aspects, one or more radiopaque markers are positioned at or near the proximal end of the inflatable valve body. In some aspects, one or more radiopaque markers are positioned at or near the distal end of the inflatable valve body. In yet another aspect, one or more radiopaque markers are positioned at or near the proximal and distal ends of the inflatable valve body. As will be appreciated by one of skill in the art, one or more radiopaque markers assist a physician to perform the methods described herein. Using known techniques (e.g., x-ray, fluoroscopy, etc.), a physician can confirm correct placement of the implant 2310 in an individual.

Shaft 2301 includes a lumen 2303 which is in fluid communication with spacer cavity 2304. In one embodiment, shaft 2301 extends to at least a proximal end (e.g., at or near opening 2601) of the inflatable valve body. In another embodiment, shaft 2301 extends through a proximal end of the inflatable valve body 2302. In another embodiment, shaft 2302 is attached to a distal end of inflatable valve body 2302 and extends through a proximal end of the inflatable valve body. Any or all of the portions of implant 2310 may be formed from or biologically acceptable material, for example, Elast-Eon™ material or the like. In some embodiments, at least the walls of inflatable valve body 2302 are formed of a resiliently deformable biologically acceptable material.

Figure 27:
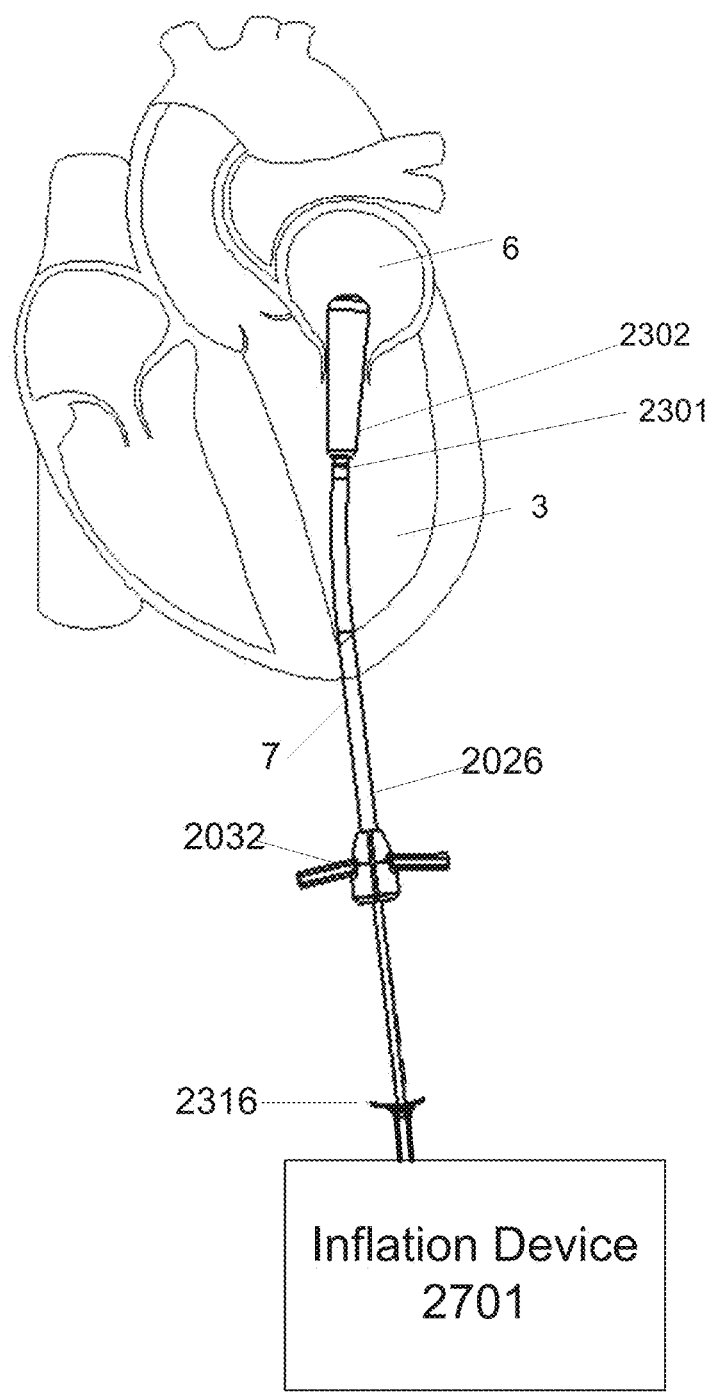
FIG. 27 illustrates the implant in the mitral valve, an inflation device and a splitter.
Figure 29A:
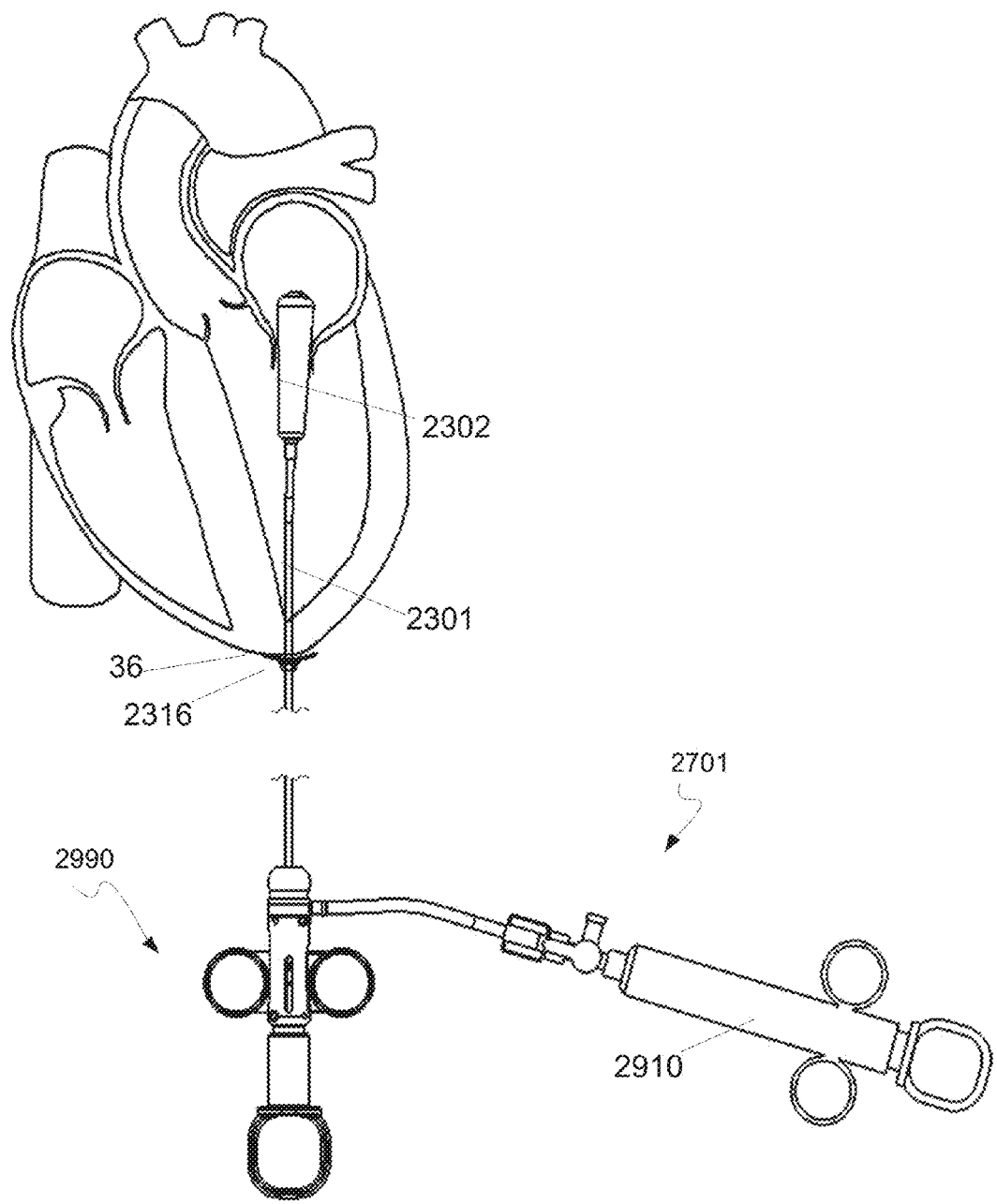
FIG. 29A illustrates the implant in the mitral valve and an inflation device in the form of an inflation handle assembly.
Figure 29B:
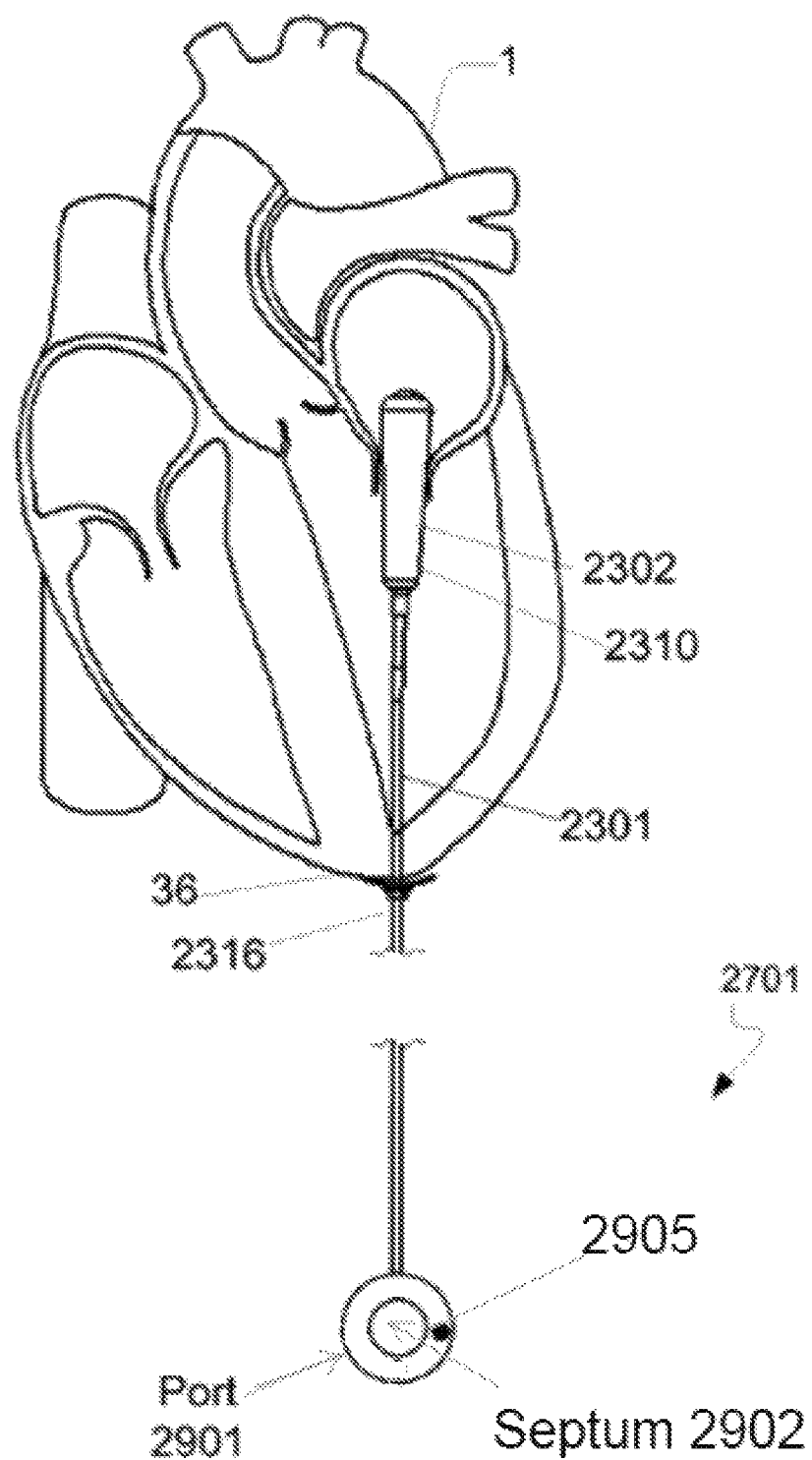
FIG. 29B illustrates the implant in the mitral valve and an inflation device in the form of an inflation port.

A first (e.g., proximal) end of the wall of inflatable valve body 2302 may be coupled, mounted, integrally formed with or otherwise secured to a portion of the shaft 2301. Implant 2310 may include an opening 2601 proximate to the point of connection with shaft 2301, and which may fluidly connect lumen 2303 of shaft 2301 with spacer cavity 2304 of inflatable valve body 2302 so as to allow an expansion medium (such as, but not limited to, saline or the like) into a spacer cavity 2304 from an inflation device 2701, as generally shown in FIG. 27. Inflation device 2701 may for example be handle assembly 2354 (e.g., as shown in FIGS. 23 and 29A) or an inflation port 2901 (e.g., as shown in FIG. 29B). In any case, opening 2601 may be a component of the valve body 2302 and/or may include an extension of the shaft 2301.

The cavity 2304 may be defined by the opening 2601 and the wall of inflatable valve body 2302. The distal end of the inflatable valve body 2302 may include an end plug 2602 configured to seal the distal end of valve body 2302. Alternatively, the distal end of inflatable valve body 2302 may be formed of a continuous piece of material such that spacer cavity is naturally sealed at the distal end of valve body 2302.

As may be appreciated, a surgeon may selectively expand and retract inflatable valve body 2302 and more specifically spacer cavity 2304 by injecting and withdrawing an expansion or inflation medium into and from spacer cavity 2304 (e.g., via lumen 2303). Once the spacer cavity 2304 is inflated to a desired degree, the degree of inflation may be maintained by inflation device 2701, which may be configured to limit or prevent the withdrawal of expansion or inflation medium from spacer cavity 2304 by plugging or backstopping lumen 2303 at a proximal end of shaft 2301.

Turning now to FIG. 27, the implant 2310 is illustrated with the inflatable valve body 2302 within the heart. The shaft 2301 of the implant 2310 is disposed within the introducer 2026 (e.g., a split catheter) and coupled to the inflation device 2701. The anchor assembly 2316 is also shown disposed proximate to the inflation device 2701. The inflation device 2701 may include, comprise or be coupled to a source of an expansion medium (e.g., a plunger, a syringe, an inflation port, etc.) for injecting and withdrawing expansion medium (inflation fluid) into/from body 2302 of implant 2310 via lumen 2303 in shaft 2301. Accordingly, a surgeon or physician may control the inflation (e.g., injection) and/or withdrawal of expansion medium by appropriately controlling the influx or withdrawal of expansion medium from and to the source of expansion medium.

As noted previously, a surgeon may use the inflation device 2701 (e.g., a handle assembly 2354) to manipulate the implant 2310 such that the inflatable valve body 2302 is disposed within the mitral valve 61. The inflatable valve body 2302 may also be expanded to the desired size using the inflation device 2701 and an associated source of expansion medium. The spacer cavity 2304 may be sealed using the inflation device 2701 once the desired size of the inflatable valve body 2302 is determined.

Figure 28:
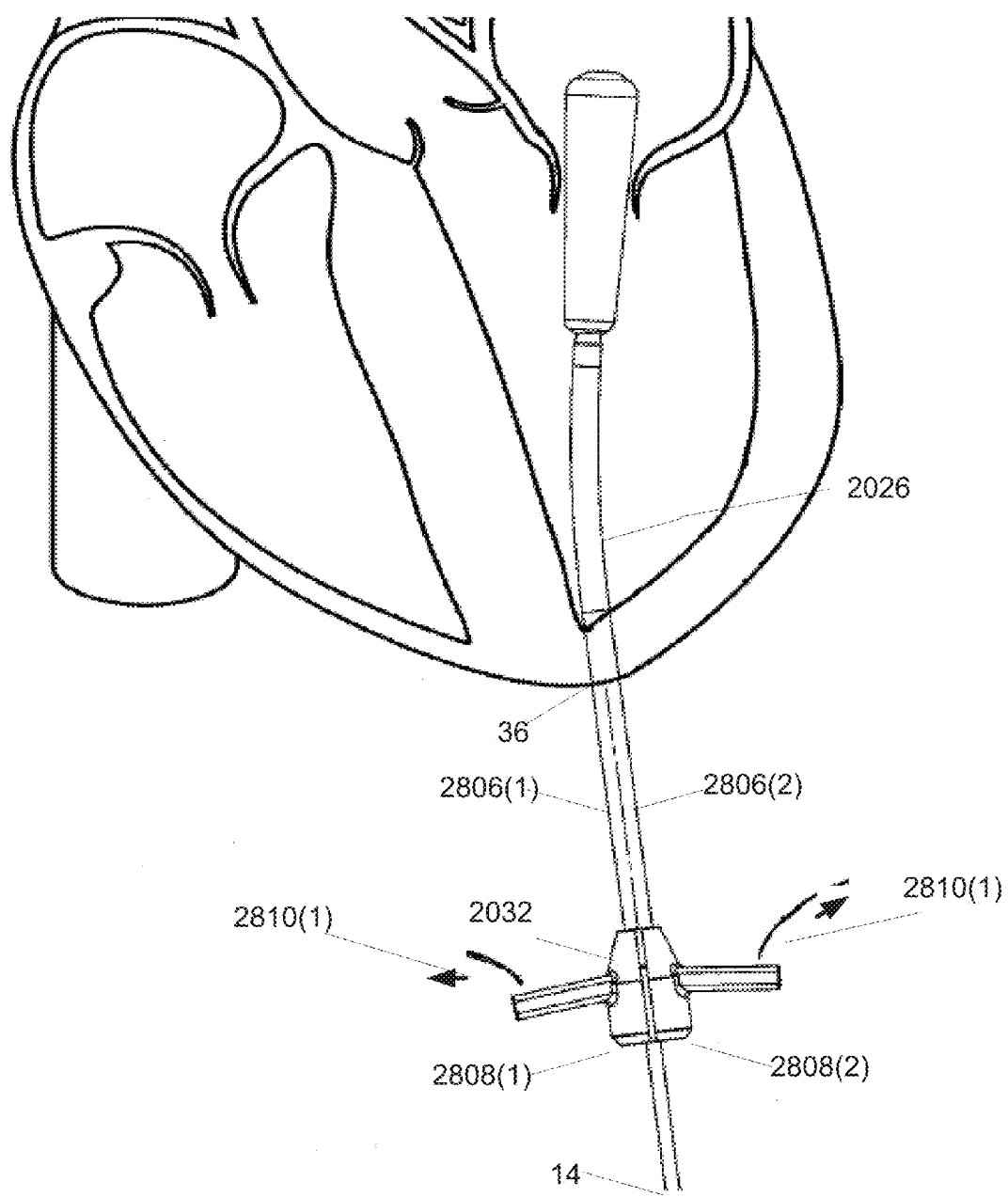
FIG. 28 illustrates splitting the introducer after the implant has been verified in the mitral valve.

After the operation of the inflatable valve body 2302 has been verified and the spacer cavity 2304 has been sealed, the introducer 2026 may be removed from the shaft 2301, for example, as generally illustrated in FIG. 28. For example, the splitter 2032 may be used to split the introducer 2026 into two or more pieces 2806(1), 2806(2) along its length, for example, by pulling the two halves 2808(1), 2808(2) generally in the directions of arrows 2810(1), 2810(2). As the introducer 2026 is split, the introducer 2026 may be retracted from the heart through the puncture in the apex 36. The purse string sutures 2101 (not shown for clarity) may also be tightened as the introducer 2026 is removed from the puncture in the apex 36 to minimize blood loss. Once the introducer 2026 has been removed from the shaft 2301, the anchor assembly 2316 may be advanced along the shaft 2301 until the anchor assembly 2316 is adjacent to and/or abuts against the apex 36 of the heart, for example as generally illustrated in FIGS. 29A and 29B.

As shown in FIG. 29A and generally described above, inflation device 2701 may be in the form of an inflation handle assembly 2990. Inflation handle assembly 2990 may include an inflation port (not labeled) which may be fluidly coupled to an expansion medium source 2910, such as a plunger, syringe, etc., as shown in FIG. 29A. By appropriate manipulation of inflation handle assembly 2990 and/or expansion medium source 2910, a surgeon may inject or withdraw expansion medium (inflation fluid) into and from spacer cavity 2304 of implant 2310.

Alternatively or additionally, inflation device 2701 may be in the form of an inflation (e.g., injection) port 2901, as generally illustrated in FIG. 29B. In such instances, inflation (e.g., injection) port 2901 comprises a septum 2902 and at least one (e.g., one or more) opening or lumen that is in fluid communication with lumen 2303 of shaft 2301 of implant 2310. In some embodiments, injection port 2901 is configured to allow for introduction of an expansion medium (inflation fluid) to lumen 2303 and inflatable valve body 2302. In one embodiment, injection port 2901 is in fluid communication with lumen 2303 and inflatable valve body 2302.

Inflation (e.g., injection) port 2901 may be configured to seal lumen 2303 of shaft 2301 when it is not in use, e.g., when a desired size/operation of inflatable valve body 2302 has been achieved. To facilitate injection and/or withdrawal of an expansion medium (inflation fluid) to and/or from implant 2310, port 2901 comprises a septum 2902. In some embodiments, septum 2902 is a pierceable septum. In some embodiments, septum 2902 is a self-sealing septum. In some embodiments, septum 2902 is pierceable and self-sealing. For example, septum 2902 may be pierced by a needle of a syringe, whereafter the syringe may inject or withdraw an expansion medium into or from port 2901 (and hence implant 2310). One of skill in the art will readily appreciate that septum 2902 comprises any one of a number of suitable materials that allow septum 2902 to be pierceable and/or self-sealing (e.g., to be pierced by a needle and self-seal after the needle is withdrawn from the septum). For example, septum 2902 comprises of any one or any combination of the following: silicone, silicone gels, nitrile rubbers, polyurethanes, and thermoplastics. When the injection port is not in use (e.g., a needle is not piercing the septum), the injection port 2901 and septum 2902 are liquid and/or air tight. Expansion medium (e.g., a liquid and/or gas) contained within port 2901, lumen 2303, and inflatable valve body 2302 does not escape the implant. Any suitable ports may be used as injection port 2901. For example, in some embodiments, the Primo Port, commercially available from Sync-Medical, is used as injection port 2901.

In some embodiments, the expansion medium (inflation fluid) can be any suitable fluid, such as, for example, saline. In one embodiments, the expansion medium is a liquid. There are a number of suitable liquids that can be used to inflate inflatable valve body 2302. For example, normal saline, phosphate buffered saline (PBS), Ringer's solution, water (e.g. sterilized, deionized, etc.), contrast medium (e.g., iodine, barium) can be used as an expansion medium. In one embodiment, the expansion medium comprises water. In one embodiment, the expansion medium comprises a contrast medium. In another embodiment, the contrast medium comprises an iodine-based contrast medium. In another embodiment, the contrast medium comprises a barium-based contrast medium.

In another embodiment, the expansion medium is a gel. In another embodiment, the expansion medium is a gas. In one embodiment, the gas comprises air. In another embodiment, the gas comprises $CO_2$ (carbon dioxide). In another embodiment, the gas comprises $N_2$ (nitrogen).

In some embodiments, inflation (e.g., injection) port 2901 is implanted in a patient, e.g., so as to permit long term adjustment capability to implant 2310 (e.g., by adding more, or removing a portion, of the inflation fluid). In such instances, the injection port 2901 may be formed from biocompatible materials. In some embodiments, the injection port comprises materials with other mechanical and physiological properties that would be beneficial in the devices and methods described herein. Additional properties, for example, may include hypoallergenic, anti-inflammatory, and anti-microbial. One of skill in art will readily appreciate that injection port 2901 may be implanted in a patient in such a manner to allow a physician to easily gain access to the injection port 2901 (e.g., subdermally or subcutaneously). In some embodiments, injection port further comprises one or more suture holes to allow the injection port to be secured with sutures 2905.

Figure 29C:
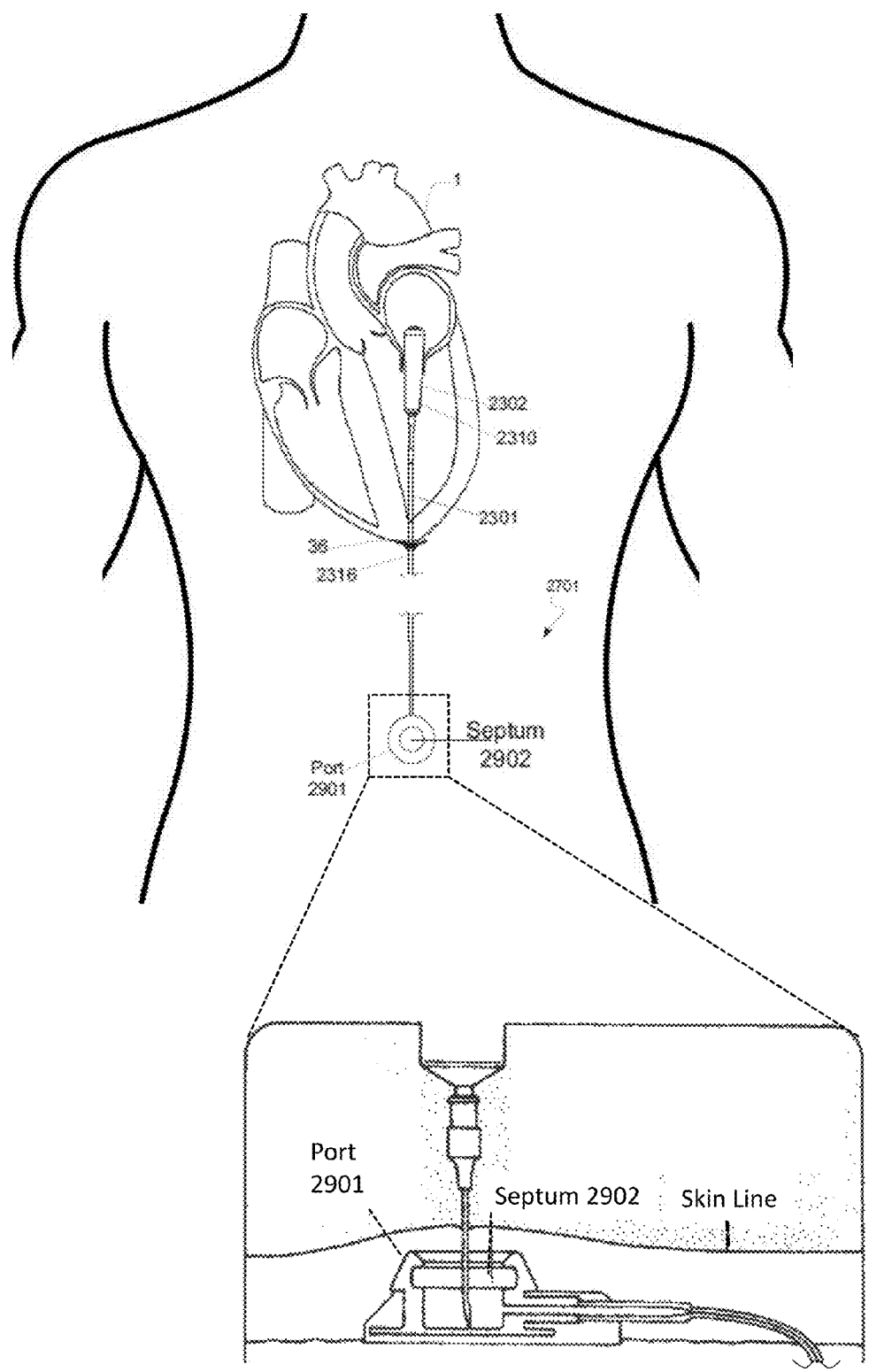
FIG. 29C illustrates the implant in the mitral valve and an exploded view of an inflation device in the form of an inflation port located subdermally or subcutaneously in an individual.

With reference to FIG. 29C, the injection port 2901 can be implanted subdermally in an individual. As will be appreciated by one of skill in the art, injection port can be secured below the skin line (e.g. subdermally, subcutaneously, etc.) in any number of anatomic locations. In one embodiment, the injection port 2901 is at or near the chest wall. In another embodiment, the injection port 2901 is implanted subdermally and positioned at or near the chest wall, near the apex of the heart of an individual. In an embodiment, injection port is at or near the abdomen. In another embodiment, injection port 2901 is implanted transdermally in an individual.

With reference again to FIG. 29B, the heart valve implant 2310 is shown secured to an exterior surface of the apex 36 of the heart by anchor assembly 2316. Once the anchor assembly 2316 is secured to the heart 1, the shaft 2301 may be sealed proximal to the anchor assembly 2316 and the shaft 2301 may be cut proximal to the seal. Alternatively or additionally, shaft 2301 may remain sealed by an inflation device (e.g., inflation port 2901), in which case subsequent adjustment of the inflation of implant 2310 may be permitted. As noted previously, the inflation device 2701 (e.g., inflation port 2901) may itself be implanted (e.g., subdermally) within the patient, e.g., in instances where long term adjustment of the inflation of implant 2310 may be desired. In some aspects, when implant 2310 is installed, inflatable valve body 2302 is configured to interact and/or cooperate with (e.g., engage) at least a portion of the native mitral valve 61 (e.g., the cusps 66) to reduce and/or eliminate regurgitation. As such, the configuration and/or geometries of the implant 2310 and in particular inflatable valve body 2302 may vary depending upon the particulars of the condition of the patient's mitral valve 61 and the damage thereto. In addition, the implant 2310 (e.g., the inflatable valve body 2302 and/or the shaft 2301) may have sufficient overall rigidity to maintain the inflatable valve body 2302 within the mitral valve 66 such that the implant 2310 performs its function as intended.

Figure 30:
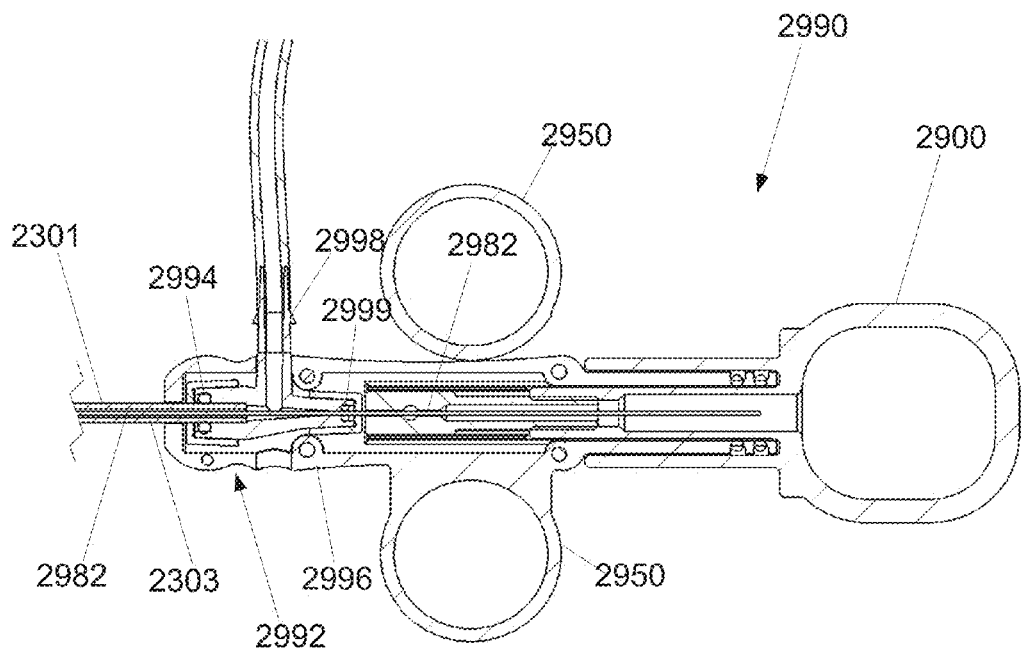
FIG. 30 illustrates one embodiment of an inflation handle assembly in a retracted position prior to filling.
Figure 31:
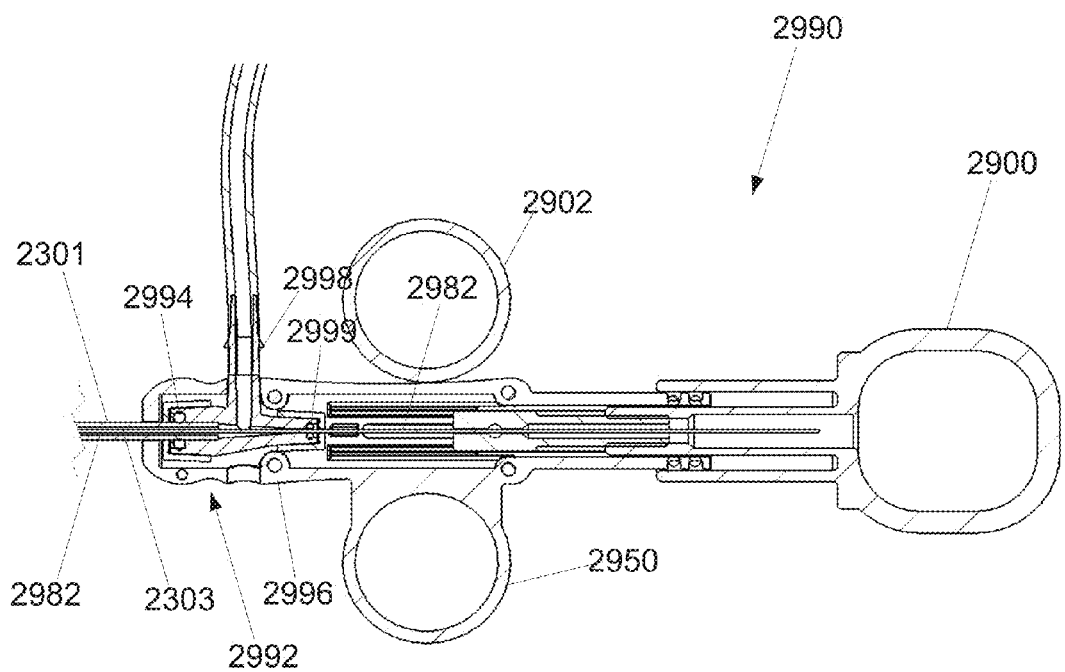
FIG. 31 illustrates the inflation handle assembly in an expanded position after filling.
Figure 32:
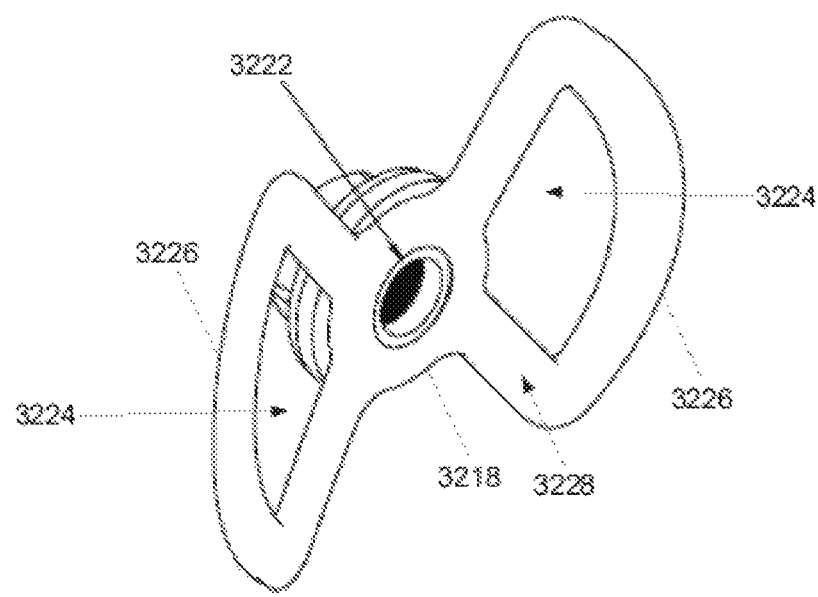
FIG. 32 illustrates a perspective view of one embodiment of an anchor assembly.

Turning now to FIGS. 30 and 31, one embodiment of an inflation handle assembly 2990 is generally illustrated. A proximal end 2992 of the shaft 2301 may be secured (either permanently or releasably) to a portion of the inflation handle assembly 2990. For example, the shaft 2301 may be hermetically sealed and coupled to inflation handle assembly 2990 using one or more seals 2994. The body 2996 of the inflation handle assembly 2990 includes an inflation port 2998 which is fluidly coupled to the lumen 2303 of the shaft 2301. The inflation port 2998 is configured to be secured to an inflation source (e.g., but not limited to, a plunger/syringe or the like, not shown) for providing the expansion medium to the spacer cavity 2304 as described herein.

The plunger wire 2982 extends from the lumen 2303 of the shaft 2301 and passes through the body 2996 of the inflation handle assembly 2990. One more seals 2999 may be provided to seal the body 96 to the plunger wire 2982 as the plunger wire 2982 passes through the body 2996. The proximal end of the plunger wire 2982 is optionally secured to a translator 2900. The translator 2900 (which may include a ring, slide, knob, or the like) may be configured to move with respect to the body 2996 to push or pull the plunger wire 2982 within lumen 2303 and thus seal or unseal lumen 2303. For example, when the translator 2900 is in the position illustrated in FIG. 30, the plunger wire 2982 may be disposed within the lumen 2303 of shaft 2301, and thus lumen 2303 may be sealed. When the translator 2900 is in the position illustrated in FIG. 31, the plunger wire 2982 may be at least partially withdrawn from the proximal end of shaft 2301, thus unsealing lumen 2303 and permitting the injection/withdrawal of expansion medium (withdrawal of plunger wire 2882 not shown for clarity).

The inflation handle assembly 2990 may optionally include one or more handle features 2950 extending from the body 2996 that are configured to facilitate handling of the inflation handle assembly 2990 with one hand. For example, the inflation handle assembly 2990 may include two handle features 2950 disposed on generally opposite sides of the body 2996, each of which is configured to receive a different one of a user's fingers (for example, the pointer and middle fingers, respectively). The translator 100 may feature a ring configured to receive a user's thumb. With this arrangement, the surgeon may grip the inflation handle assembly 2990 with a single hand and translate the translator 2900 back and forth to urge the plunger wire 2982 into and out of lumen 2303 of shaft 2301. This arrangement allows the surgeon to control the sealing and unsealing of lumen 2303, and may permit the surgeon to control an expansion medium source with his other hand.

Figure 33:
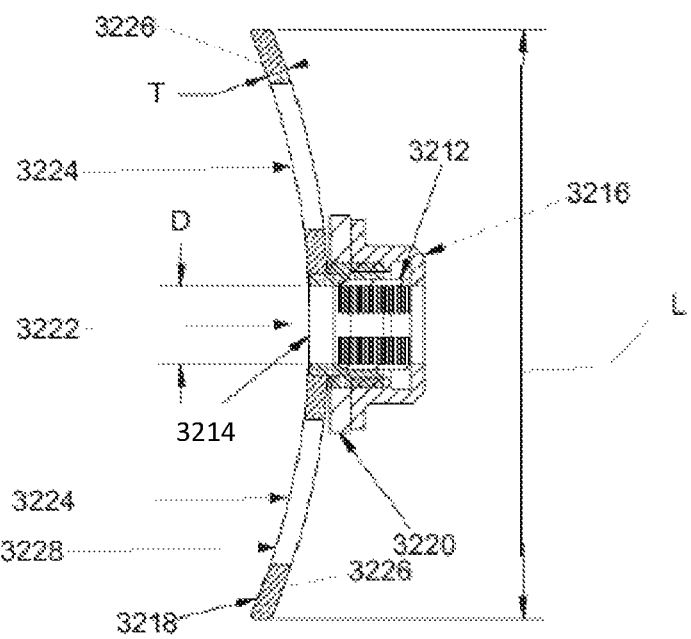
FIG. 33 illustrates a cross-sectional side view of one embodiment of an anchor assembly.
Figures 34, 35:
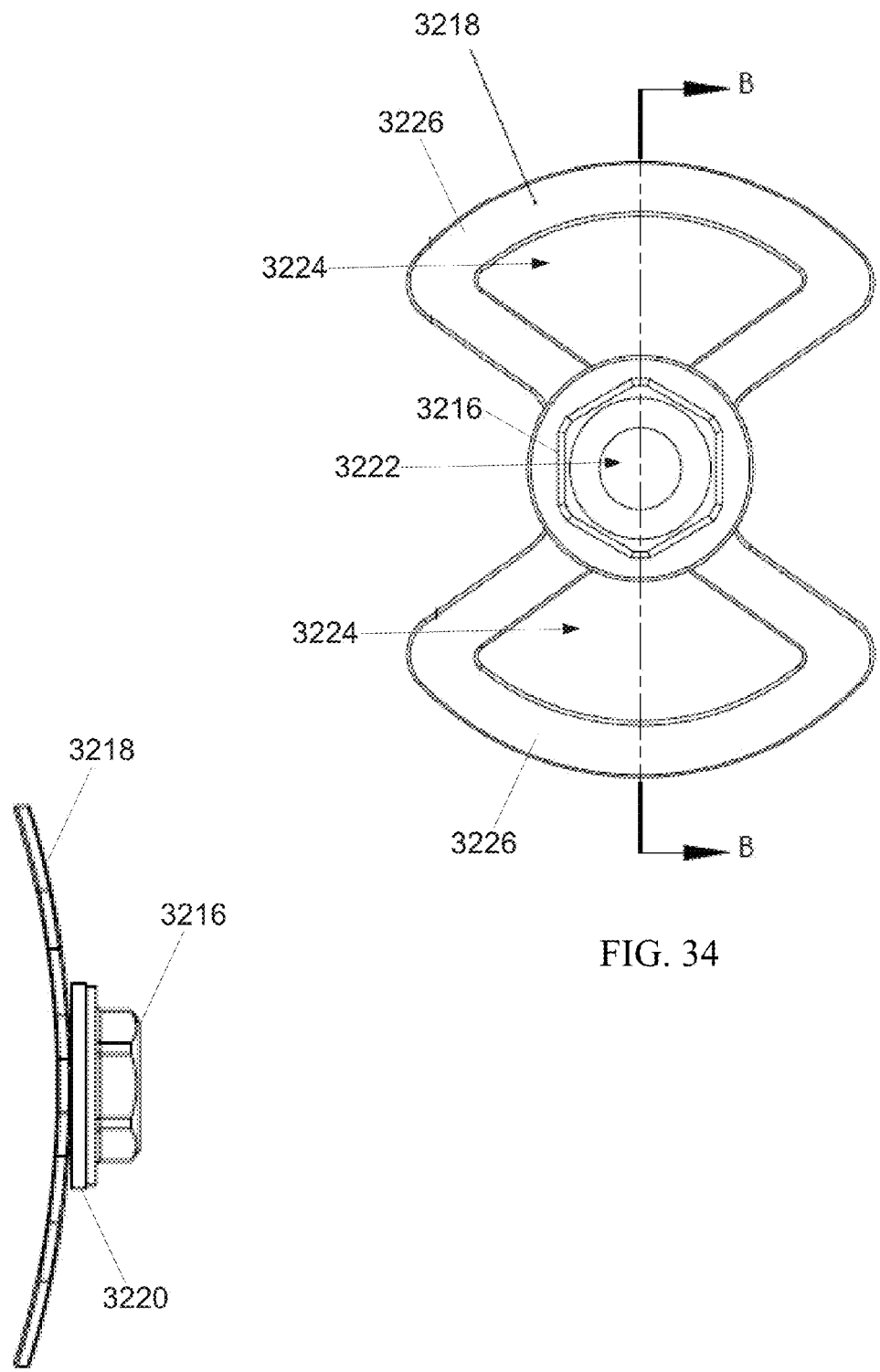
FIG. 34 illustrates a front view of one embodiment of an anchor assembly.
FIG. 35 illustrates a side view of one embodiment of an anchor assembly.

Turning now to FIGS. 32-35, various views of one embodiment of an anchor assembly 2316 are generally illustrated. The anchor assembly 2316 (as best seen in FIG. 33 which is a cross-sectional view taken along line B-B of FIG. 34) includes a clamp ring 3212, a collar 3214, a nut 3216, an anchor support 3218, and optionally a felt pad 3220. The anchor assembly 2316 defines a passageway 3222 extending therethrough which is configured to receive and be advanced over the shaft 2301 of the implant 2310. The clamp ring 3212, collar 3214, and nut 3216 are configured to define a compression fitting around a perimeter of the shaft 2301, thereby securing the anchor assembly 2316 to the shaft 2301. In particular, once the anchor assembly 2316 is in place (e.g., abutting against the tissue surround the incision site proximate to the apex 36), the surgeon holds the anchor support 3218 while rotating the nut 3216, thereby compressing the clamp ring 3212 and the collar 3214 to apply a radially compressive force against the shaft 3214. The radially compressive force secures the anchor assembly 2316 to the shaft 2301. For illustrative purposes, the anchor support 3218 may have a length L of 0.875 cm and thickness T of 0.030 cm, and the passageway 3222 may have a diameter D of 0.116 cm.

To secure the anchor assembly 2316 to the heart, the anchor support 3218 may be sutured to the heart tissue. The anchor support 3218 may include one or more openings 3224 and/or arms 3226 over which one or more sutures (not shown for clarity) may be passed to stitch the anchor support 3218 to the heart tissue, and secure the anchor assembly 2316. The mounting surface 3228 of the anchor support 3218 may have a curvature which substantially corresponds to the curvature of the heart tissue proximate to the incision site about the apex 7. The anchor support 3218 may optionally be coated/covered/wrapped with pledget material. The pledget material facilitates tissue to grow over the anchor support 3218, thereby further enhancing the connection between the anchor assembly 2316 and the heart.

Other anchor assemblies can be used to secure the implant 2310 to the heart. For example, a one or more prongs, barbs, staples, clamps, and/or helical screws can be used to secure the implant 2310 to the heart.

Figure 36:
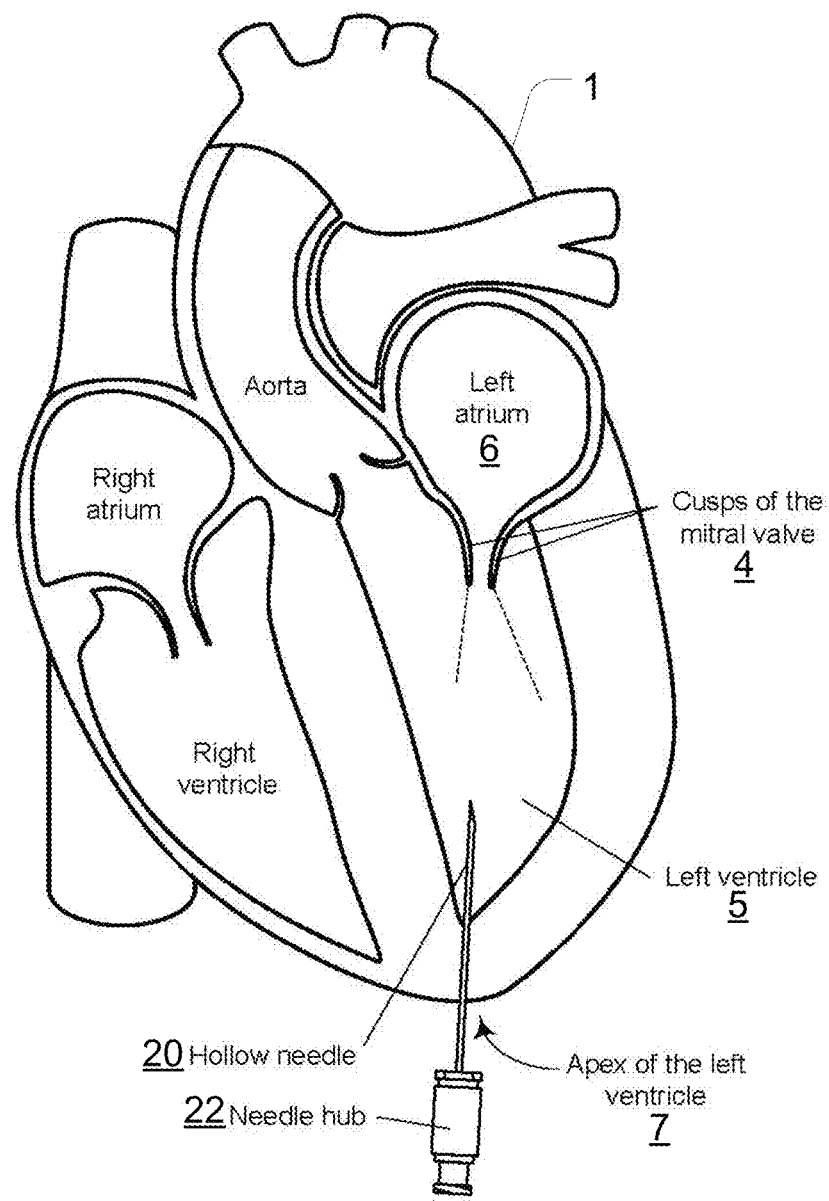
FIG. 36 illustrates a needle being inserted through the apex into the left ventricle.

As described herein, the method of delivering a heart valve implant within in a heart is achieved by a variety of procedures. In one embodiment, the method comprises trans-apically delivering a heart valve implant within a heart. With reference to FIG. 36, the trans-apical system and method includes gaining access to the left ventricle 5.

Figure 40:
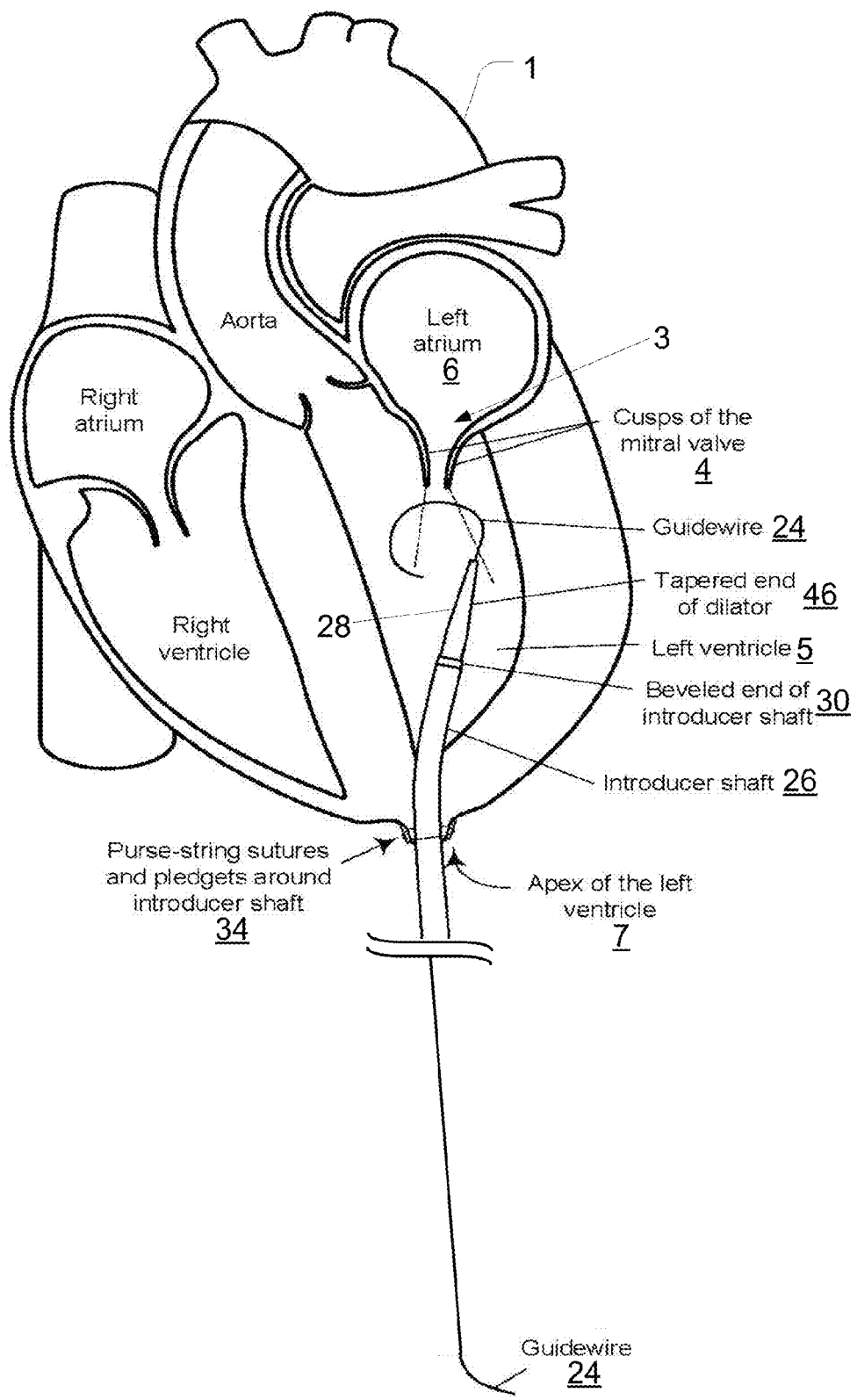
FIG. 40 illustrates purse-string sutures and pledgets secured around the introducer.

One of skill in the art will readily appreciate that one or more purse-string sutures are in place before performing the methods described herein. In one embodiment, one or more purse-string sutures and/or pledgets are secured at or near the apex 7 of the heart before hollow needle 20 is inserted through the apex 7 of the left ventricle 5 (not shown in FIG. 36). The purse-string sutures and/or pledgets 34 (see FIG. 40) are configured to minimize the potential for accidentally tearing the heart tissue proximate to the incision and also minimize blood loss during the procedure.

To prevent the suture from tearing through the tissue, each time the suture passes through tissue, the suture also passes through a small pledget of woven polyester fabric. For example, 1, 2, 3, 4, 5, 6, 7, 8, 9, 10 or more purse-string sutures, each with 1, 2, 3, 4, 5, 6, 7, 8, 9, 10 or more pledgets, may be used to secure the heart so that hollow needle 20 is inserted through apex 7. In one embodiment, 2 purse-strings, each purse-string with 2 pledgets is used to secure the heart. In another embodiment, 2 purse-strings, each purse-string with 3 pledgets is used to secure the heart. In another embodiment, 2 purse-strings, each purse-string with 4 pledgets is used to secure the heart. In one embodiment, 4 purse-strings, each purse-string with 2 pledgets is used to secure the heart. One of skill in the art will readily appreciate the number of purse-strings and pledgets to use in the methods described herein.

Figure 37:
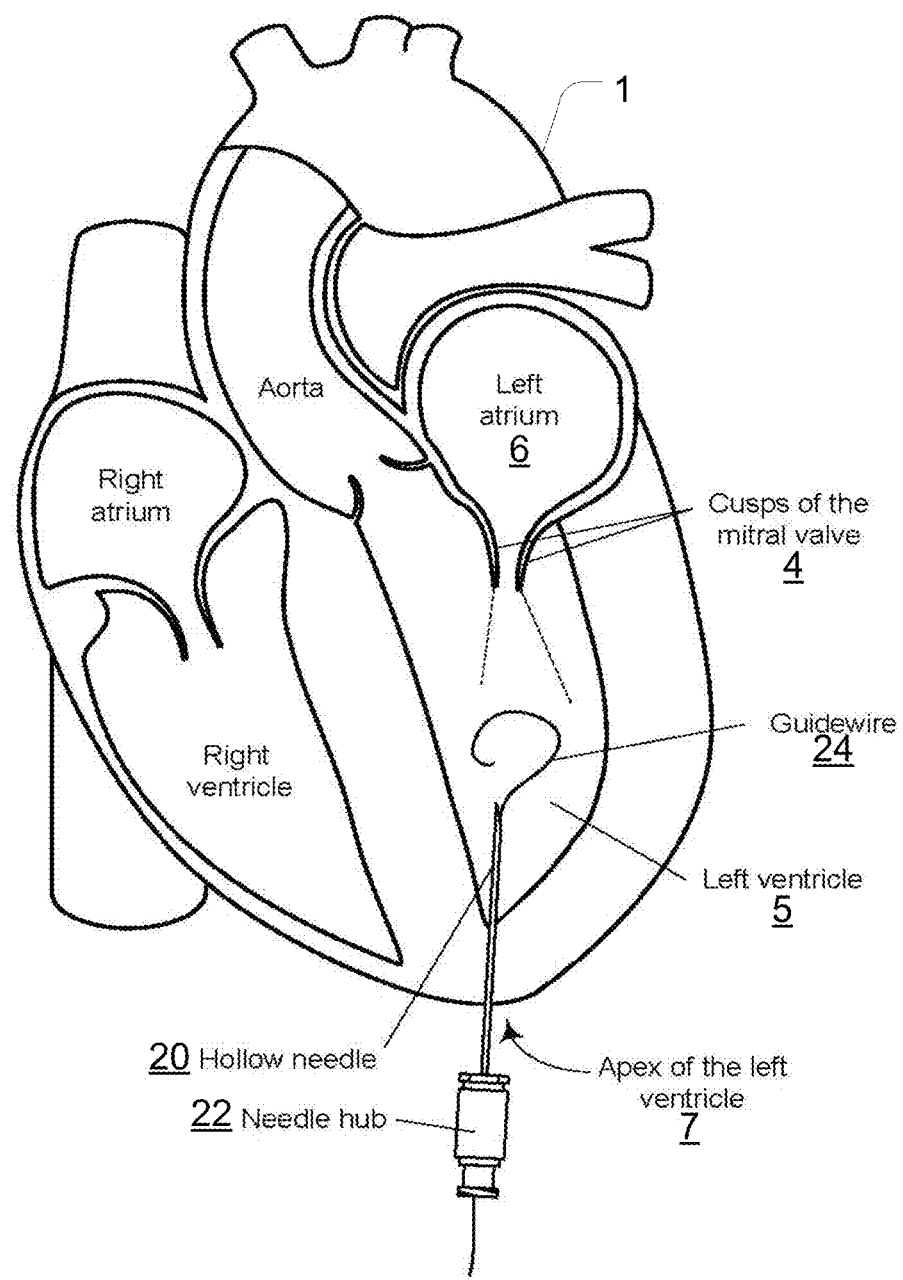
FIG. 37 illustrates a guidewire being inserted through the needle into the left ventricle.

Referring to FIG. 36, once one or more purse-string sutures with one or more pledgets are in place, a hollow needle 20 (which may be coupled to a needle hub 22) is inserted through the apex 7 of the left ventricle 5 and into the left ventricle 5. Once access has been achieved to the left ventricle 5, a guide wire 24 is introduced through the lumen of the hollow needle 20 into the left ventricle 5 as illustrated in FIG. 37. The guide wire 24 may include, for example, a ⅟₃₂" wire and may optionally form a curved, pig-tail-like shape after the guide wire 24 exits the lumen of the hollow needle 20 in the left ventricle 5.

Figure 38:
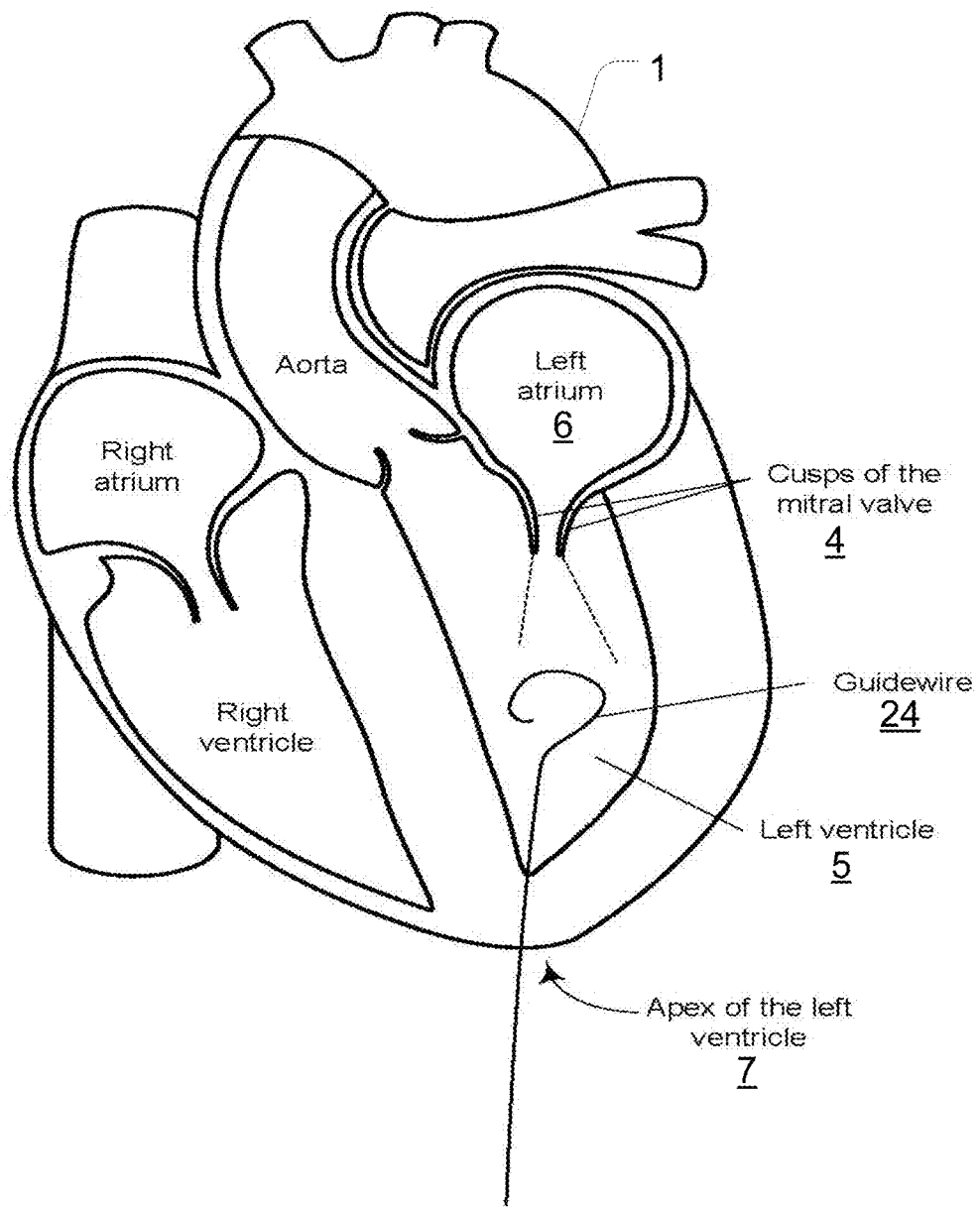
FIG. 38 illustrates the needle removed and the guidewire in the left ventricle.
Figure 39:
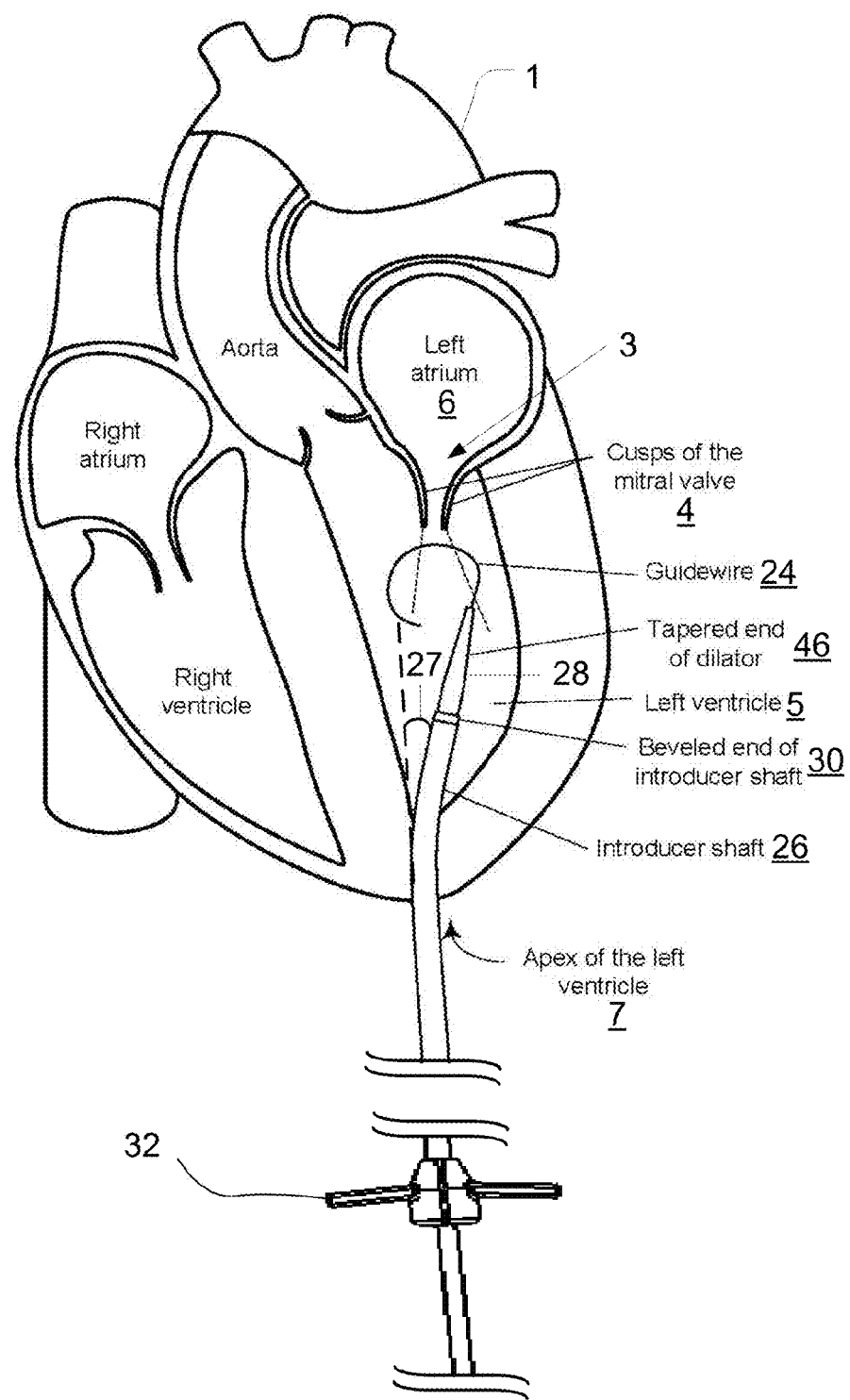
FIG. 39 illustrates one embodiment of an introducer and dilator being inserted into the left ventricle.

With the guide wire 24 in the left ventricle 5, the hollow needle 20 is removed from heart 1, leaving the guide wire 24 remaining in the left ventricle 5 as illustrated in FIG. 38. The guide wire 24 may be used as a pathway for advancing other instruments and devices into the heart 1. For example, an introducer 26 and/or dilator 28 may be advanced along the guide wire 24 into the left ventricle 5 as generally illustrated in FIG. 39.

The distal end 30 of the shaft of the introducer 26 may be beveled to aid in passing the introducer 26 through incision in the apex 7. The introducer 26 may also feature a pre-defined bend 27. The predefined bend 27 is formed in the introducer 26 during the manufacturing of the introducer 26 and is configured to facilitate alignment of the distal end 30 of the introducer 26 with the mitral valve 3. Without the bend 27 (e.g., if the introducer was just linear), it would be very difficult to align the tip 30 of the introducer 26 with the mitral valve 3 and between the two papillary muscles, and into the outflow tract of the mitral valve 3. While the bend/curvature 27 does not appear to be perfectly aligned with the mitral valve 3, this is due (in part) to the three-dimensional path which is not readily shown in a two-dimensional drawings. The bend 27 may be disposed at an angle of approximately 20 to 40 degrees, for example 30 degrees, from the longitudinal axis of the main portion of the introducer 26 extending outwardly from the incision in the apex 7.

The introducer 26 may optionally include a splitter (also referred to as the introducer hub) 32 configured to longitudinally split the shaft of the introducer 26 such that the introducer 26 forms a split catheter which can be easily removed while allowing an object within the lumen of the introducer 26 (e.g., the guidewire 24 and/or a portion of the implant 10) to remain within the lumen of the introducer 26. The splitter 32 may include a seal configured to allow another device and/or lumen to be selectively and removably sealed and/or advanced through the to the splitter 32 into the lumen of the introducer 26.

For example, the splitter 32 (introducer hub) may include at least two parts, namely, an outer shell made of a polymer that has been molded in such a way as to provide a preferential and controlled break-away seam, and the inner seal made of silicone rubber also with a molded break-away seam. The outer shell and silicone seal are mechanically connected so that the break-away seams are both positioned along the same axis as the shaft/lumen of the introducer 26. The splitter 32 (introducer hub) is mechanically connected to the proximal end of the introducer's tubular shaft. When the "handles" of the outer shell of the splitter 32 (introducer hub) are actuated in opposite directions, with sufficient force, rotating away from the axis of the introducer 26 toward the distal end of the introducer 26, the preferential break-away seams of the outer shell and of the inner seal of the splitter 32 (introducer hub) permanently separate and propagate a tear in the wall of the tube of the introducer 26. Continuing to further separate the handles of the splitter 32 (introducer hub) in turn continues to advance the tear in the tube of the introducer 26. The user continues to separate the handles, tearing the tube until the tear reached the distal end of the tube and completes the axial separation of the introducer 26.

One embodiment of a dilator 28 may include define at least one lumen configured to receive at least a portion of the delivery guide wire 24. For example, the lumen may have an internal diameter of approximately 0.038". The dilator 28 may also comprise a shaft including a tapered tip region 46. The tapered distal tip 46 may be provided to facilitate advancing the tip 46 into the puncture site in the apex 7 as the dilator 28 is introduced over the delivery guide wire 24. The shaft may comprise a plurality of segments or portions having different stiffness or hardness to produce the desired overall curvature. The shaft may be formed from one or more suitable polymers such as, but not limited to, a polyether block amide. The shaft may have a constant inner and/or outer diameter and may be made from different materials to provide the various stiffness or hardness. Alternatively, or in addition, the shaft may have different inner and/or outer diameters and may be made from one or more materials. For example, the various stiffness or hardness of the shaft may be provided by varying the thickness of the shaft at the different segments or portions. The different hardness of the segments may provide differing degrees of bending stiffness to the dilator 28 which may facilitate advancing the dilator 28 into and/or out of the left ventricle 3.

Figure 41:
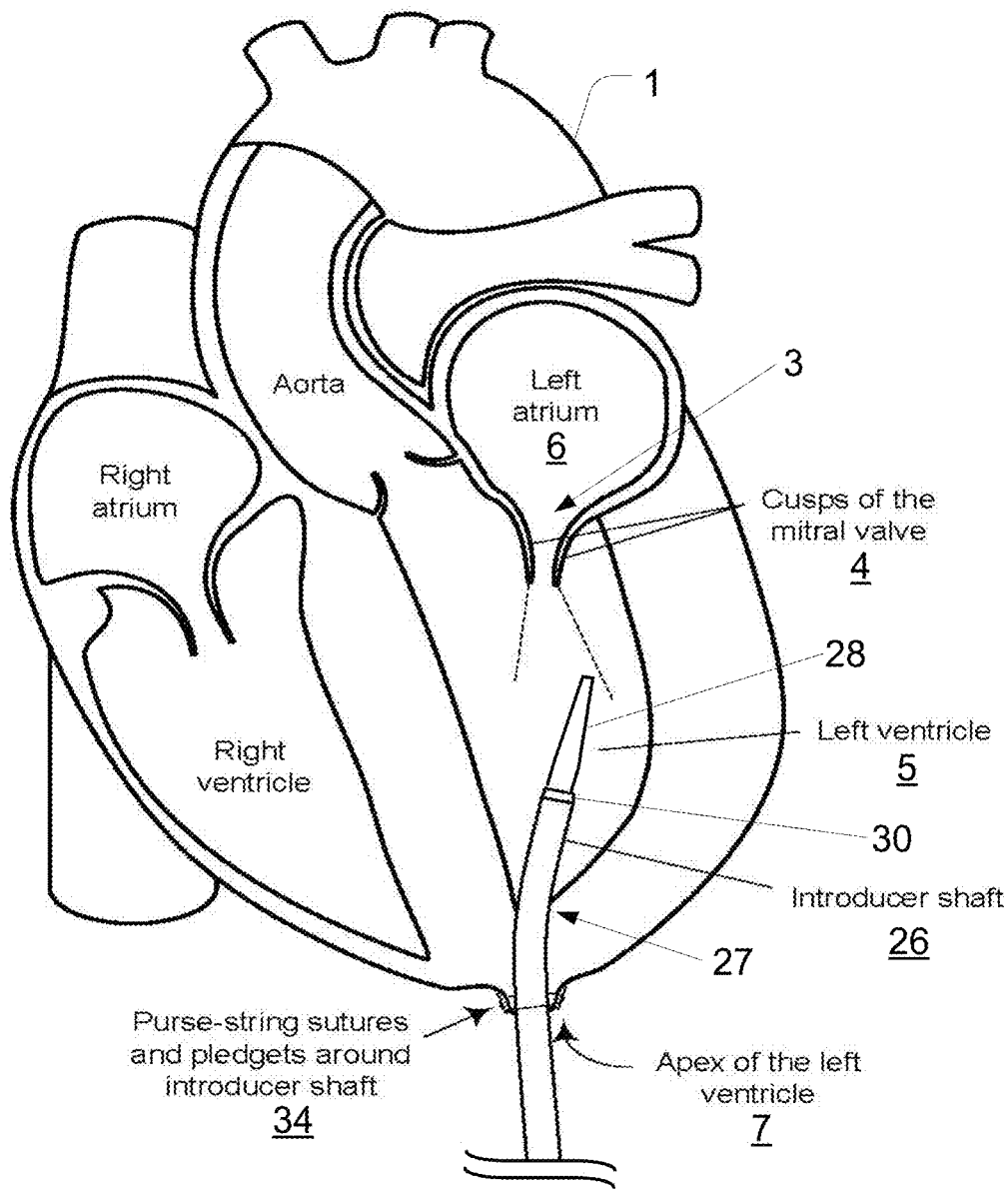
FIG. 41 illustrates the guidewire removed from the introducer.
Figure 42:
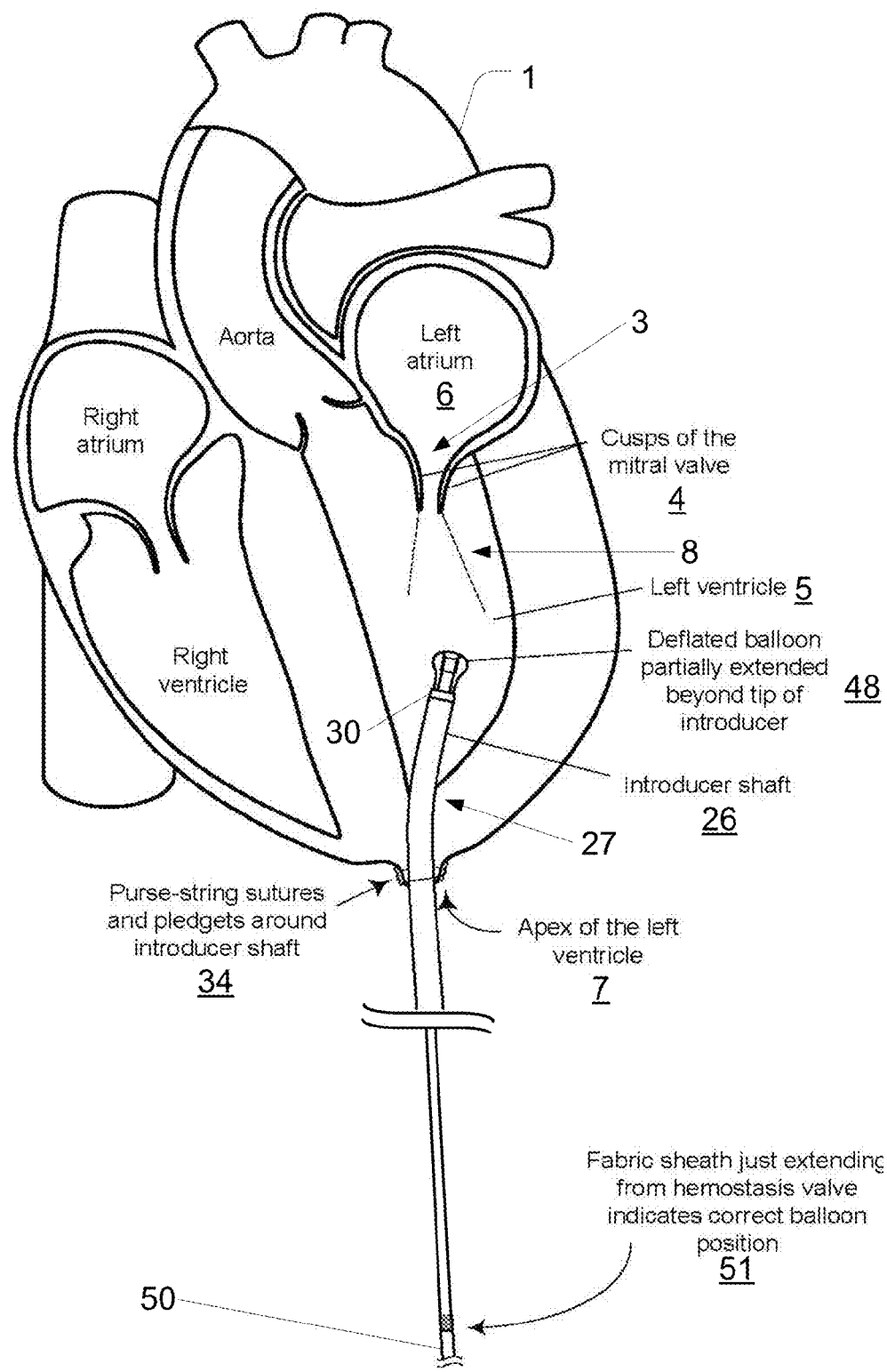
FIG. 42 illustrates one embodiment of an inflatable valve body partially beyond the tip of the introducer.

Once the introducer 26 is positioned in the left ventricle 5, the guidewire 24 may be removed, leaving the introducer 26 and dilator 28 in the left ventricle 5 as generally illustrated in FIG. 41. Because of the predetermined bend 27, the distal end 30 of the introducer 26 and/or dilator 28 is generally aligned with the mitral valve 3. A deflated inflatable valve body (balloon) 48 may be advanced through the lumen of the introducer 26 and/or dilator 28 until at least a portion of the inflatable valve body 48 exits the distal end 30 of the introducer 26 and/or dilator 28 as generally illustrated in FIG. 42 (the dilator 28 is shown retracted into the introducer 26 for clarity). A shaft 50 of the heart valve implant may include indicia 51 for indicating the position of the inflatable valve body 48 relative to the introducer 26. For example, when the indicia (which may include the proximal end of a fabric covering the shaft 50) is aligned with and/or protrudes a few millimeters from the splitter 32, about 1 cm of the inflatable valve body 48 is protruding from the end 30 of the introducer 26.

Figure 43:
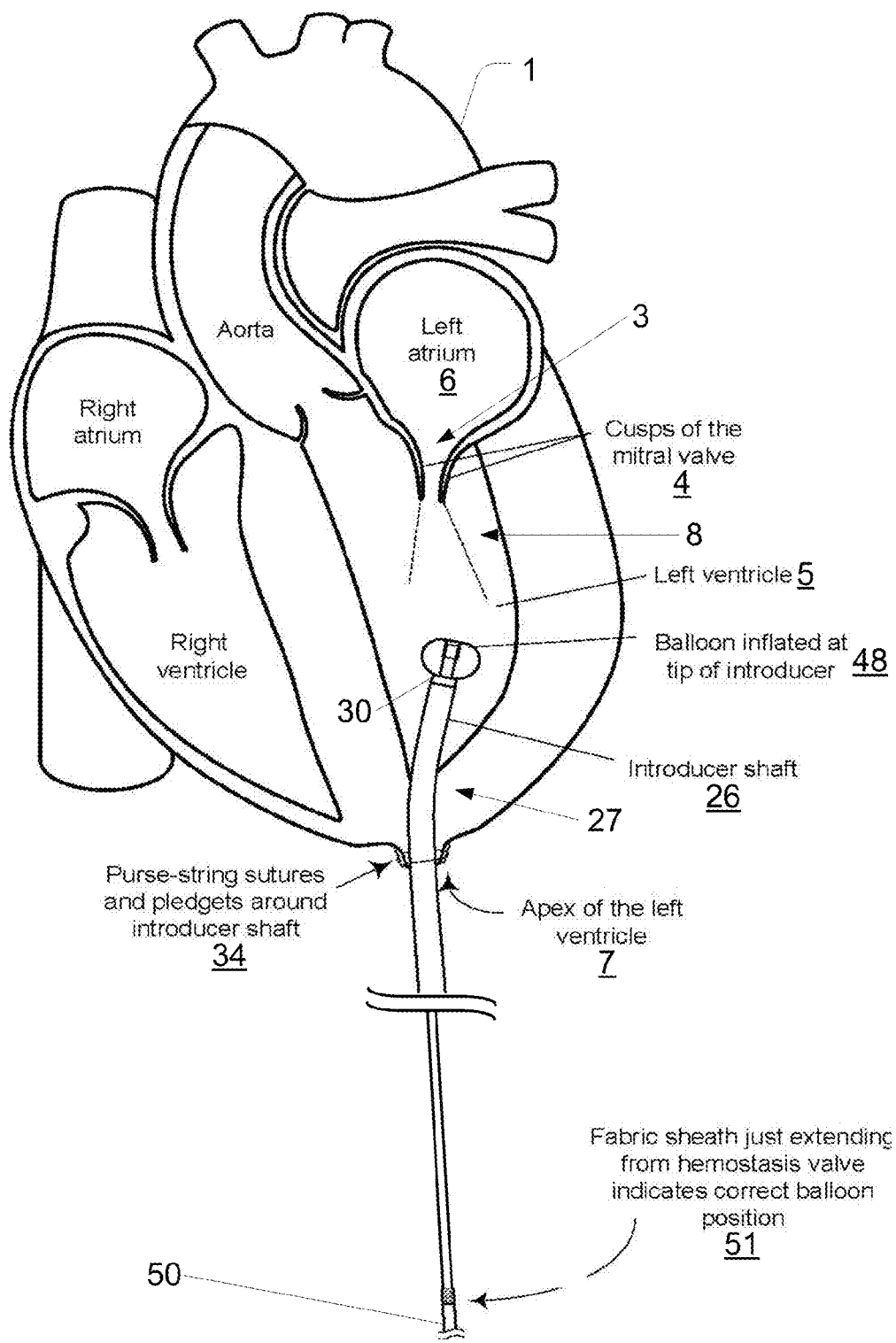
FIG. 43 illustrates the inflatable valve body partially inflated at the tip of the introducer.

The inflatable valve body 48, when partially expanded, is configured to facilitate atraumatic advancement of the introducer 26 and/or dilator 28 through the mitral valve 3 without damaging the mitral valve 3 or becoming entangled in the mitral valve 3 (for example, the cusps 4, the chordae and/or papillary muscles 8 of the mitral valve 3). The inflatable valve body 48 may be disposed proximate the distal end region of a shaft 50 and may be fluidly coupled through the shaft 50 to an expansion medium such as, but not limited to, a gas and/or liquid which may expand and/or enlarge the inflatable valve body 48 from the deflated or retracted position as generally illustrated in FIG. 42 to the inflated or expanded position as generally illustrated in FIG. 43 (note, that the inflatable valve body 48 is only partially extending from the introducer 26). The inflatable valve body 48 forms a soft tip which serves as an atraumatic "bumper" tip to minimize the risk of damaging or even irritating the delicate lining (endocardium) of the left ventricle 5. Physical contact with the left ventricle 5 can cause a dangerous arrhythmia. According to at least one embodiment, the expansion medium may include carbon dioxide ($CO_2$) gas, saline, or water. Optionally, contrast media may be introduced into the inflatable valve body 48 to allow the inflatable valve body 48 to be located using fluoroscopy or the like. In some embodiments, the contrast media coats the inside surface of the inflatable valve body 48, so that an outline of the entire inflatable valve body is observed.

The inflatable valve body 48 may include a resiliently expandable/collapsible material such as, but not limited to, silicone, Yulex™ or the like which may be selectively collapsed and/or expanded. The inflatable valve body 48 may be bonded to the shaft 50 and may include one or more passageways, apertures or lumens to allow the expansion medium to expand/collapse the inflatable valve body 48. The diameter of the inflatable valve body 48 should be small enough in the first or retracted/collapsed position through the introducer 26 and/or dilator 28 to the left ventricle 5 and large enough when in the second or expanded/inflated position to be advanced through the cusps 4 and chordae 8 of the mitral valve 3 to reduce the potential of damaging the heart 1 and/or getting entangled within the mitral valve 3. For example, the shaft 50 may have an outer diameter of approximately 0.062" (e.g., a 5 Fr). In one embodiment, the inflatable valve body 48 has a diameter of approximately 0.01 inches to 0.50 inches in the first position. In another embodiment, the inflatable valve body has a diameter of approximately 0.05 to 0.25 inches in the first position. In one embodiment, the inflatable valve body has approximately a 0.100" in the first position. In another embodiment, the inflatable valve body has a diameter of approximately 15 mm to approximately 20 mm in the second position with a length of approximately 8 to approximately 10 mm.

Figure 44:
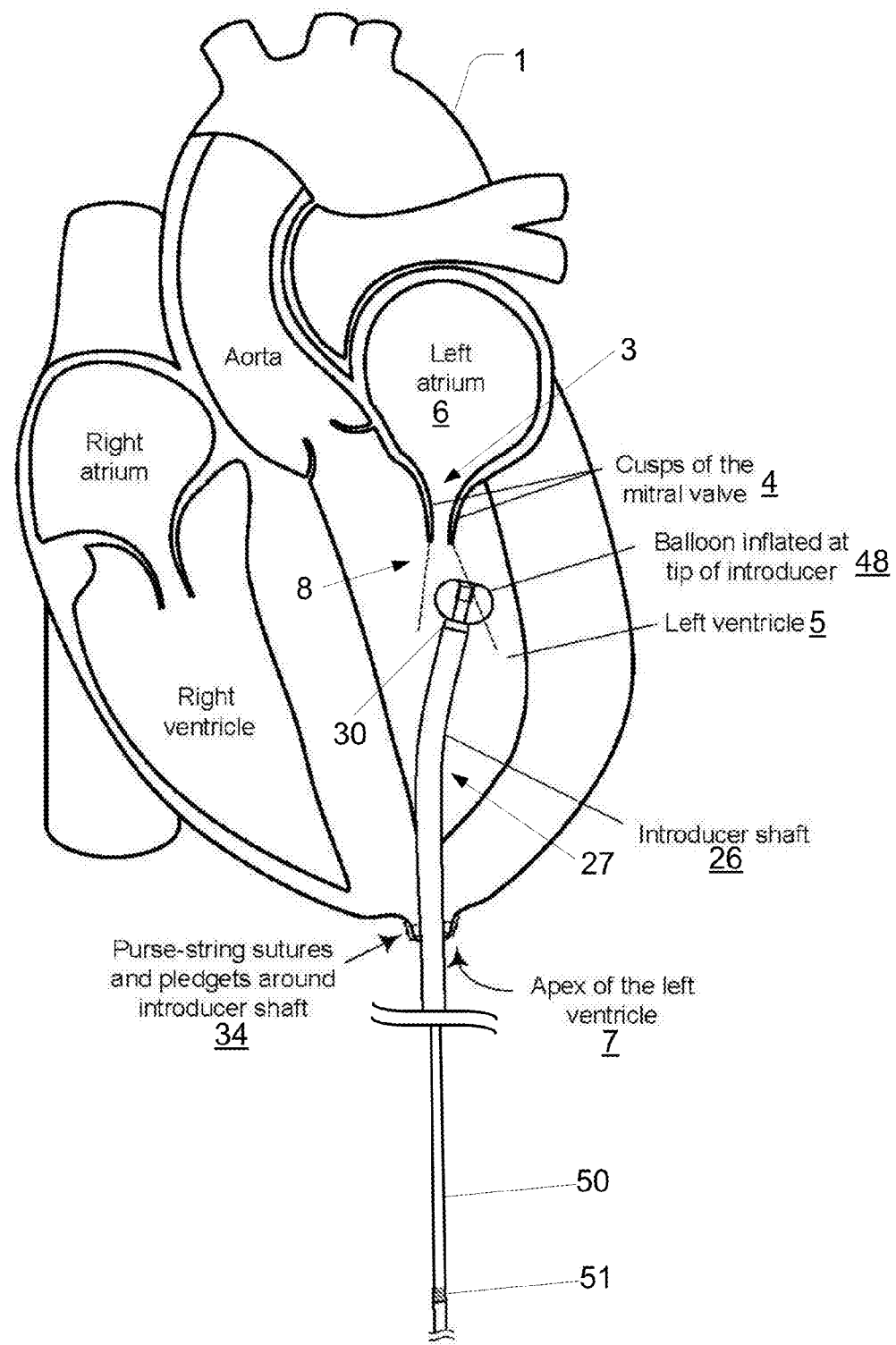
FIG. 44 illustrates the inflatable valve body being advanced through the mitral valve.

The inflatable valve body 48 is advanced towards the mitral valve 3 as generally illustrated in FIG. 44. As can be seen, the bend 27 in the introducer 26 helps to get the introducer 26 correctly orientated spatially, to find the space between the two papillary muscles and avoid the chordae. As noted above, the limitations of the two-dimensional figures do not completely convey the advantage of the bend 27. With the inflatable valve body 48 proximate to the mitral valve 3, the inflatable valve body 48 may be advanced through the mitral valve 3. The backflow from the left ventricle 5 through the mitral valve 3 into the left atrium 6 (even for a normal mitral valve) helps "pull" the inflated inflatable valve body 48 into the mitral space such that the inflatable valve body 48 may ultimately be advanced into the left atrium 6 as generally illustrated in FIGS. 24 and 25. The introducer 26 and the dilator 28 may then be advanced into the left atrium 6.

As previously described, placement of the inflatable valve body 48 is confirmed with one or more radiopaque markers and/or contrast media within the inflatable valve body using fluoroscopy.

After delivery of the heart valve implant as described herein, the inflatable valve body is configured to reduce or restrict the amount of blood flow (i.e., regurgitation) through the valve in a closed position. In some embodiments, about 100% of the blood flow (mitral valve regurgitation) through the valve in a closed position is eliminated, reduced, or restricted (i.e., treated). In other words, after delivery of the heart valve implant, there is little to no mitral valve regurgitation. In other embodiments, less than 100% (i.e., 99%, 98%, 97%, 96%, 95%, 90%, 85, 80%, 75%, 70%, 65%, 60%, 55%, 50%, 45%, 40%, 35%, 30%, 25%, 20%, 15%, 10%, 5%, 4%, 3%, 2%, 1%, or less) of the mitral valve regurgitation is eliminated, reduced or restricted (i.e., treated). As will be appreciated by one of skill in the art, the amount of reduction of mitral valve regurgitation is adjusted with the amount of expansion medium (inflation fluid) injected into injection port (FIGS. 29B-29C). The amount (volume) of expansion medium within the inflatable valve body affects the amount of blood flow through the valve in a closed position that occurs.

In some embodiments, the method of trans-apically delivering a heart valve implant within a heart further comprises adjusting the amount (e.g., volume) of inflation fluid within the inflatable valve body to eliminate, reduce, or restrict (i.e., treat) the amount of blood flow when the heart valves are in a closed position or the amount regurgitation. The reduction, restriction, or elimination of an amount of blood flow when the heart valves are in a closed position or the amount of regurgitation can be measured as a percentage (e.g., % reduction from a baseline), a volume (e.g., milliliters, liters, etc.), or another appropriate unit of measure. It will be apparent to one of skill in the art, that a 100% reduction of regurgitation immediately after delivery of the heart valve implant may not be the most effective treatment for certain patients or individuals. It will also be apparent to one of skill in the art, that a 100% reduction or complete elimination of regurgitation after all treatments may not be the most effective as well. In some embodiments, a gradual reduction of regurgitation through the heart valve implant occurs over a period of time and is performed with one more treatments (e.g., adjustments of the inflatable valve body).

In one embodiment, the heart valve implant causes a reduction of blood flow when the heart valves are in a closed position of at least 1% to about 100%. In another embodiment, the reduction of regurgitation is about 5% to about 90%. In another embodiment, the reduction is about 10% to about 80%. In another embodiment, the reduction is about 15% to about 70%. In another embodiment, the reduction is about 20% to about 60%. In another embodiment, the reduction is about 25% to about 50%. In another embodiment, the reduction is about 30% to about 60%. In another embodiment, the reduction is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, gradually correcting the blood flow when the heart valves are in a closed position allows the cardiopulmonary system and/or other organ systems to adjust to the physiological changes (e.g., increased cardiac output and ejection fraction) as a result of the reduced regurgitation.

In some embodiments, the methods described herein comprise reducing, restricting, or eliminating regurgitation that occurs over one or more (e.g., 2, 3, 4, 5, 6, 7, 8, 9, 10 or more) treatments. As used herein, a "treatment" comprises any intervention that affects the cardiovascular system in an individual. In one embodiment, a treatment comprises adjusting the inflatable valve body via the injection (inflation) port with an expansion medium. In another embodiment, a treatment comprises adjusting the position of the heart valve implant within the heart. In another embodiment, a treatment comprises adjusting the inflatable valve body via the injection (inflation) port with an expansion medium and adjusting the position of the heart valve implant within the heart.

In some embodiments, the method further comprises one or more treatments administered over a period of time. It will be readily apparent to one of skill in the art any number of treatments and any period of time between each treatment are possible. In one embodiment, each treatment is administered every one or more (e.g., 2, 3, 4, 5, 6, 7, 7, 8, 9, 10, or more) days. In another embodiment, each treatment is administered every other day (e.g., every 2 days). In another embodiment, each treatment is administered every 3 days. In another embodiment, each treatment is administered every 4 days. In another embodiment, each treatment is administered every 5 days. In another embodiment, each treatment is administered every 6 days. In another embodiment, each treatment is administered every 7 days (week). In another embodiment, each treatment is administered every one or more (e.g., 2, 3, 4, 5, 6, 7, 8, 9, 10, or more) weeks. In one embodiment, each treatment is administered every other week. In one embodiment, each treatment is administered every 3 weeks. In one embodiment, each treatment is administered every 4 weeks. In one embodiment, each treatment is administered every 5 weeks. In one embodiment, each treatment is administered every 6 weeks. In one embodiment, each treatment is administered every 7 weeks. In one embodiment, each treatment is administered every 8 weeks. In another embodiment, each treatment is administered every one or more months (e.g., 2, 3, 4, 5, 6, 7, 8, 9, 10, or more). In one embodiment, each treatment is administered every other month. In one embodiment, each treatment is administered every 3 months. In one embodiment, each treatment is administered every 4 months. In one embodiment, each treatment is administered every 5 months. In one embodiment, each treatment is administered every 6 months. In one embodiment, each treatment is administered every 7 months. In one embodiment, each treatment is administered every 8 months. In one embodiment, each treatment is administered every 9 months. In one embodiment, each treatment is administered every 10 months. In one embodiment, each treatment is administered every 11 months. In one embodiment, each treatment is administered every 12 months. In one embodiment, each treatment is administered once every year or more. In another embodiment, the period of time between each treatment varies.

By way of example, after delivery of the heart valve implant, the inflatable valve body is inflated so that about a 10-30% reduction of regurgitation is corrected in the first treatment. After a period of time (e.g., one or more days, one or more weeks, or one or more months), the inflatable valve body is further adjusted (i.e., inflated) so that an additional 10-30% of the regurgitation is corrected in a second treatment. Since the inflation (injection) port is subdermally located in a patient, access and inflation of the inflatable valve body is performed without the need of an additional surgery. After an additional period of time (e.g., one or more days, one or more weeks, or one or more months), the inflatable valve body is even further expanded (i.e., inflated) so that an additional 10-30% of the regurgitation is reduced in a third treatment. In some embodiments, individuals with the heart valve implant are routinely monitored and treatments are modified or altered as necessary. At the end of the one or more treatments, all (100%) or a portion (less than 100%) of the regurgitation is corrected. One of skill in the art will readily appreciate that the treatment scheduling and amount of treatment administered (i.e., reduction of regurgitation) will vary from individual to individual.

The methods and implants described herein are used for the treatment of mitral valve regurgitation. The cause or underlying etiology of the mitral valve regurgitation may be known or unknown (idiopathic). For example, mitral valve prolapse, damaged tissue cords (cordae tendineae), rheumatic fever, endocarditis, age-related regurgitation, myocardial infarction, hypertension, and congenital heart defects can all cause mitral valve regurgitation.

According to one aspect, the present disclosure features a trans-apical implant. The implant includes an inflatable valve body defining spacer cavity configured to be expanded from a retracted position, a shaft extending from the inflatable valve body, the shaft defining an inflation lumen fluidly coupled to the spacer cavity and fluidly coupled to an inflation device. The inflation device can seal said inflation lumen and can allow selectively introducing allow an expansion medium (inflation fluid) to flow into the spacer cavity so as to selectively expand the spacer body from a retracted position to an expanded position. Alternatively, the inflation device can be used to extract at least a portion of an expansion medium from the spacer cavity. Thus, the inflation device allows adjusting the degree of expansion of the spacer body.

According to another aspect, the present disclosure features an implant delivery system. The implant delivery system includes an introducer having at least one lumen and an implant. The implant is configured to be received in the lumen and includes an inflatable valve body and a shaft. The inflatable valve body defines spacer cavity configured to be expanded from a retracted position while disposed within the lumen of the introducer. The shaft is configured to extend from the spacer and defines an inflation lumen fluidly coupled to the spacer cavity and fluidly coupled to an inflation device.

According to yet another aspect, the present disclosure provides a method of implanting an implant within a heart. The implant includes a shaft and an inflatable valve body configured to interact with at least a portion of at least one cusp of a mitral valve to at least partially restrict a flow of blood through the heart valve in a closed position. The method includes trans-septally advancing a guide wire to left ventricle of the heart; piercing the left ventricle at a puncture site corresponding to an implant site; advancing a distal end of the guide wire through the puncture and out of an incision in the torso of a patient; trans-apically advancing an introducer over the guide wire through the incision, into the puncture site of the heart, and into the left ventricle; advancing the introducer over the guide wire through the mitral valve into a left atrium of the heart; advancing the implant through a lumen, defined by the introducer, into the left atrium, wherein the shaft extends within the lumen from the spacer and beyond the puncture site; introducing an expansion medium (inflation fluid) through the shaft to expand the inflatable valve body; locating the inflatable valve body within a mitral valve of the heart to reduce (and in some cases eliminating) mitral regurgitation; removing the introducer from the heart; and securing the implant to an external surface of the heart proximate to the puncture site.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure as determined by the claims when interpreted in accordance with breadth to which they are fairly, legally and equitably entitled.

What is claimed:

1. A heart valve implant comprising:
   an inflatable valve body defining a cavity comprising a proximal end and a distal end;
   a shaft extending through the proximal end of the inflatable valve body, said shaft comprising a lumen in fluid communication with said cavity;
   an anchor assembly attached to the shaft, proximal to the inflatable valve body; and
   an inflation port comprising one or more lumens in fluid communication with the shaft lumen, wherein said inflation port is configured to be secured subdermally;
   wherein:
   the anchor assembly comprises a passageway and two arms;
   the passageway is positioned between said two arms and is configured to receive and advance the shaft;
   each of the two arms defines an opening; and
   the anchor assembly is configured to be secured to an exterior surface of an individual's heart.

2. The heart valve implant of claim 1, further comprising one or more radiopaque markers.

3. The heart valve implant of claim 2, wherein the one or more radiopaque markers are at or near the proximal end of the inflatable valve body.

4. The heart valve implant of claim 1, wherein the inflation port further comprises a pierceable septum configured to fluidly seal the inflation port.

5. The heart valve implant of claim 4, wherein the pierceable septum comprises silicone.

6. The heart valve implant of claim 5, wherein the inflation port further comprises one or more suture holes.

7. The heart valve implant of claim 4, wherein the pierceable septum is liquid-tight.

8. The heart valve implant of claim 1, wherein one or more sutures are placed around each of the two arms of the anchor assembly.

9. The heart valve implant of claim 1, wherein the inflatable valve body is partially or completely inflated with an inflation fluid.

10. The heart valve implant of claim 1, wherein the shaft is attached to the distal end of the inflatable valve body.

11. The heart valve implant of claim 10, wherein the lumen in fluid communication with the inflatable valve body comprises one or more openings.

* * * * *